US008486420B2

(12) United States Patent
Johnston et al.

(10) Patent No.: US 8,486,420 B2
(45) Date of Patent: Jul. 16, 2013

(54) LIVE VIRUS VACCINES

(75) Inventors: Robert E. Johnston, Chapel Hill, NC (US); Philip R. Johnson, Bryn Mawr, NC (US); Christy K. Jurgens, Somerset, NJ (US); Kelly Young Poe, Germantown, MD (US)

(73) Assignees: The University of North Carolina at Chapel Hill, Chapel Hill, NC (US); Children's Hospital, Inc., Columbus, OH (US)

( * ) Notice: Subject to any disclaimer, the term of this patent is extended or adjusted under 35 U.S.C. 154(b) by 547 days.

(21) Appl. No.: 11/816,360

(22) PCT Filed: Feb. 15, 2006

(86) PCT No.: PCT/US2006/005338
§ 371 (c)(1),
(2), (4) Date: Sep. 21, 2007

(87) PCT Pub. No.: WO2007/046839
PCT Pub. Date: Apr. 26, 2007

(65) Prior Publication Data
US 2008/0260775 A1    Oct. 23, 2008

Related U.S. Application Data

(60) Provisional application No. 60/653,255, filed on Feb. 15, 2005.

(51) Int. Cl.
*A61K 39/21*    (2006.01)
*C12N 7/00*    (2006.01)

(52) U.S. Cl.
USPC .................................. 424/208.1; 435/320.1

(58) Field of Classification Search
None
See application file for complete search history.

(56) References Cited

U.S. PATENT DOCUMENTS

| 4,650,764 A | 3/1987 | Temin et al. |
| 5,091,309 A | 2/1992 | Schlesinger et al. |
| 5,185,440 A | 2/1993 | Davis et al. |
| 5,217,879 A | 6/1993 | Huang et al. |
| 5,505,947 A | 4/1996 | Johnston et al. |

(Continued)

FOREIGN PATENT DOCUMENTS

| EP | 0 659 885 A1 | 12/1994 |
| WO | WO 92/10578 | 6/1992 |

(Continued)

OTHER PUBLICATIONS

Foley, et al., Rhabdovirus-Based Vectors with Human Immunodeficiency Virus Type 1 (HIV-1) Envelopes Display HIV-1-Like Tropism and Target Human Dendritic Cells. J Virol. 2002; 76(1):19-31.*

(Continued)

*Primary Examiner* — Zachariah Lucas
*Assistant Examiner* — Stuart W Snyder
(74) *Attorney, Agent, or Firm* — Myers Bigel Sibley & Sajovec, P.A.

(57) ABSTRACT

The present invention provides novel self-replicating and self-propagating chimeric viral vectors and chimeric virus particles comprising a modified genome of a carrier RNA virus packaged within structural proteins of a second virus. Also provided are pharmaceutical formulations comprising the chimeric viral vectors and virus particles and methods of inducing an immune response by administration of the same to a subject.

41 Claims, 16 Drawing Sheets

U.S. PATENT DOCUMENTS

| | | | |
|---|---|---|---|
| 5,639,650 | A | 6/1997 | Johnston et al. |
| 5,643,576 | A | 7/1997 | Johnston et al. |
| 5,739,026 | A | 4/1998 | Garoff et al. |
| 5,766,602 | A | 6/1998 | Xiong et al. |
| 5,789,245 | A | 8/1998 | Dubensky et al. |
| 5,792,462 | A | 8/1998 | Johnston et al. |
| 5,811,407 | A | 9/1998 | Johnston et al. |
| 5,814,482 | A | 9/1998 | Dubensky, Jr. et al. |
| 5,843,723 | A | 12/1998 | Dubensky, Jr. et al. |
| 5,951,975 | A | 9/1999 | Falo, Jr. et al. |
| 5,994,126 | A | 11/1999 | Steinman et al. |
| 6,004,807 | A | 12/1999 | Banchereau et al. |
| 6,008,035 | A | 12/1999 | Johnston et al. |
| 6,013,516 | A | 1/2000 | Verma et al. |
| 6,015,694 | A | 1/2000 | Dubensky et al. |
| 6,156,304 | A | 12/2000 | Glorioso et al. |
| 6,156,558 | A | 12/2000 | Johnston et al. |
| 6,190,666 | B1 | 2/2001 | Garoff et al. |
| 6,224,879 | B1 | 5/2001 | Sjoberg et al. |
| 6,242,259 | B1 | 6/2001 | Polo et al. |
| 6,277,633 | B1 | 8/2001 | Olsen |
| 6,376,236 | B1 | 4/2002 | Dubensky, Jr. et al. |
| 6,468,982 | B1 | 10/2002 | Weiner et al. |
| 6,521,235 | B2 | 2/2003 | Johnston et al. |
| 6,521,457 | B2 | 2/2003 | Olsen |
| 6,531,135 | B1 | 3/2003 | Johnston et al. |
| 6,541,010 | B1 | 4/2003 | Johnston et al. |
| 6,583,121 | B1 | 6/2003 | Johnston et al. |
| 6,783,939 | B2 | 8/2004 | Olmsted et al. |
| 6,844,188 | B1 | 1/2005 | MacDonald et al. |
| 7,045,335 | B2 | 5/2006 | Smith et al. |
| 2001/0016199 | A1 | 8/2001 | Johnston et al. |
| 2003/0232035 | A1 | 12/2003 | Dubensky, Jr. et al. |
| 2003/0232036 | A1 | 12/2003 | Johnston et al. |
| 2003/0232324 | A1* | 12/2003 | Polo et al. ............ 435/5 |
| 2004/0030117 | A1 | 2/2004 | Johnston et al. |
| 2004/0121466 | A1 | 6/2004 | Johnston et al. |
| 2004/0166573 | A1 | 8/2004 | Smith et al. |
| 2004/0175829 | A1 | 9/2004 | Makino et al. |
| 2004/0208848 | A1 | 10/2004 | Smith et al. |
| 2004/0235133 | A1 | 11/2004 | Frolov et al. |
| 2005/0054107 | A1 | 3/2005 | Chulay et al. |
| 2005/0123555 | A1 | 6/2005 | Olmsted et al. |
| 2006/0099587 | A1 | 5/2006 | Johnston et al. |
| 2006/0177819 | A1 | 8/2006 | Smith et al. |
| 2007/0166820 | A1 | 7/2007 | Smith et al. |

FOREIGN PATENT DOCUMENTS

| | | |
|---|---|---|
| WO | WO 95/07994 | 3/1995 |
| WO | WO 95/27044 | 10/1995 |
| WO | WO 95/31565 | 11/1995 |
| WO | WO 95/32733 | 12/1995 |
| WO | WO 96/17072 | 6/1996 |
| WO | WO 96/21416 | 7/1996 |
| WO | WO 96/37220 | 11/1996 |
| WO | WO 96/37616 | 11/1996 |
| WO | WO 97/24447 | 7/1997 |
| WO | WO 97/38087 | 10/1997 |
| WO | WO 98/00163 | 1/1998 |
| WO | WO 98/36779 | 8/1998 |
| WO | WO 99/30734 | 6/1999 |
| WO | WO 99/51263 | 10/1999 |
| WO | WO 00/39318 | 7/2000 |
| WO | WO 01/16343 | 3/2001 |
| WO | WO 01/47456 | 7/2001 |
| WO | WO 02/20721 | 3/2002 |
| WO | WO 02/098457 A2 | 12/2002 |
| WO | WO 02/099035 A2 | 12/2002 |
| WO | WO 03/083065 | 10/2003 |
| WO | WO 2004/044157 A2 | 5/2004 |
| WO | WO 2005/027840 A2 | 3/2005 |
| WO | WO 2007/046869 A2 | 4/2007 |

OTHER PUBLICATIONS

McKenna, et al., Covalently Linked Human Immunodeficiency Virus Type 1 gp120/gp41 Is Stably Anchored in Rhabdovirus Particles and Exposes Critical Neutralizing Epitopes. J. Virol. 2003; 77(23):12782-12794.*

Berglund, et al. Outcome of Immunization of Cynomolgus Monkeys with Recombinant Semliki Forest Virus Encoding Human Immunodeficiency Virus Type 1 Envelope Protein and Challenge with a High Dose of SHIV-4 Virus. AIDS Res. Hum. Retroviruses; 1997 13(17):1487-1495.*

Perri, et al. An Alphavirus Replicon Particle Chimera Derived from Venezuelan Equine Encephalitis and Sindbis Viruses Is a Potent Gene-Based Vaccine Delivery Vector. J. Virol. 2003; 77(19): 10394-10403.*

Harvey, et al. Kunjin Virus Replicon Vectors for Human Immunodeficiency Virus Vaccine Development. J. Virol. 2003; 77(14):7796-7803.*

Mossman, et al. Protection against Lethal Simian Immunodeficiency Virus SIVsmmPBj14 Disease by a Recombinant Semliki Forest Virus gp160 Vaccine and by a gp120 Subunit Vaccine. J. Virol. 1996; 70(3):1953-1960.*

Berglund, et al. AIDS Res. Hum. Retroviruses 1997 13(17):1487-1495.*

Davis et al. A Viral Vaccine Vector That Expresses Foreign Genes in Lymph Nodes and Protects against Mucosal Challenge. J. Virol. 1996; 70(6):3781-3787.*

Caley, et al. Humoral, Mucosal, and Cellular Immunity in Response to a Human Immunodeficiency Virus Type 1 Immunogen Expressed by a Venezuelan Equine Encephalitis Virus Vaccine Vector. J. Virol. 1997; 71(4): 3031-3038.*

R Swanstrom and JW Wills. Synthesis, Assembly, and Processing of Viral Proteins. Retroviruses. Cold Spring Harbor (NY): Cold Spring Harbor Laboratory Press; 1997 (Coffin JM, Hughes SH, Varmus HE, editors).*

Syomin, et al. Effect of Nucleocapsid on Multimerization of gypsy Structural Protein GAG. Molecular Biology, 2012, vol. 46, No. 2, pp. 270-278.*

Jurgens, et al. A Novel Self-Replicating Chimeric Lentivirus-Like Particle. J. Virol. 2012; 80(1): 346-361.*

Tobin, et al. Chimeric HIV-1 Virus-like Particles Containing gp120 Epitopes as a Result of a Ribosomal Frameshift Elicit Gag- and SU-Specific Murine Cytotoxic T-Lymphocyte Activities. Virology. 1997; 236, 307-315.*

Megede, et al. Evaluation of human immunodeficiency virus type 1 subtype C gag, pol, and gagpol DNA and alphavirus replicon vaccines. Vaccine. 2006; 24: 2755-2763.*

Davis, et al. Alphavirus Replicon Particles as Candidate HIV Vaccines. IUBMB Life, 2002; 53(4-5): 209-211.*

Davis et al., "Alphavirus Replicon Particles as Candidate HIV Vaccines" *IUBMB Life* 53:209-211 (2002).

Williamson et al., "Characterization and Selection of HIV-1 Subtype C Isolates for Use in Vaccine Development" *AIDS Research and Human Retroviruses* 19(2):133-144 (2003).

Bortiz Eli et al., "Replication-Competent Rhabdoviruses with Human Immunodeficiency Virus Type 1 Coats and Green Fluorescent Protein: Entry by a pH-Independent Pathway", Journal of Virology, Aug. 1999, p. 6937-6945; vol. 73, No. 8.

Gregory S. et al., "HIV-1 pseudotype virus containing a Cocal virus genome and an HIV envelope: construction, assay and use", Journal of Virological Methods, Oct. 1993, vol. 44, No. 2-3, p. 287-304.

McGettigan, James P. et al., "Expression and Immunogenicity of Human Immunodeficiency Virus Type 1 Gag Expressed by a Replication-Competent Rhabdovirus-Based Vaccine Vector", Journal of Virology, Sep. 2001, p. 8724-8732, vol. 75, No. 18.

Communication pursuant to Article 94(3) EPC corresponding to European Application No. 06 844 071.8 dated Dec. 10, 2010; 6 pages.

Frolov et al., "Sindbis Virus Replicons and Sindbis Virus: Assembly of Chimeras and of Particles Deficient in Virus RNA", Journal of Virology, Apr. 1997, p. 2819-2829, XP-002139371.

Balasuriya et al. "Alphavirus Replicon Particles Expressing the Two Major Envelope Proteins of Equine Arteritis Virus Induce High Level Protection Against Challenge with Virulent Virus in Vaccinated Horses" *Vaccine* 20:1609-1617 (2002).

Balasuriya et al. "Expression of the Two Major Envelope Proteins of Equine Arteritis Virus as a Heterodimer is Necessary for Induction of Neutralizing Antibodies in Mice Immunized with Recombinant Venezuelan Equine Encephalitis Virus Replicon Particles" *Journal of Virology* 74(22):10623-10630 (2000).

Barclay et al. "Encapsidation Studies of Poliovirus Subgenomic Replicons" *Journal of General Virology* 279:1725-1734 (1998).

Barrett et al. "Antibody-mediated Early Death in vivo after Infection with Yellow Fever Virus" *Journal of General Virology* 67:2530-2542 (1986).

Berge et al. "Studies on the Virus of Venezuelan Equine Encephalomyelitis," *Journal of Immunology* 87:509-517 (1961).

Berglund et al. "Outcome of Immunization of Cynomolgus Monkeys with Recombinant Semliki Forest Virus Encoding Human Immunodeficiency Virus Type 1 Envelope Protein and Challenge with a High Dose of SHIV-4 Virus" *Aids Research and Human Retroviruses* 13(17):1487-95 (1997).

Bernard et al. "Mutations in the E2 Glycoprotein of Venezuelan Equine Encephalitis Virus Confer Heparan Sulfate Interaction, Low Morbidity, and Rapid Clearance from Blood of Mice" *Virology* 276:93-103 (2000).

Bredenbeek et al. "Sindbis Virus Expression Vectors: Packaging of RNA Replicons by Using Defective Helper RNAs" *Journal of Virology* 67(11):6439-6446 (1993).

Bukreyev et al. "A Single Intranasal Inoculation with a Paramyxovirus-Vectored Vaccine Protects Guinea Pigs Against a Lethal-Dose Ebola Virus Challenge" *Journal of Virology* 80(5):2267-2279 (2006).

Bukreyev et al. "Recombinant Newcastle Disease Virus Expressing a Foreign Viral Antigen is Attenuated and Highly Immunogenic in Primates" *Journal of Virology* 79(21):13275-13284 (2005).

Bulychyov et al. "Disease Course in Guinea Pigs After Aerogenous Infection with Venezuelan Equine Encaphalomyelitis Virus" ISSN 0507-4088 (1995) (Abstract only).

Caley et al. "Humoral, Mucosal, and Cellular Immunity in Response to a Human Immunodeficiency Virus Type 1 Immunogen Expressed by a Venezuelan Equine Encephalitis Virus Vaccine Vector" *Journal of Virology* 71(4):3031-3038 (1997).

Carl et al. "Effect of the Attenuating Deletion and of Sequence Alterations Evolving In Vivo on Simian Immunodeficiency Virus C8-Nef Function" *Journal of Virology* 73(4):2790-2797 (1999).

Chanas et al. "Monoclonal Antibodies to Sindbis Virus Glycoprotein E1 can Neutralize, Enhance Infectivity, and Independently Inhibit Haemagglutination or Haemolysis" *Journal of General Virology* 58:37-46 (1982).

Chang et al. "Retroviral Vectors for Gene Therapy of AIDS and Cancer" *Current Opinion in Molecular Therapeutics* 3(5):468-475 (2001).

Corsini et al. "Efficiency of Transduction by Recombinant Sindbis Replicon Virus Varies Among Cell Lines, Including Mosquito Cells and Rat Sensory Neurons" *Bio Techniques* 21(3):492-497 (Sep. 1996).

Curtis et al. "Heterologous Gene Expression from Transmissible Gastroenteritis Virus Replicon Particles" *Journal of Virology* 76(3):1422-1434 (2002).

Davis et al, "A Genetically Engineered Live Virus Vaccine for Venezuelan Equine Encephalitis" *J. Cell Biochemistry* Supplement O No. 17 Part D, issued 1993, Abstract N404.

Davis et al. "A molecular genetic approach to the study of Venezuelan equine encephalitis virus pathogenesis" *Archives of Virology* 9:99-109 (1994).

Davis et al. "An Attenuated VEE Virus Vaccine Vector: Expression of HIV-1 and Influenza Genes in Cell Culture and Protection Against Influenza Challenge in Mice Immunized with a Vector Expressing HA" *Vaccines* 387-391 (1995).

Davis et al. "Attenuated Mutants of Venezuelan Equine Encephalitis Virus Containing Lethal Mutations in the PE2 Cleavage Signal Combined with a Second-Site Suppressor Mutation in E1" *Virology* 212:102-110 (1995).

Davis et al. "Attenuating Mutations in the E2 Glycoprotein Gene of Venezuelan Equine Encephalitis Virus: Construction of Single and Multiple Mutants in a Full-Length cDNA Clone" *Virology* 183:20-31 (1991).

Davis et al. "A Viral Vaccine Vector that Expresses Foreign Genes in Lymph Nodes and Protects Against Mucosal Challenge" *Journal of Virology* 70(6): 3781-3787 (1996).

Davis et al. "In Vitro Synthesis of Infectious Venezuelan Equine Encephalitis Virus RNA from a cDNA Clone: Analysis of a Viable Deletion Mutant[1]," *Virology* 171:189-204 (1989).

Davis et al. "In Vitro Synthesis of Infectious Venezuelan Equine Encephalitis Virus RNA from a cDNA Clone: Analysis of a Viable Deletion Mutant and Mutations Affecting Virulence" *Vaccines* 90:109-113 (1990).

Davis et al. "Vaccination of Macaques Against Pathogenic Simian Immunodeficiency Virus with Venezuelan Equine Encephalitis Virus Replicon Particles" *Journal of Virology* 74(1):371-378 (2000).

De Veerman et al. "Retrovirally Transduced Bone Marrow-Derived Dendritic Cells Require CD4[+] T Cell Help to Elicit Protective and Therapeutic Antitumor Immunity" *The Journal of Immunology* 162:144-151 (1999).

Dietz et al. "High Efficiency Adenovirus-Mediated Gene Transfer to Human Dendritic Cells" *Blood* 91(2):392-398 (1998).

Disis et al. "Peptide-Based, but Not Whole Protein, Vaccines Elicit Immunity to HER-2/neu, an Oncogenic Self-Protein[1]" *Journal of Immunology* 156:3151-3158 (1996).

Dubensky, Jr. et al. "Sindbis Virus DNA-Based Expression Vectors: Utility for in Vitro and in Vivo Gene Transfer," *Journal of Virology* 70(1):508-519 (Jan. 1996).

Engler et al. "Venezuelan Equine Encephalitis-Specific Immunoglobulin Responses: Live Attenuated TC-83 Versus Inactivated C-84 Vaccine" *Journal of Medical Virology* 38:305-310 (1992).

Evans et al. "A Novel Approach for Producing Lentiviruses That are Limited to a Single Cycle of Infection" *Journal of Virology* 78(21):11715-11725 (2004).

Flynn et al. "Antibody-Mediated Activation of Sindbis Virus[1]" *Virology* 166:82-90 (1988).

Foley et al. "Rhabdovirus-Based Vectors with Human Immunodeficiency Virus Type 1 (HIV-1) Envelopes Display HIV-1-Like Tropism and Target Human Dendritic Cells" *Journal of Virology* 76(1):19-31 (2002).

Fosmire et al. "Identification and Characterization of a Coronavirus Packaging Signal" *Journal of Virology* 66(6):3522-3530 (1992).

Frolov et al. "Alphavirus-based expression vectors: Stategies and applications" *Proc. Natl. Acad. Sci. USA* 93:11371-11377 (1996).

Frolov et al. "Comparison of the Amino Acid Sequences of Structural Proteins of Attenuated and Pathogenic Strains of Venezuelan Equine Encephalomyelitis Virus" *Doklady Biochemistry* 318:144-146 (1991).

Frolov et al. "Influence of Mutations in Genes of the Structural Proteins of Venezuelan Equine Encephalomyelitis on its Attenuation" *Doklady Biological Sciences* 326:466-469 (1992).

Frolov et al. "Recombinant VEE Virus Expresses HBsAg" *Proceedings, IXth International Congress of Virology* p. 67 (Aug. 8-13, 1993).

Frolov et al. "Recombinant Venezuelan Equine Encephalomyelitis Viruses Expressing HBsAg" *Papers of the Academy of Science* 332(6):789-791 (1993).

Frolov et al. "Translation of Sindbis Virus mRNA: Analysis of Sequences Downstream of the Initiating AUG Codon That Enhance Translation" *Journal of Virology* 70(2):1182-1190 (1996).

Frolov et al. "Translation of Sindbis Virus in RNA: Effects of Sequences Downstream of the Initiating Codon," *Journal of Virology* 68(12):8111-8117 (1994).

Frolova et al. "Packaging Signals in Alphaviruses," *Journal of Virology* 71(1):248-258 (Jan. 1997).

Fust, G. "Enhancing antibodies in HIV infection" *Parasitology* Supplemental 115:127-140 (1997).

Galili et al. "Natural Anti-Gal Antibody as a Universal Augmenter of Autologous Tumor Vaccine Immunogenicity" *Viewpoint Immunology Today* 18(6):281-285 (1997).

Gardner et al. "Infection of Human Dendritic Cells by a Sindbis Virus Replicon Vector is Determined by a Single Amino Acid Substitution in the E2 Glycoprotein" *Journal of Virology* 74(24):11849-11857 (2000).

Geigenmuller-Gnirke et al. "Complementation Between Sindbis Viral RNAs Produces Infectious Particles with a Bipartite Genome"

*Proceedings of the National Academy of Sciences of the United States of America* 88(8):3253-3257 (Apr. 15, 1991).
Glasgow et al. "A single amino acid change in the E2 spike protein of a virulent strain of Semliki Forest virus attenuates pathogenicity" *Journal of General Virology* 75:663-668 (1994).
Glasgow et al. "Two Mutations in the Envelope Glycoprotein E2 of Semliki Forest Virus Affecting the Maturation and Entry Patterns of the Virus Alter Pathogenicity for Mice" *Virology* 185:741-748 (1991).
Grieder et al. "Specific Restrictions in the Progression of Venezuelan Equine Encephalitis Virus-Induced Disease Resulting from Single Amino Acid Changes in the Glycoproteins" *Virology* 206:994-1006 (1995).
Guyre et al. "Increased potency of Fc-receptor-targeted antigens" *Cancer Immunology, Immunotherapy* 45:146-148 (1997).
Hahn et al. "Infectious Sindbis Virus Transient Expression Vectors for Studying Antigen Processing and Presentation" *Proc. Natl. Acad. Sci. USA* 89:2679-2683 (1992).
Harrington et al. "Systemic, Mucosal, and Heterotypic Immune Induction in Mice Inoculated with Venezuelan Equine Encephalitis Replicons Expressing Norwalk Virus-Like Particles" *Journal of Virology* 76(2):730-742 (2002).
Hawkes et al. "The Enhancement of Virus Infectivity by Antibody" *Virology* 33:250-261 (1967).
Heidner et al. "Lethality of PE2 Incorporation into Sindbis Virus Can Be Suppressed by Second-Site Mutations in E3 and E2" *Journal of Virology* 68(4):2683-2692 (1994).
Heise et al. "Adult Mouse Neurovirulence Determinants Within the Nonstructural Genes of the Sindbis-Group Alphavirus S.A.AR86" *American Society of Virology Meeting*, Colorado, Oral Presentation (Jul. 11, 2000).
Heise et al. "A Single Amino Acid Change in nsP1 Attenuates Neuroviolence of the Sindbis-Group Alphavirus S.A.AR86" *Journal of Virology* 74:9 (May 2000).
Heise et al. "Sindbis-Group Alphavirus Replication in Periosteum and Endosteum of Long Bones in Adult Mice" *Journal of Virology* 74(19):9294-9299 (Oct. 2000).
Heise et al. "The Role of Viral Nonstructural Genes in Neuroviruience of the Sindbis-Group Virus, S.A.AR86," *Keystone Symposia*, Taos, New Mexico, p. 306 (Feb. 2000).
Heufler et al. "Granulocyte/Macrophage Colony-Stimulating Factor and Interleukin 1 Mediate the Maturation of Murine Epidermal Langerhans Cells into Potent Immunostimulatory Dendritic Cells" *Journal of Experimental Medicine* 167:700-705 (1988).
Ikonomidis et al. "Influenza-Specific Immunity Induced by Recombinant Listeria Monocytogenes Vaccines" *Vaccines* 15(4):433-440 (1997).
Inada et al. "Association of Virulence of Murine Cytomegalovirus with Macrophage Susceptibility and with Virion-bound Non-neutralizing Antibody" *Journal of General Virology* 66:879-882 (1985).
Inada et al. "Enhancing Antibodies, Macrophages and Virulence in Mouse Cytomegalovirus Infection" *Journal of General Virology* 66:871-878 (1985).
Johnson et al. "Specific Targeting to CD4+ Cells of Recombinant Vesicular Stomatitis Viruses Encoding Human Immunodeficiency Virus Envelope Proteins" *Journal of Virology* 71(7):5060-5068 (1997).
Johnston et al. "Alphavirus Vectors: Biology and Vaccine Potential" Abstract ECEAR Meeting Edinburgh, Scotland (Jun. 23-26, 2001).
Jones et al. "Construction and Applications of Yellow Fever Virus Replicons" *Virology* 331:247-259 (2005).
Kawakami et al. "Section 3.1 Genes coding for Tumor Antigens Recognized by T Lymphocytes" *Biological Therapy of Cancer* 2nd Edition:53-63 J.B. Lippincott Company (1995).
Kinney et al. "Attenuation of Venezuelan Equine Encephalitis Virus Strain TC-83 Is Encoded by the 5'-Noncoding Region and the E2 Envelope Glycoprotein" *Journal of Virology* 67(3):1269-1277 (Mar. 1993).
Kinney et al. "The Full-Length Nucleotide Sequence of the Virulent Trinidad Donkey Strain of Venezuelan Equine Encephalitis Virus and Its Attenuated Vaccine Derivative, Strain TC-83" *Virology* 170:19-30 (1989).

Kotsopoulou et al. "A Rev-Independent Human Immunodeficiency Virus Type 1 (HIV-1)-Based Vector that Exploits a Codon-Optimized HIV-1 gag-pol Gene" *Journal of Virology* 74(10):4839-4852 (2000).
Leitner et al. "Alphavirus-based DNA Vaccine Breaks Immunological Tolerance by Activating Innate Antiviral Pathways" *Nature Medicine* 9(1):33-39 (2003).
Lemm et al. "Polypeptide requirements for assembly of functional Sindbis virus replication complexes: a model for the temporal regulation of minus- and plus-strand RNA synthesis" *The EmBO Journal* 13(12):2925-2934 (1994).
Liljestrom. "Alphavirus expression systems" *Current Opinion in Biotechnology*, 5(5):495-500 (Oct. 1994).
Liljestrom. "Alphavirus Vectors for Gene Delivery" OECD Documents, Gene Delivery Systems, 109-118 (1996).
Liljestrom et al. "A New Generation of Animal Cell Expression Vectors Based on the Semliki Forest Virus Replicon" *Bio/Technology* 9:1356-1361 (1991).
Linn et al. "Antibody-dependent enhancement and persistence in macrophages of an arbovirus associated with arthritis," *Journal of General Virology* 77:407-411 (1996).
London et al. "Infectious Enveloped RNA Virus Antigenic Chimeras," *Proc. Natl. Acad. Sci. USA* 89:207-211 (1992).
Lvov et al. "Karshi Virus, a New Flavivirus (Togaviridae) Isolated from Ornithodoros Papillipes (Birula, 1895) Ticks in Uzbek S.S.R." *Archives of Virology* 50:29-36 (1976).
MacDonald et al. "Role of Dendritic Cell Targeting in Venezuelan Equine Encephalitis Virus Pathogenesis" *Journal of Virology* 74(2):914-922 (2000).
Mady et al. "Neuraminidase augments Fcγ receptor II-mediated antibody-dependent enhancement of dengue virus infection" *Journal of General Virology* 74:839-844 (1993).
McKenna et al. "Covalently Linked Human Immunodeficiency Virus Type 1 gp120/gp41 Is Stably Anchored in Rhabdovirus Particles and Exposes Critical Neutralizing Epitopes" *Journal of Virology* 77(23):12782-12794 (2003).
McKenzie et al. "Biological advances and clinical application of Fc receptors for IgG" Current Opinion in Hematology 1:45-52 (1994).
McKnight. "The Human Rhinovirus Internal cis-acting Replication Element (cre) Exhibits Disparate Properties Among Serotypes" *Arch Virol* 148:2397-2418 (2003).
McKnight et al. "Deduced Consensus Sequence of Sindbis Virus Strain AR339: Mutations Contained in Laboratory Strains which Affect Cell Culture and in Vivo Phenotypes," *Journal of Virology*, 70(3) 1981-1989 (1996).
Morens. "Antibody-Dependent Enhancement of Infection and the Pathogenesis of Viral Disease" *Clinical Infectious Diseases* 19:500-512 (1994).
Morens et al. "Measurement of antibody-dependent infection enhancement of four dengue virus serotypes by monoclonal and polyclonal antibodies" *Journal of General Virology* 71:2909-2914 (1990).
Morgenstern et al. "Advanced mammalian gene transfer: high titre retroviral vectors with multiple drug selection markers and a complementary helper-free packaging cell line" *Nucleic Acids Research* 18(12):3587-3596 (1990).
Notification of Transmittal of the International Search Report and the Written Opinion of the International Searching Authority, or the Declaration, PCT/US06/05338 mailed May 22, 2007.
Ochiai et al. "Infection Enhancement of Influenza a NWS Virus in Primary Murine Macrophages by Anti-Hemagglutinin Monoclonal Antibody" *Journal of Medical Virology* 36:217-221 (1992).
Olsen. "A review of feline infectious peritonitis virus: molecular biology, immunopathogenesis, clinical aspects, and vaccination," *Veterinary Microbiology* 36:1-37 (1993).
Orkin et al. "Report and Recommendations of the Panel to Assess the NIH Investment in Research on Gene Therapy," *Current Science* 71(9):658-659 (1996).
O'Rourke et al. "Analysis of Gene Transfer and Expression in Skeletal Muscle Using Enhanced EIAV Lentivirus Vectors" *Molecular Therapy* 7(5):632-639 (2003).
Pan et al. "A Recombinant Listeria Monocytogenes Vaccine Expressing a Model Tumour Antigen Protects Mice Against Lethal Tumour Cell Challenge and Causes Regression of Established Tumors" *Nature Medicine* 1(5):471-477 (1995).

Pan et al. "Regression of Established Tumors in Mice Mediated by the Oral Administration of a Recombinant Listeria monocytogenes Vaccine[1]" *Cancer Research* 55:4776-4779 (1995).

Pastrana et al. "NHPV16 VLP Vaccine Induces Human Antibodies that Neutralize Divergent Variants of HPV16" *Virology* 279:361-369 (2001).

Peiris et al. "Antibody-dependent Enhancement of Plaque Formation on Cell Lines of Macrophage Origin—A Sensitive Assay for Antiviral Antibody" *Journal of General Virology* 57:119-125 (1981).

Peiris et al. "Monoclonal anti-FC receptor IgG blocks antibody enhancement of viral replication in macrophages." Nature 289(Jan. 15):189-191 (1981).

Perri et al. "An Alphavirus Replicon Particle Chimera Derived from Venezuelan Equine Encephalitis and Sindbis Viruses Is a Potent Gene-Based Vaccine Delivery Vector" *Journal of Virology* 77(19):10394-10403 (2003).

Polo et al. "Attenuating Mutations in Glycoproteins E1 and E2 of Sindbis Virus Produce a Highly Attenuated Strain When Combined in Vitro" *Journal of Virology* 64(9):4438-4444 (1990).

Polo et al. "Molecular Analysis of Sindbis Virus Pathogenesis in Neonatal Mice by Using Virus Recombinants Constructed In Vitro" *Journal of Virology* 62:2124-2133 (1988).

Porterfield. "Antibody-dependent Enhancement of Viral Infectivity," *Advances in Virus Research* 31:335-354 (1986).

"Program and Abstracts of the Joint Annual Meeting of the American Society of Tropical Medicine and Hygiene and the American Society of Parasitologists" Supplement to the American Journal of Tropical Medicine and Hygiene 49(3):194-196 (1993).

Publicover et al. "Characterization of Nonpathogenic, Live, Viral Vaccine Vectors Inducing Potent Cellular Immune Responses" *Journal of Virology* 78(17):9317-9324 (2004).

Pushko et al. "Recombinant RNA Replicons Derived from Attenuated Venezuelan Equine Encephalitis Virus Protect Guinea Pigs and Mice from Ebola Hemorrhagic Fever Virus" *Vaccine* 19:142-153 (2001).

Pushko et al. "Replicon-Helper Systems from Attenuated Venezuelan Equine Encephalitis Virus: Expression of Heterologous Genes in Vitro and Immunization Against Heterologous Pathogens in Vivo" *Virology* 239:389-401 (1997).

Raabe et al. "In Vitro Antibody-Dependent Enhancement Assays are Insensitive Indicators of in Vivo Vaccine Enhancement of Equine Infectious Anemia Virus," *Virology* 259:416-427 (1999).

Reddy et al. "Optimization of bovine coronavirus hemagglutinin-estrase glycoprotein expression in E3 deleted bovine adenovirus-3" *Virus Research* 70:65-73 (2000).

Restifo. "The new vaccines: building viruses that elicit antitumor immunity" *Current Opinion in Immunology* 9:658-663 (1997).

Restifo et al. "Transfectant Influenza A Viruses Are Effective Recombinant Immunogens in the Treatment of Experimental Cancer" *Virology* 249:89-97 (1998).

Rose et al. "Defining the Level of Human Immunodeficiency Virus Type 1 (HIV-1) Protease Activity Required for HIV-1 Particle Maturation and Infectivity" *Journal of Virology* 69(5):2751-2758 (1995).

Rosenberg. "A New Era for Cancer Immunotherapy Based on the Genes that Encode Cancer Antigens" *Immunity* 10:281-287 (1999).

Russell et al. "Sindbis Virus Mutations Which Coordinately Affect Glycoprotein Processing, Penetration, and Virulence in Mice" *Journal of Virology* 63(4):1619-1629 (1989).

Schlesinger. "Alphaviruses—vectors for the expression of heterologous genes" *TIBTECH* 11:18-22 (1993).

Schlesinger et al. "17D Yellow Fever Virus Infection of P388D$_1$ Cells Mediated by Monoclonal Antibodies: Properties of the Macrophage Fc Receptor" *Journal of General Virology* 64:1255-1262 (1983).

Schlesinger et al. "Recombination between Sindbis virus RNAs" *Archives of Virology* Suppl. 9:213-220 (1994).

Schoepp et al., "Directed Mutagenesis of a Sindbis Virus Pathogenesis Site" *Virology* 193: 149-159 (1993).

Schuler et al. "Dendritic Cells as Adjuvants for Immune-mediated Resistance to Tumors" *J. Exp. Med.* 186(8):1183-1187 (1997).

Schultz-Cherry et al. "Influenza Virus (A/HK/156/97) Hemagglutinin Expressed by an Alphavirus Replicon System Protects Chickens Against Lethal Infection with Hong Kong-Origin H5N1 Viruses" *Virology* 278:55-59 (2000).

Simpson et al., Complete Nucleotide Sequence and Full-Length cDNA Clone of S.A.AR86, a South African Alphavirus Related to Sindbis[1], *Virology* 222:464-469, Article No. 0445 (1996).

"Sindbis-Like Virus Isolate Girdwood S.A., Complete Genome," EMBL Database, Accession No. U38304, (Jan. 3, 1996).

"Sindbis Virus (HRSP and Wild-Type Strains), Complete Genome," EMBL Database, Accession Nos. J02363, 02364, J02366, J02367, and V00073, (Jul. 3, 1991).

Sjoberg et al. "A Significantly Improved Semliki Forest Virus Expression System Based on Translation Enhancer Segments from the Viral Capsid Gene" *Bio/Technology* 12:1127-1131 (1994).

Soneoka et al. "A Transient Three-Plasmid Expression System for the Production of High Titer Retroviral Vectors" *Nucleic Acids Research* 23(4):628-633 (1995).

Song et al. "Antigen presentation in retroviral vector-mediated gene transfer in vivo" *Proc. Natl. Acad. Sci. USA* 94:1943-1948 (1997).

Song et al. "Dendritic Cells Genetically Modified with an Adenovirus Vector Encoding the cDNA for a Model Antigen Induce Protective and Therapeutic Antitumor Immunity" *J. Exp. Med.* 186(8):1247-1256 (1997).

Specht et al. "Dendritic Cells Retrovirally Transduced with a Model Antigen Gene Are Therapeutically Effective against Established Pulmonary Metastases" *J. Exp. Med.* 186(8):1213-1221 (1997).

Steinman. "The Dendritic Cell System and its Role in Immunogenicity" *Annual Review of Immunology* 9:271-296 (1991).

Storkus et al. "Section 3.2 Tumor Antigens Recognized by Immune Cells" *Biologic Therapy of Cancer* Second Edition, J.B. Lippincott Company, 1995 pp. 64-77.

Strauss et al. "The Alphaviruses: Gene Expression, Replication, and Evolution" *Microbiological Reviews* 58(3):491-562 (1994).

Suomalainen et al. "Spike Protein-Nucleocapsid Interactions Drive the Budding of Alphaviruses" *Journal of Virology* 66(8):4737-4747 (1992).

Supplementary European Search Report corresponding EP Application No. EP 06 84 4071 mailed Jan. 22, 2009, 11 pages.

Vennema et al. "Early Death after Feline Infectious Peritonitis Virus Challenge due to Recombinant Vaccinia Virus Immunization" *Journal of Virology* 64(3):1407-1409 (1990).

Vrati et al. "Ross River Virus Mutant with a Deletion in the E2 Gene: Properties of the Virion, Virus-Specific Macromolecule Synthesis, and Attenuation of Virulence for Mice" *Virology* 151:222-232 (1986).

Wang et al. "Active Immunotherapy of Cancer with a Nonreplicating Recombinant Fowlpox Virus Encoding a Model Tumor Associated Antigen" The Journal of Immunology 154:4685-4692 (1995).

Weiss et al. "Recombination Between Sindbis Virus RNAs" *Journal of Virology* 65(8):4017-4025 (1991).

West et al. "Genetic Analysis of Cell Targeting and Immunogenicity of VEE Vectors" Abstract AIDS Vaccine 2001 Meeting Philadelphia, PA (Sep. 2001).

Wu et al. "Tolerance to a Dominant T Cell Epitope in the Acetylcholine Receptor Molecule Induces Epitope Spread and Suppresses Murine Myasthenia Gravis[1]" *The Journal of Immunology* 159(6):3016-3023 (1997).

Xiong et al. "Sindbis Virus: An Efficient, Broad Host Range Vector for Gene Expression in Animal Cells" *Science* 243(4895):1188-1191 (1989).

Yao et al. "Antibody-dependent enhancement of hantavirus infection in macrophage cell lines," *Archives of Virology* 122:107-118 (1992).

* cited by examiner

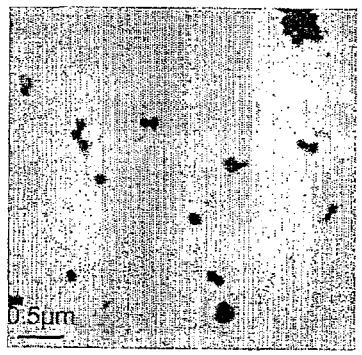 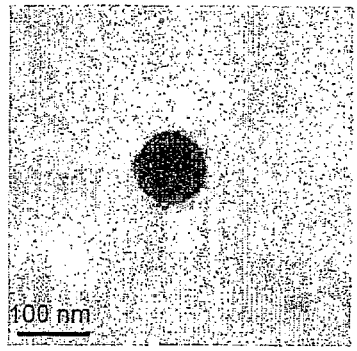
FIG. 2C  FIG. 2D
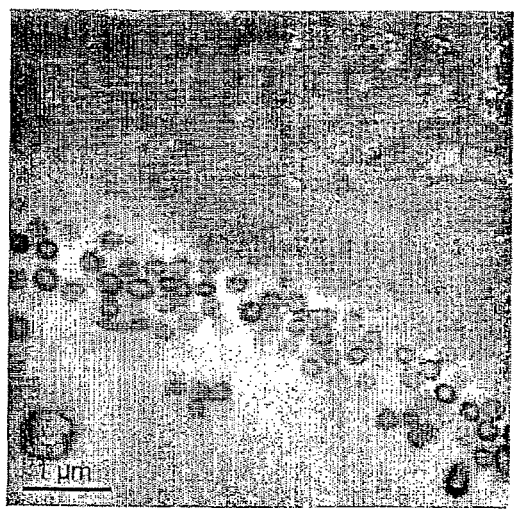
FIG. 2E

LIVE VIRUS VACCINES

CROSS-REFERENCE TO RELATED APPLICATIONS

This application is a 35 U.S.C. §371 national phase application of International Application Ser. No. PCT/US2006/005338 filed Feb. 15, 2006, which claims priority to U.S. Provisional Application No. 60/653,255, filed Feb. 15, 2005, the disclosures of each of which are incorporated herein by reference in their entireties.

RELATED APPLICATION INFORMATION

This application claims the benefit of U.S. provisional application Ser. No. 60/653,255, filed 15 Feb. 2005, the disclosure of which is incorporated herein by reference in its entirety.

FIELD OF THE INVENTION

The present invention relates to live virus vaccines, in particular, live self-propagating virus vaccines.

BACKGROUND OF THE INVENTION

Vaccination against disease is effected by inducing a protective immune response to a pathogenic organism without causing disease. One of the most efficient means of accomplishing this for pathogenic viruses is to modify the genome of the virus so that it can grow in a human or other animal with reduced disease symptoms, but nonetheless induce an immune response, which will protect the individual from infection by the actual pathogen. Examples of such live attenuated virus vaccines include those for polio, measles, mumps, rubella, chicken pox and smallpox. In the past, however, such vaccines have been derived empirically from the pathogenic virus. It would be desirable to have a method of engineering safer life viruses directly.

SUMMARY OF THE INVENTION

As one aspect, the present invention provides a self-propagating chimeric viral vector comprising a modified genome of an RNA virus, said modified genome comprising:
(a) protein coding sequences and cis-acting sequences from the RNA virus sufficient for replication of the modified RNA virus genome; and
(b) structural protein coding sequences from a second virus sufficient to form a virion, wherein the second virus is a retrovirus.

As a further aspect, the invention provides a self-propagating chimeric viral vector comprising a modified alphavirus, rhabdovirus or coronavirus genome, the modified genome comprising:
(a) protein coding sequences and cis-acting sequences from the alphavirus or rhabdovirus sufficient for replication of the modified alphavirus genome; and
(b) structural protein coding sequences from a second virus sufficient to form a virion.

As still another aspect, the invention provides a self-propagating chimeric viral vector comprising a modified alphavirus genome, the modified genome comprising:
(a) protein coding sequences and cis-acting sequences from the alphavirus sufficient for replication of the modified alphavirus genome; and
(b) structural protein coding sequences from a retrovirus sufficient to form a virion.

As another aspect, the invention provides a self-propagating chimeric viral vector comprising a modified rhabdovirus genome, the modified genome comprising:
(a) protein coding sequences and cis-acting sequences from the rhabdovirus sufficient for replication of the modified rhabdovirus genome; and
(b) structural protein coding sequences from a retrovirus sufficient to form a virion.

As yet a further aspect, the invention provides a self-propagating chimeric viral vector comprising a modified coronavirus genome, the modified genome comprising:
(a) protein coding sequences and cis-acting sequences from the coronavirus sufficient for replication of the modified coronavirus genome; and
(b) structural protein coding sequences from a retrovirus sufficient to form a virion.

The invention further encompasses a self-propagating chimeric virus particle comprising a chimeric viral vector of the invention packaged in a virion.

Also provided are nucleic acids encoding the chimeric viral vectors of the invention, and virus particles comprising the nucleic acids.

As a further aspect, the invention provides a pharmaceutical formulation comprising a viral vector, virus particle, or nucleic acid of the invention in a pharmaceutically acceptable carrier.

As still another aspect, the invention provides a method of making a chimeric virus particle, comprising introducing a viral vector, virus particle, or nucleic acid of the invention into a cell under conditions sufficient for chimeric virus particles to be produced, wherein the chimeric virus particles each comprise the chimeric viral vector packaged within virion structural proteins from the second virus.

The invention further provides a method of producing an immune response in a subject, the method comprising:
administering a viral vector, virus particle, or nucleic acid, or pharmaceutical formulation of the invention to a subject in an immunogenically effective amount so that an immune response is produced in the subject.

Also provided is the use of a viral vector, virus particle, nucleic acid, or pharmaceutical formulation of the invention for producing an immune response in a subject.

These and other aspects of the invention are set forth in more detail in the description of the invention below.

BRIEF DESCRIPTION OF THE DRAWINGS

FIGS. 2A-E show the assembly and release of immature Gag particles by expressing Gag from VEE replicon RNA in cells. FIG. 2A depicts the construct containing full-length SIVsmH4 Gag protein. FIG. 2B is a schematic of VEE replicon packaging of the p55 Gag protein. FIGS. 2C and 2D show Gag-VRP released into the cell culture supernatants. Particles were concentrated by pelleting through 20% sucrose and an aliquot placed onto a nickel grid. Particles were fixed in 2.5% glutaraldehyde, stained with 2% uranyl acetate and visualized by transmission electron microscopy (TEM). FIG. 2C, 25000× magnification. FIG. 2D, 200000× magnification.

FIG. 2E shows immunogold labeling of Gag particles. Cells were fixed in 2% paraformaldehyde, 0.5% glutaraldehyde. Vero Gag+ was additionally postfixed in osmium tetroxide. Cells were embedded in LR White resin, sectioned parallel to the substrate at 80 nm, labeled using a 1:100 dilution of a monoclonal antibody to Matrix protein (KK59-NIH AIDs Repository Catalog #2320) as a primary antibody, followed by a 1:50 dilution of a goat anti-mouse IgG secondary antibody conjugated to a 10 nm colloidal gold particle. Immunogold labeling was followed by post-staining in uranyl acetate and lead citrate. Photograph is of 16000× magnification.

FIG. 3A shows a schematic of replicon RNAs detected by RT-PCR. FIG. 3B shows RT-PCR analysis of concentrated Gag particles from VRP-infected Vero cells with or without GagA control RNA. Gag particles were subjected to nuclease treatment or left untreated as indicated. After nuclease treatment, viral RNA was extracted and encapsidated RNA was detected by RT-PCR. NT, nuclease-treated particles. UnT, untreated particles. GagA, Gag replicon with deletion in NSP4.

FIG. 4A is a schematic of VEE replicon packaging of the gp160 Env protein. FIG. 4B shows syncytium formation in 3T3-CD4-CCR5 cell monolayers infected with Env (gp160)-expressing VRP.

FIG. 6A shows a ψ Gag particle released into the cell culture supernatants. FIG. 6B is a western blot showing shows Gag expression from Gag and ψ Gag replicons. Vero cells were electroporated with either Gag replicon RNA or Gag replicon RNA containing a putative SIV ψ sequence (ψGag). After 20 hours, cell culture supernatants were concentrated by pelleting through 20% sucrose and the cells were lysed with NP-40 lysis buffer. Aliquots were separated by 10% SDS-PAGE, transferred to a PVDF membrane and probed with α-SHIV monkey sera.

FIG. 8A depicts the template for the ψ riboprobe. FIG. 8B shows the detection of Gag in cells lysed with NP-40 lysis buffer and immunoprecipitated with α-SHIV monkey sera. FIG. 8C shows Gag immunoprecipitated cell lysates separated by 10% SDS-PAGE, blotted to a nitrocellulose membrane, and probed with a $^{32}$P labeled RNA probe containing a putative ψ sequence.

FIG. 10A is a schematic showing the construction of SHIV89.6P GagEnv and EnvGag replicons. FIG. 10B depicts the production of chimeric GagEnv particles. FIG. 10C is a western blot showing expression of Gag and Env from SHIV89.6P GagEnv and EnvGag double promoter replicons. Vero cells were mock-electroporated or electroporated with either GagEnv or EnvGag replicon RNA. After 24 hours, cell culture supernatants were concentrated by pelleting through 20% sucrose and the cells were lysed with NP-40 lysis buffer. Aliquots were either left untreated or treated with PNGase F, separated by 10% SDS-PAGE, transferred to a PVDF membrane, and probed with α-SHIV monkey sera. FIG. 10D shows immunoprecipitated Env protein expressed by Env-VRP. Protein in Lane 4 was immunoprecipitated with α-gp120 antibody b12. FIG. 10E shows immunoprecipitation of chimeric GagEnv and EnvGag particles with α-gp120 antibody and detection of co-immunoprecipitated Gag by probing the western blot with α-Gag antibody.

FIGS. 11A, 11B and 11E show the cells stained with Nomarski stain, whereas FIGS. 11C, 11D, and 11F show DAPI staining.

FIG. 12A) or with GagEnv (FIG. 12B) and EnvGag (FIGS. 12C and 12D) VLPs. Twelve hpi, the cells were fixed, stained with α-SHIV Env mouse sera, and viewed via phase contrast (FIG. 12C) or fluorescence (FIGS. 12A, 12B, and 12D) microscopy.

FIG. 13A shows images of 3T3-CD4-CCR5 cells mock-infected or infected with Env VRP (100 IU), GagEnv particles or EnvGag particles. At 18 hpi, cells were fixed in 2% PFA, permeabilized, and the expression of VEE replicon RNA was visualized in syncytia by indirect immunofluorescence (IFA) staining with antiserum from mice immunized with either Gag-VRP or with empty-VRP+ovalbumin antigen. Lower panels show IFA staining, whereas upper panels are phase-contrast images of the lower panels.

FIG. 14A depicts a VEE capsid protein fused in frame to the Gag open reading frame.

FIG. 15A shows the expression of SIVsmH4. Vero cells were mock-transfected or transfected by electroporation with replicon RNA expressing SIVsmH4 Gag or Gag-Pro. Nineteen hours post-electroporation, the cells were lysed with NP-40 lysis buffer and clarified. The cell culture supernatants were clarified and concentrated through 20% OPTIPREP® and the resulting pellets were resuspended in PBS. A portion of the cell lysates (CL) and concentrated supernatants (CS) were separated on a 15% SDS-PAGE gel, transferred to a PVDF membrane and probed with α-SIV Gag monoclonal antibody kk64. Cell lysate from Vero cells infected with SHIV89.6P Gag VRP served as a marker for p55 Gag migration.

DETAILED DESCRIPTION OF THE INVENTION

Figure 1:
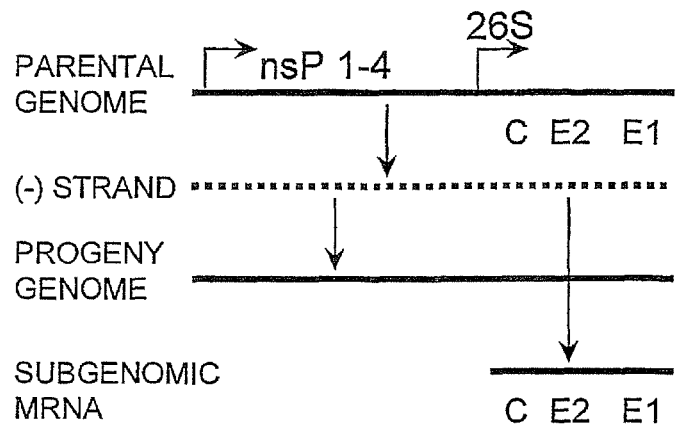
FIG. 1 depicts RNA replication of Venezuelan equine encephalitis (VEE). VEE has a (+)ssRNA genome encoding capsid protein (C), E1 glycoprotein, and E2 glycoprotein as well as non-structural proteins, nsP1-4. The parental genome is replicated via (−)strand synthesis, which subsequently serves as a template for generation of the progeny genome as well as the 26S subgenomic mRNA encoding C, E1, and E2.

The present invention provides a method to engineer safer live vaccines. To describe it in the simplest terms, a virus includes two components: a genome (DNA or RNA) which contains the genetic information required for its own reproduction as well as the information required for synthesis of the structural proteins which surround the genome in the virion (i.e., infectious virus particle) itself. These two components, the genome and the structural proteins, are assembled into virions in the late stages of infection in a cell. Protective immune responses are raised primarily against the structural proteins.

The present invention differs from prior approaches in that the vaccine virus is a novel self-replicating (i.e., genomic replication) and self-propagating (i.e., production of new virus particles) entity. The chimeric virus comprises a modified genome from a "carrier" virus comprising coding sequences for proteins such as replicase and cis-acting sequences from the carrier virus sufficient for nucleic acid replication and packaging. The modified genome further comprises the coding sequences for structural proteins from a second virus, which can be a pathogenic virus, sufficient to form a virion. These two components, the modified genome and structural proteins are assembled to generate a new viral entity—a live, self-propagating chimeric virus comprising a modified genome from the carrier virus and structural proteins from the second virus.

In particular embodiments, the resulting vaccine virus presents the antigenic structure of the second virus but contains the modified genome of the carrier virus. Thus, replication of the vaccine virus in the body magnifies the vaccine effect over that which would be achieved by simply inactivating virions and inoculating them as a vaccine. The receptor recognition properties of the vaccine virus are generally those of the second virus from which the structural proteins were derived (unless the structural proteins are further modified to present heterologous targeting peptides). The replicative properties are generally those of the modified carrier virus genome (unless additional modifications are introduced into the viral genome).

In other embodiments, the vaccine virus presents an immunogen on the surface of the virus that is expressed as part of a fusion protein with all or part of a structural protein from the second virus (for example, a capsid or envelope protein). The immunogen can be any immunogen of interest, e.g., a cancer immunogen, an immunogen from an infectious organism or another virus, an allergen, a transplant immunogen, and the like. Immunogens are discussed in more detail hereinbelow. As one illustration, the virion can comprise an envelope protein from the second virus which is a fusion protein comprising a capsid interacting region (e.g., intracellular region of the envelope protein) from the second virus that is fused to a heterologous immunogen, for example, all or a portion of an envelope glycoprotein from another virus or any other immunogen of interest. In this way, the virion can assemble because the fusion envelope protein can interact with the capsid protein from the second virus, put present an antigen(s) from a different source on the virion surface.

As another example, the vaccine virus can present an immunogenic peptide or protein that is expressed from a heterologous nucleic acid, which is not expressed as part of a structural protein from the second virus (i.e., is expressed independently of a structural protein).

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

All publications, patent applications, patents, and other references mentioned herein or in attachments hereto are incorporated by reference in their entirety.

As used herein, a "chimeric virus vector" comprises, consists essentially of, or consists of a modified carrier RNA virus genome, optionally within a chimeric virus particle. In this context, the term "consists essentially of" means that the chimeric virus vector does not comprise any elements beyond the modified carrier virus genome that materially affect the function of the chimeric viral vector. The chimeric viral vector can further be incorporated into a delivery vector, such as a viral delivery vector, plasmid, or a liposomal delivery vector or any other suitable delivery vector known in the art, and a chimeric virus particle can be produced from the chimeric viral vector upon introduction into a cell or following administration in vivo to a subject.

Accordingly, in representative embodiments, the invention provides a self-propagating chimeric viral vector comprising a modified genome of an RNA virus, the modified genome comprising: (a) protein coding sequences and cis-acting sequences (e.g., the 5' and/or 3' untranslated regions of the genome) from the RNA virus sufficient for replication of the modified RNA virus genome; and (b) structural protein coding sequences from a second virus sufficient to form a virion, wherein the second virus is a retrovirus. The viral vector is "self-propagating" in that it can self-replicate the modified genomic nucleic acid, produce the encoded structural proteins and assemble new chimeric virus particles in a permissive cell in the absence of a helper construct. Thus, as used herein, the term "propagation" refers to a productive viral infection wherein the viral genome is replicated and packaged to produce new virions, which typically can spread by infection of cells beyond the initially infected cell.

According to this embodiment of the invention, the carrier virus can be any RNA virus including single- and double-stranded and positive- and negative-stranded viruses, as well as integrating and non-integrating viruses. In representative embodiments, the carrier virus is a non-integrating RNA virus (including a virus that is modified to be non-integrating). The carrier virus can be a pathogenic or non-pathogenic virus, but typically the modified genomic nucleic acid from the carrier RNA virus will not itself cause pathogenesis nor will it be pathogenic in conjunction with the included components of the second virus that provides the structural proteins. In representative embodiments, the carrier virus is an alphavirus, a paramyxovirus, a rhabdovirus, a coronavirus, a picornavirus, or a myxovirus.

In other representative embodiments, the invention provides a self-propagating chimeric viral vector comprising a modified alphavirus genome, the modified genome comprising: (a) protein coding sequences and cis-acting sequences (e.g., the 5' and/or 3' noncoding sequences at the ends of the viral genome) from the alphavirus sufficient for replication of the modified alphavirus genome; and (b) structural protein coding sequences from a second virus sufficient to form a virion.

In further embodiments, the invention provides a self-propagating chimeric viral vector comprising a modified rhabdovirus genome, the modified genome comprising: (a) protein coding sequences and cis-acting sequences (e.g., the 5' and/or 3' noncoding sequences at the ends of the viral genome) from the rhabdovirus sufficient for replication of the modified rhabdovirus genome; and (b) structural protein coding sequences from a second virus sufficient to form a virion.

In yet other embodiments, the invention provides a self-propagating chimeric viral vector comprising a modified coronavirus genome, the modified genome comprising: (a) protein coding sequences and cis-acting sequences (e.g., the 5' and/or 3' noncoding sequences at the ends of the viral genome) from the coronavirus sufficient for replication of the modified coronavirus genome; and (b) structural protein coding sequences from a second virus sufficient to form a virion.

According to the present invention, the carrier virus (i.e., the virus from which the modified RNA genome is derived) and the second virus are not from the same virus genus. Thus, the chimeric viral vectors and chimeric virus particles of the invention exclude chimeric alphaviruses, chimeric retroviruses, chimeric paramyxoviruses, and the like.

Alphavirus particles comprise the alphavirus structural proteins assembled to form an enveloped nucleocapsid structure. As known in the art, alphavirus structural subunits consisting of a single viral protein, capsid (C), associate with themselves and with the RNA genome to form the icosahedral nucleocapsid, which is then surrounded by a lipid envelope covered with a regular array of transmembranal protein spikes, each of which consists of a heterodimeric complex of two glycoproteins, E1 and E2 (See Paredes et al., (1993) *Proc. Natl. Acad. Sci. USA* 90, 9095-99; Paredes et al., (1993) *Virology* 187, 324-32; Pedersen et al., (1974) *J. Virol.* 14:40). The wild-type alphavirus genome is a single-stranded, messenger-sense RNA, modified at the 5'-end with a methylated cap, and at the 3'-end with a variable-length poly (A) tract. The viral genome is divided into two regions: the first encodes the nonstructural or replicase proteins (nsP1-nsP4) and the second encodes the viral structural proteins (Strauss and Strauss, *Microbiological Rev.* (1994) 58:491-562).

The term "alphavirus" has its conventional meaning in the art, and includes Eastern Equine Encephalitis virus (EEE), Venezuelan Equine Encephalitis virus (VEE), Everglades virus, Mucambo virus, Pixuna virus, Western Encephalitis virus (WEE), Sindbis virus, South African Arbovirus No. 86 (S.A.AR86), Girdwood S.A. virus, Ockelbo virus, Semliki Forest virus, Middelburg virus, Chikungunya virus, O'Nyong-Nyong virus, Ross River virus, Barmah Forest virus, Getah virus, Sagiyama virus, Bebaru virus, Mayaro virus, Una virus, Aura virus, Whataroa virus, Babanki virus, Kyzlagach virus, Highlands J virus, Fort Morgan virus, Ndumu virus, Buggy Creek virus, and any other virus classified by the International Committee on Taxonomy of Viruses (ICTV) as an alphavirus.

Exemplary alphaviruses for use in the present invention are Sindbis virus (e.g., strain TR339), VEE virus, S.A.AR86 virus, Girdwood S.A. virus, and Ockelbo virus. The complete genomic sequences, as well as the sequences of the various structural and non-structural proteins are known in the art for numerous alphaviruses and include without limitation: Sindbis virus genomic sequence (GenBank Accession Nos. J02363, NCBI Accession No. NC_001547), S.A.AR86 genomic sequence (GenBank Accession No. U38305), VEE genomic sequence (GenBank Accession No. L04653, NCBI Accession No. NC_001449), Girdwood S.A genomic sequence (GenBank Accession No. U38304), Semliki Forest virus genomic sequence (GenBank Accession No. X04129, NCBI Accession No. NC_003215), and the TR339 genomic sequence (Klimstra et al., (1988) *J. Virol.* 72:7357; McKnight et al., (1996) *J. Virol.* 70:1981).

In particular embodiments, when functioning as the carrier virus, the modified alphavirus genome comprises coding sequences for the nsp1, nsp2, nsp3 and nsp4 proteins and, optionally, the alphavirus 5' and/or 3' non-coding sequences (which contain cis-acting elements including CSEs (Conserved Sequence Elements). The modified alphavirus genome can further comprise an alphavirus packaging sequence (generally located in the nonstructural genes).

Paramyxoviruses are enveloped negative-stranded RNA viruses. The virus contains a lipid bilayer envelope derived from the plasma membrane of the host cell in which the virus was produced. Glycoprotein spikes are inserted into the envelope. Inside the membrane is the nucleocapsid core, which contains the 15 to 19 kb single-stranded RNA genome. The predominant structural proteins are the F (fusion) and the HN (hemagglutinin-neuraminidase) glycoproteins, the matrix (M) protein; and the N (nucleocapsid) protein and P (nucleocapsid phosphoprotein). The viral polymerase is formed by a complex of P (phosphoprotein) and L (large) proteins. In addition to the P phosphoprotein, a number of other nonstructural proteins are encoded by the P gene, which have been designated as C, C', D, I, V, W, X, Y1, Y2 and Z. The cis-acting sequences in the 5' and 3' untranslated ends of the genome are also involved in replication. The Paramyxovirus family includes the *Respirovirus* genus (e.g., human parainfluenza virus 1, bovine parainfluenza virus 3, human parainfluenza virus 3, Sendai virus, and simian parainfluenza virus 10), *Rubulavirus* genus (e.g., Human parainfluenza virus 2, Human parainfluenza virus 4A and 4B, Mapuera virus, Mumps virus, Porcine rubulavirus, Simian parainfluenza virus 5, Simian parainfluenza virus 41), *Morbillivirus* genus (e.g., Canine distemper virus, Cetacean Morbillivirus, Measles virus, dolphin morbillivirus, Peste-des-petits-ruminants virus, Phocine distemper virus, Rinderpest virus), Henipavirus genus (e.g., Hendravirus, Nipahvirus), Avulavirus genus (e.g., Newcastle disease virus, Avian paramyxoviruses 1-9), TPMV-like viruses (e.g., Tupaia virus), *Pneumovirus* genus (e.g., Bovine respiratory syncytial virus, Human respiratory syncytial virus, Murine pneumonia virus), and the *Metapneumovirus* genus (e.g., Turkey rhinotracheitis virus), and any other virus classified by the ICTV as a paramyxovirus.

In particular embodiments, when functioning as the carrier virus, the modified paramyxovirus genome comprises coding sequences for the P and L proteins and, optionally, the N protein. The modified paramyxovirus genome can also comprise the 5' and/or 3' terminal untranslated sequences. In other embodiments, the modified paramyxovirus genome comprises the P gene and an L gene and, optionally, the N gene and/or the 5' and/or 3' terminal untranslated sequences. The modified paramyxovirus genome can further comprise a paramyxovirus packaging sequence.

Rhabdoviridae are enveloped, negative-strand RNA viruses. The rhabodvirus virion comprises an external membrane derived from the cell in which the virus was produced and an internal ribonucleoprotein core comprising the genomic RNA and N (nucleocapsid) protein. The viral glycoprotein (G) spans the membrane and forms an array of trimeric spikes. About 1800 viral matrix (M) protein molecules are inside the viral envelope and form a layer between the membrane and the nucleocapsid core. The nonstructural proteins include the L (large) and P (phosphoprotein) proteins, which form the viral transcriptase-replicase complex. There are cis-acting elements, including the packaging signal, located in the 5' (e.g., 5' terminal 36 nucleotides) and 3' (e.g., 3'-terminal 51 nucleotides) ends of the genome. The Rhabdoviridae family includes the *Vesiculovirus* genus (e.g., Carajas virus, Chandipura virus, Cocal virus, Isfahan virus, Maraba virus, Piry virus, Vesicular stomatitis virus [VSV, including the Alagoas, Indiana, and New Jersey strains, and the like]), *Lyssavirus* genus (e.g., Australian bat lyssavirus, Duvenhage virus, European bat lyssaviruses 1-2, Lagos bat virus, Mokola virus, Rabies virus), *Ephemerovirus* genus (e.g., Adelaide River virus, Berrimah virus, Bovine ephemeral fever virus), and the *Novirhabdovirus* genus (e.g., Hirame rhabdovirus, Infectious hematopoietic necrosis virus, Viral hemorrhagic septicemia virus, Snakehead rhabdovirus); and any other virus classified by the ICTV as a rhabdovirus.

In particular embodiments, when functioning as the carrier virus, the modified rhabdovirus genome comprises coding sequences for the L and P proteins and, optionally, the N protein. The modified rhabdovirus genome can further comprise the 5' terminal cis-acting (e.g., 5' terminal 36 nucleotides) and/or the 3' terminal cis-acting (e.g., 3'-terminal 51 nucleotides) sequences, which includes the rhabdovirus packaging sequence.

The term "myxovirus" (also known as "orthomyxovirus") has its conventional meaning in the art, and includes influenza A virus, influenza B virus, influenza C virus, thogotovirus and any other virus classified by the ICTV as a myxovirus. Myxoviruses are enveloped viruses with a segmented single-stranded RNA genome, which is deemed to be negative-stranded because the viral mRNA are transcribed from the viral RNA segments. Myxoviruses contain a ribonucleoprotein core of RNA and NP (nucleocapsid protein), which is surrounded by the $M_1$ (matrix protein) layer, which also provides stability to the membrane. Glycoprotein spikes of HA (hemagglutinin) and NA (neuraminidase) radiate outward from the lipid envelope. Integral membrane proteins $M_2$, NB and CM2 are also present in influenza A, B and C virions, but at much lower abundance than HA or NA. The viral polymerase is made up of the P proteins, for example, the PB1, PB2 and PA proteins of influenza A virus, and the homologous proteins in influenza B and C.

In particular embodiments, when functioning as the carrier virus, the modified myxovirus genome comprises coding sequences for the P proteins and, optionally, the NP protein. The modified myxovirus genome can further comprise a myxovirus packaging sequence. In other embodiments, the modified myxovirus genome comprises the 5' and/or 3' non-translated ends of the genome.

Coronaviruses, members of the order Nidovirus, contain the largest single-stranded, positive-polarity RNA genome in nature and are divided into three main serogroups: group I: transmissible gastroenteritis virus (TGEV) and human coronavirus 229E (HCV-229E), group II: mouse hepatitis virus (MHV) and bovine coronavirus (BoCV), and group III: infectious bronchitis virus (IBV). Inside the coronavirus virion is a single-stranded, negative-sense genomic RNA of about 28 to 32 kb in size. The genomic RNA associates with the N (nucleocapsid phosphoprotein). The virion core is made up of the M (membrane) glycoprotein. Surface glycoprotein spikes radiate from the lipoprotein envelope: the S (spike) glycoprotein is found on all coronaviruses and the HE (hemagglutinin-esterase) glycoprotein, which is present in only some coronaviruses. The M glycoprotein is part of the envelope as well as the core, and spans the lipid bilayer three times. The E (envelope) protein is also present in the envelope, but in much lower abundance that the other viral envelope proteins. The polymerase precursor polyproteins 1a and 1b give rise to the viral polymerase. The 3' end of orf1b contains cis-acting sequences including the packaging signal. The term "coronavirus" as used herein has its conventional meaning in the art and refers to a genus in the family Coronaviridae, which family is in turn classified within the order Nidovirales. The coronaviruses are large, enveloped, positive-stranded RNA viruses. Coronaviruses encompass SARS coronavirus, transmissible gastroenteritis virus (TGEV), human respiratory coronavirus, porcine respiratory coronavirus, canine coronavirus, feline enteric coronavirus, feline infectious peritonitis virus, rabbit coronavirus, murine hepatitis virus, sialodacryoadenitis virus, porcine hemagglutinating encephalomyelitis virus, bovine coronavirus, avian infectious bronchitis virus, and turkey coronavirus, and any other virus classified by the ICTV as a coronavirus.

In particular embodiments, when functioning as the carrier virus, the modified coronavirus genome comprises coding sequences for the polymerase precursor polyprotein 1a and 1b and, optionally, the N protein. The modified coronavirus genome can further comprise the 5' and/or 3' untranslated ends of the genome and/or a coronavirus packaging sequence (e.g., the 3' end of orf1b).

The picornaviruses are non-enveloped viruses with a single-stranded RNA genome of positive polarity. The picornavirus genome encodes a single polyprotein, which is processed by viral proteases (e.g., $L^{pro}$, $2A^{pro}$, and $3C^{pro}$). Most of the proteins encoded by the P2 and P3 regions of the genome are involved in RNA synthesis. The $3D^{pol}$ protein is the viral polymerase, and accessory proteins include 2A, 2B, 2C and 3AB proteins. The 5' and 3' ends untranslated ends of the genome contain cis-acting elements involved in viral replication. The capsids of picornaviruses are generally composed of four structural proteins: VP1, VP2, VP3 and VP4. The exception is the parchoviruses, which contain only three capsid proteins: VP1, VP2 and VP0 (the uncleaved precursor to Vp2+VP4). The term "picornavirus" as used herein has its conventional meaning in the art and refers to viruses in the family Picornaviridae and includes viruses in the genera Enterovirus (e.g., bovine enterovirus 1, bovine enterovirus 2, human enterovirus A [human coxsackievirus A 2, 3, 5, 7, 8, 10, 12, 14 and 16 and human enterovirus 71 strains], human enterovirus B [human coxsackievirus A 9 and B 1, 2, 3, 4, 5, 6 strains and human echovirus strains], human enterovirus C virus [human coxsachievirus A 1, 11, 13, 15, 17, 18, 19, 20, 21, 22, 24 strains], human enterovirus D [human enterovirus 68 and 70 strains], human enterovirus E, polioviruses [human poliovirus strains], porcine enterovirus A [porcine enterovirus 8], porcine enterovirus B [porcine enterovirus 9 and 10 strains], and simian enterovirus), Rhinovirus (e.g., human rhinovirus A, human rhinovirus B, and bovine rhinovirus), Cardiovirus (e.g., encephalomyocarditis virus [Mengovirus, Columbia SK virus and Maus Elberfield virus strains], and theilovirus [Theiler's murine encephalomyelitis virus, Vilyuisk human encephalomyelitis virus and rat encephalomyelitis virus]), Aphthovirus (e.g., equine rhinitis A virus and foot-and-mouth disease virus), Hepatovirus (e.g., hepatitis A virus, simian hepatitis A virus, and avian encephalomyelitis-like virus), Parechovirus (e.g., human parechovirus [human parechovirus type 1 strain], human parechovirus type 2, and Ljungan virus), Erbovirus (e.g., equine rhinitis V virus), Kouvirus (e.g., aichi virus) and Teschovirus (e.g., porcine teschovirus 1, porcine teschovirus 2, porcine teschovirus 3, porcine teschovirus 4, porcine teschovirus 5, porcine teschovirus 6, porcine teschovirus 7, porcine teschovirus 8, porcine teschovirus 9, porcine teschovirus 10, porcine teschovirus 1, porcine teschovirus 12, porcine teschovirus 13), acid-stable equine picornaviruses, avian entero-like virus 2, avian entero-like virus 3, avian entero-like virus 4, avian nephritis virus 1, avian nephritis virus 2, avian nephritis virus 3, Barramundi virus-1+, Cockatoo entero-like virus, duck hepatitis virus 1, duck hepatitis virus 3, equine rhinovirus 3, guineafowl transmissible enteritis virus, Harbour seal picorna-like virus, seabass virus-1+, Sikhote-Alyn virus, smelt virus-1+, smelt virus-2+, Syr-Daria valley fever virus, taura syndrome virus of marine penaeid shrimp, turbot virus-1, turkey entero-like virus, turkey pseudo enterovirus 1, and turkey pseudo enterovirus 2, as well as any other virus classified by the ICTV as a picornavirus.

In particular embodiments, when functioning as the carrier virus, the modified picornavirus genome comprises the P2 and P3 regions. In other embodiments, the modified picornavirus genome comprises coding sequences for the $3D^{pol}$ protein and, optionally, the L, 2A, 2B, 2C and/or 3AB proteins. The modified picornavirus genome can also comprise sequences encoding viral proteases such as $L^{pro}$, $2A^{pro}$ and $3C^{pro}$. The modified picornavirus genome can further comprise the 5' and/or 3' nontranslated ends of the genome and/or a picornavirus packaging sequence, which is generally located in the genomic sequence encoding the structural proteins (P1).

Retroviruses are initially assembled and released from host cells as immature particles containing unprocessed Gag, Gag-Pol and Env precursors. These precursors are processed to form the proteins in the mature infectious virions including MA (matrix or membrane-associated protein), CA (capsid), NC (nucleocapsid), TM (transmembrane) and SU (surface protein). The RNA is condensed in the virions by association with NC within a protein core formed primarily of CA protein. The core is surrounded by a shell containing MA, which in turn is surrounded by the lipid bilayer of the viral envelope. The membrane contains the envelope glycoprotein, which is composed of the TM and SU subunits. The retroviral genome encodes Pol (polymerase), RT (reverse transcriptase) and IN (integrase) proteins as well as a number of accessory proteins (e.g., the lentiviral accessory proteins tat, rev, nef, vif, vpr, vpu [HIV] or vpx [SIV]) in more complex retroviruses such as HIV-1. The retrovirus packaging signal, ψ, is composed of one or more loop structures located in the 5' long terminal repeat (LTR). The term "retrovirus" has its conventional meaning in the art, and includes the *Alpharetrovirus* genus (e.g., Avian leucosis virus and Rous sarcoma virus), *Betaretrovirus* genus (e.g., Mouse mammary tumor virus, Mason-Pfizer monkey virus, Jaagsiekte sheep retrovirus), *Gammaretrovirus* genus (e.g., Murine leukemia viruses, Feline leukemia virus, Gibbon ape leukemia virus, reticuloendotheliosis virus), *Deltaretrovirus* genus (e.g., Human T-lymphotrophic virus, Bovine leukemia virus, Simian T-lymphotrophic virus), *Epsilonretrovirus* genus (e.g., Walleye dermal sarcoma virus, walleye epidermal hyperplasia virus 1), *lentivirus* genus (e.g., HIV, including HIV-1 and HIV-2, SIV, Equine infectious anemia virus, FIV, Caprine arthritis encephalitis virus, Visna/maedi virus) and the *Spumavirus* genus (e.g., Human foamy virus), and any other virus classified by the ICTV as a retrovirus.

In particular embodiments, when functioning as the carrier virus, the modified retrovirus genome comprises coding sequences for the retrovirus Pol and RT and, optionally, the IN and/or NC protein. For example, in particular embodiments, the modified retrovirus genome comprises the pol gene. The modified retrovirus genome can further encode one or more retrovirus accessory proteins (e.g., tat, rev, nef, vif, vpr, and/or vpu or vpx). In some embodiments, the modified retrovirus genome can also comprise the 5' and/or 3' LTRs and/or a retrovirus packaging sequence (e.g., psi sequence in the 5' LTR).

The second virus can also be any suitable virus now known or later discovered, including RNA and DNA viruses, single- and double-stranded and positive- and negative-sense viruses, and integrating and non-integrating viruses. In exemplary embodiments of the invention, the second virus is a virus that is virulent or pathogenic. In particular embodiments, the second virus is a retrovirus, such as a lentivirus (e.g., Human immunodeficiency Virus [HIV], Simian Immunodeficiency Virus [SIV], Feline Immunodeficiency Virus [FIV] or a SIV/HIV chimera [SHIV]), a filovirus, a coronavirus (e.g., SARS), a paramyxovirus, a myxovirus, an arenavirus, or an alphavirus.

Retroviruses, paramyxoviruses, myxoviruses and coronaviruses are discussed above. In representative embodiments, when the second virus is a retrovirus, the modified RNA genome of the carrier virus can comprise the gag and env genes. In other embodiments, the modified RNA genome comprises sequences encoding the retrovirus CA, M and Env proteins and, optionally, the protease.

When the second virus is a paramyxovirus, the modified RNA genome of the carrier virus can comprise sequences encoding the paramyxovirus M protein and the F and/or HN glycoproteins.

When the second virus is a myxovirus, the modified RNA genome of the carrier virus can comprise sequences encoding the HA and/or NA glycoprotein, the $M_1$ matrix protein and, optionally, the $M_2$, NB and/or CM2 proteins.

When the second virus is an alphavirus, the modified RNA genome of the carrier virus can comprise sequences encoding the C protein and the E1 and/or E2 glycoprotein.

When the second virus is a coronavirus, the modified RNA genome of the carrier virus can comprise sequences encoding the M protein and one or more of the S, HE and E proteins and, optionally, the N protein.

Filoviruses are enveloped viruses with nonsegmented, negative-stranded RNA genomes. The ribonucleoprotein complex (nucleocapsid) contains the genomic RNA associated with viral nucleoprotein (NP) and is surrounded by the virion envelope, from which peplomers of the envelope glycoprotein (GP, formed from $GP_1$ and $GP_2$) radiate. The viral VP40 protein is the most abundant protein in the virion and is believed to have a matrix protein function. The Filoviridae family includes the *Marburgvirus* genus (e.g., Lake Victoria marburgvirus) and the *Ebolavirus* genus (e.g., Ivory Coast ebolavirus, Reston ebolavirus, Sudan ebolavirus, Zaire virus), and any other virus classified by the ICTV as a filovirus.

When the second virus is a filovirus, the modified RNA genome of the carrier virus can comprise sequences encoding the filovirus GP and VP40 and, optionally, NP.

Arenaviruses are enveloped viruses having a bi-segmented single-stranded RNA genome. NP is the major structural protein of the viral nucleocapsid and associates with virion RNA. Two glycoproteins, GP1 and GP2, are found in equal amounts in the virion envelope. The Arenaviridae family includes the *Arenavirus* genus (e.g., Ippy virus, Lassa virus, Lymphocytic choriomeningitis virus, Mobala virus, Mopeia virus, Amapari virus, Flexal virus, Guanarito virus, Junin virus, Latino virus, Machupo virus, Oliveros virus, Parana virus, Pichinde virus, Pirital virus, Sabia virus, Tacaribe virus, Tamiami virus, Whitewater Arroyo virus); and any other virus classified by the ICTV as being an arenavirus.

When the second virus is an arenavirus, the modified RNA genome of the carrier virus can comprise sequences encoding the arenavirus GP1 and GP2 glycoproteins and, optionally, NP.

In particular embodiments, the structural proteins from the second virus are modified. For example, the modified structural protein from the second virus can be a fusion protein comprising the structural protein from the second virus and a heterologous peptide or protein. There are no particular limits to the size of the heterologous peptide or protein. In particular embodiments, the heterologous peptide or protein comprises at least about 5, 6, 8, 10, 12, 15, 20, 30, 50, 75, 100, 200, 300 or more amino acids. In embodiments of the invention, the modified structural protein retains regions that specifically interact with the genomic RNA, if any, and/or regions that interact with other structural proteins to facilitate virion assembly.

In particular embodiments, the heterologous peptide or protein is expressed as part of a fusion protein with a virion structural protein. By "expressed as part of a fusion protein with a virion structural protein" and the like, it is meant that the fusion protein comprises the heterologous peptide or protein and all, essentially all (i.e., at least about 90, 95, 97, 98% or more of the primary amino acid sequence), or a functional portion of the virion structural protein sufficient to interact with the genomic nucleic acid and/or other virion structural proteins to form the virion.

For example, according to this aspect of the invention, one or more of the structural proteins from the second virus can be modified to present an immunogen of interest on the virion surface (e.g., an immunogen from an infectious agent such as a bacterial, viral, yeast, fungal or protozoan immunogen, a cancer immunogen). Immunogenic peptides and proteins can be from any source, including other viruses, bacteria, protozoa, yeast, fungi, cancer cells, and the like. Immunogens are described in more detail hereinbelow.

In other embodiments, a structural protein from the second virus can be modified to present a targeting peptide or protein to increase entry into target cells and/or to alter tropism. Peptides or proteins that interact with cell-surfaces and alter virus entry and/or tropism are known in the art and can be from any source, including other viruses, bacteria, protozoa, yeast, fungi and the like, and include without limitation receptors, ligands, viral targeting peptides or proteins (e.g., envelope proteins or portions thereof), bacterial targeting peptides and proteins (e.g., from *Salmonella* or *Neisseria*), and synthetic sequences.

The heterologous peptide or protein can comprise all or a portion of a structural protein from another virus, i.e., the modified structural protein from the second virus is a chimeric structural protein comprising all or a portion of a structural protein from another virus (that is optionally different from the carrier virus as well). The heterologous peptide or protein from the structural protein from another virus can further be an immunogenic and/or targeting peptide or protein.

The term "chimeric structural protein" as used herein, is intended to encompass a fusion protein comprising all or essentially all (i.e., at least about 90, 95, 97, 98% or more of the primary amino acid sequence) of the structural protein from the second virus or a functional portion thereof sufficient to interact with the genomic nucleic acid and/or other virion structural proteins to form a virion and all, essentially all or a portion (e.g., an immunogenic and/or targeting portion) of a structural protein from another virus. For example, the chimeric structural protein can comprise the intracellular region of an envelope protein from the second virus and an envelope protein or immunogenic and/or targeting portion thereof from another virus (that is optionally different from the carrier virus).

In particular embodiments of the present invention, a "portion" of a peptide or protein is at least about 6, 10, 12, 15, 20, 30, 40, 50, 60, 100, 150, 100, 250 or more amino acids, optionally contiguous, amino acids.

In addition, as discussed in more detail below, one or more of the structural proteins from the second virus can be modified to comprise a nucleic acid binding domain.

In representative embodiments, the modified RNA genome encodes a virion structural protein from the second virus and a further virion structural protein comprising an interacting region capable of binding to the first structural protein in such a way as to promote assembly of the two structural proteins, wherein the chimeric virion structural protein further comprises a heterologous peptide or protein (e.g., to confer an altered tropism and/or to induce an immune response against the protein or peptide). For example, the modified RNA genome can encode a virion capsid, nucleocapsid or matrix protein from the second virus and a fusion protein comprising a region of an envelope protein (e.g., an intracellular region) from the second virus that interacts with the capsid, nucleocapsid or matrix protein, where the fusion protein further comprises a heterologous peptide or protein (e.g., to confer an altered tropism and/or to induce an immune response against the protein or peptide). In representative embodiments, a modified RNA virus genome encodes a retrovirus capsid protein and a chimeric retrovirus envelope protein that comprises the intracellular region of the retrovirus envelope protein and a heterologous protein or peptide. In particular embodiments, the heterologous peptide or protein comprises, consists essentially of or consists of all or a portion of an envelope protein from a virus that is different from the retrovirus (e.g., an immunogenic and/or targeting portion). For example, the modified retrovirus envelope protein can comprise all or part of a paramyxovirus (e.g., PIV or RSV) F glycoprotein to induce an immune response thereto. Alternatively, the heterologous peptide or protein can comprise, consist essentially of, or consist of any other immunogen and/or targeting peptide as described herein. In this context, "consist essentially of" means that the additional element(s) in the heterologous peptide or protein does not materially alter the immunogenic and/or targeting characteristics of the heterologous peptide or protein.

As another illustration, the modified RNA genome can encode an alphavirus capsid and a chimeric envelope protein that comprises the cytoplasmic tail from the E2 alphavirus glycoprotein, which directs interaction with the alphavirus capsid and a heterologous peptide or protein (as described herein).

With respect to lentivirus structural proteins, the modified RNA virus genome can encode a modified envelope glycoprotein (gp160) that increases cell surface expression of the envelope protein and/or enhances fusion of chimeric virions comprising immature forms of the envelope glycoprotein. The envelope glycoprotein gp160 is enzymatically cleaved during the fusion process, yielding two mature proteins, the transmembrane gp41 (TM) and the surface gp120 (SU). The C-terminal gp41 cytoplasmic tail contains endocytosis and cell sorting motifs that function to internalize the envelope glycoprotein, leaving less envelope glycoprotein on the cell surface. Truncations of the cytoplasmic carboxy tail or mutations in the tyrosine endocytosis motifs of gp41 have been shown to increase cell surface expression of envelope glycoprotein. Further, introduction of a carboxy tail deletion results in immature virions that can fuse with target cells at levels equivalent to mature virions. Thus, in certain embodiments of the present invention, the carrier RNA virus can comprise sequences encoding such gp41 carboxy tail truncations and/or mutations.

In representative embodiments, the modified carrier RNA virus genome does not encode, and the resulting virus particle does not comprise, any of the carrier RNA virus structural proteins (although some coding sequences that do not result in a functional protein may be present). In other embodiments, none or essentially none (e.g., less than about 1, 2, 5 or 10%) of the coding sequences for the carrier virus structural proteins are present in the modified carrier virus genome.

For example, the modified RNA virus genome can be derived from a self-replicating, but non-propagating "replicon" which does not express the structural proteins from the carrier virus, but which has been modified to comprise the structural proteins, and optionally accessory proteins, from a second virus so that the modified RNA genome encodes a self-propagating chimeric virus particle as discussed above.

To illustrate, alphavirus replicons are well known in the art (see, e.g., U.S. Pat. No. 5,505,947 to Johnston et al.; U.S. Pat. No. 5,792,462 to Johnston et al.; U.S. Pat. Nos. 6,156,558; 6,521,325; 6,531,135; 6,541,010; and Pushko et al. (1997) *Virol.* 239:389-401; U.S. Pat. No. 5,814,482 to Dubensky et al.; U.S. Pat. No. 5,843,723 to Dubensky et al.; U.S. Pat. No. 5,789,245 to Dubensky et al.; U.S. Pat. No. 5,739,026 to Garoff et al.).

In particular embodiments, a modified alphavirus genome when functioning as a carrier virus according to the present invention comprises the 5' and 3' untranslated ends of the alphavirus genome, and the nsP1, nsP2, nsP3 and nsP4 non-structural protein coding sequences.

Replicon systems for a number of other viruses are known in the art, for example, retroviruses (see Chang et al., (2001) *Current Opinion In Molecular Therapeutics* 3:468-475; Soneoka et al., (1995) *Nucleic Acids Research* 23:628-633; O'Rourke et al., (2003) *Molecular Therapy* 7: 632-639; Kotsopoulou et al., (2000) *J. Virol.* 74:4839-4852; U.S. Pat. Nos. 6,277,633 and 6,521,457 to Olsen et al.; and U.S. Pat. No. 6,013,516 to Verma et al.); rabies (Schnell et al., (2000) 97:3544-3549); paramyxoviruses (Bukreyev et al., (2006) *J. Virol.* 80: 2267-2279; Bukreyev et al., (2005) *J. Virol.* 79:13275-13284); rhinovirus (McKnight, (2003) *Arch. Virol.* 148:2397-2418); picornavirus (Barclay et al., (1998) *J. Gen. Virology* 79:1725-1734); coronavirus (Curtis et al., (2002) *J. Virol.* 76: 1422-1434; Fosmire et al., (1992) *J. Virol.* 66:3522-3530); VSV (Johnson et al., (1997) *J. Virol.* 71:5060-5068); and yellow fever virus (Jones et al., (2005) *Virology* 331:247-259).

In general, in the replicon system, the viral genome contains the viral sequences for viral replication (e.g., the alphavirus nsP1-4 genes), but is modified so that it is defective for expression of at least one viral structural protein required for production of new viral particles (e.g., because of mutations in the structural protein coding sequences or promoter driving expression of the structural protein coding sequences, or because the structural protein coding sequences are partially or entirely deleted). RNA transcribed from the replicon contains sufficient viral sequences (e.g., the viral replicase proteins) responsible for RNA replication and transcription. Thus, if the transcribed RNA is introduced into susceptible cells, it will be replicated and translated to give the replication proteins. These proteins will transcribe the modified RNA virus genome, which will result in the production of new chimeric viral particles packaging the modified RNA virus genome.

The coding sequences for the structural proteins can be expressed from the modified carrier virus genome using any method known in the art. For example, each coding sequence can be operably linked to a different promoter element (e.g., an alphavirus 26S promoter). Alternatively, more than one open reading frame (ORF) can be operably linked to a promoter element, with IRES sequences being present 5' of each of the downstream ORFs. As a further alternative, the structural proteins can be expressed as a polyprotein comprising protease cleavage sites for proper processing of the polyprotein to yield the constitutive proteins.

The promoter can be native to the carrier RNA virus, native to the second virus, or heterologous (i.e., foreign) to both, and can further be partially or completely synthetic. When the modified RNA virus genome is a modified alphavirus genome, the structural proteins of the second virus can be operatively associated with an alphavirus 26S promoter (e.g., a VEE or Sindbis 26S promoter). Further, the modified alphavirus genome can comprise two or more 26S promoters, each directing expression of a different open reading frame (e.g., a retrovirus Gag coding sequence can be operatively associated with one 26S promoter and a retrovirus envelope protein coding sequence can be operatively associated with another 26S promoter).

In representative embodiments wherein the modified RNA virus genome is a modified rhabdovirus genome, the structural proteins of the second virus are operatively associated with one of the rhabdovirus intergenic regions (e.g., the intergenic region in the negative sense) to facilitate proper transcription.

As a further approach, the modified carrier RNA virus genome can comprise coding sequences for structural proteins from two or more different viruses (e.g., from two, three or four different viruses) that are derived from viruses other than the carrier virus, and the resulting chimeric virion comprises structural proteins from the two or more viruses. Thus, the structural proteins in the chimeric virus can comprise structural proteins from the second virus as well as from another virus(es) or can consist of structural proteins from the second virus alone.

In certain embodiments, the modified carrier virus genome comprises cis-acting sequences and/or coding sequences for proteins that facilitate maturation of the structural proteins, for example, a retrovirus protease such as a HIV, FIV or SIV protease. As one approach, a retrovirus protease can be expressed from a sequence encoding a Gag/Pol precursor, optionally truncated at the end of the protease coding sequence. Optionally, the Gag/Pol precursor is the product of the normal frameshift in gag (e.g., for lentiviruses, alpharetroviruses and betaretroviruses).

In representative embodiments, expression of the sequences encoding the retrovirus protease, or any other protein that facilitates maturation, are regulated. For example, the coding sequence can be operatively associated with an inducible promoter and/or a relatively weak or relatively strong promoter that drives expression at low or high levels, respectively. Alternatively, a sequence encoding an attenuated retrovirus protease (or other maturation protein) can be used. The protease gene has been studied extensively in this regard, facilitating the choice of mutation(s) to produce a range of protease activities (see, e.g., Rose et al. (1995) J. Virol. 69:2751-2758). For example, a carboxy or amino terminus extension can be added to the protease coding sequence to produce an attenuated protein. To illustrate, a truncated retrovirus reverse transcriptase coding sequence can be added to the 3' end of a retrovirus protease open reading frame to produce an attenuated protease protein. Further, an agent such as saquinavir, or any other retrovirus protease inhibitor, can also be used to attenuate the activity of a retrovirus protease. Another approach is to mutate the frameshifting site to reduce the relative level of a Gag/Pro precursor for those retroviruses in which the protease reading frame is shifted as compared with gag, such as betaretroviruses, deltaretroviruses and lentiviruses including HIV, SIV and FIV (see Evans et al., (2004) J. Virol. 78:11715-11725). In other representative embodiments, a modified Gag/Pol precursor coding sequence is used in which the complete reverse transcriptase coding sequence is present but contains one or more mutations in the active site to yield an inactive or attenuated protein, and the integrase coding sequence is either not present or is mutated to produce an inactive or attenuated protein.

As used herein, the term "mutation" refers to substitutions, insertions and/or deletions, the latter including truncations.

In embodiments where the second virus is a retrovirus, the modified RNA genome comprises a sequence encoding the HIV-1 Vpu (or SIV Vpx protein), which is believed to facilitate maturation of the envelope glycoprotein and its intracellular trafficking to the plasma membrane for inclusion in budded particles (Bour and Strebel, (2003) Microbes Infect. 11:1029-39).

In some embodiments, the chimeric viral vector and/or a chimeric viral particle packaging the chimeric viral vector comprises attenuating mutations. The chimeric viral vector or virus particle can be attenuated, for example, by the introduction of attenuating mutations into the 5' or 3' untranslated regions of the modified carrier virus genome, the nonstructural protein coding sequences, structural protein coding sequences and/or accessory protein coding sequences or any other viral sequence. Elements regulating packaging, translation, transcription and/or replication can be embedded within the coding sequences and can also be modified to be attenuating. The phrases "attenuating mutation" and "attenuating amino acid," as used herein, mean a nucleotide sequence containing a mutation, or an amino acid encoded by a nucleotide sequence containing a mutation, which mutation results in a decreased probability of causing disease in its host (i.e., reduction in virulence), in accordance with standard terminology in the art. See, e.g., B. Davis et al., MICROBIOLOGY 132 (3d ed. 1980). The phrase "attenuating mutation" excludes mutations or combinations of mutations that would be lethal to the virus.

Appropriate attenuating mutations are dependent upon the viruses used. Suitable attenuating mutations within the alphavirus genome are known to those skilled in the art. Exemplary alphavirus attenuating mutations include, but are not limited to, those described in U.S. Pat. No. 5,505,947 to Johnston et al., U.S. Pat. No. 5,185,440 to Johnston et al., U.S. Pat. No. 5,643,576 to Davis et al., U.S. Pat. No. 5,792,462 to Johnston et al., U.S. Pat. No. 5,639,650 to Johnston et al., and U.S. Patent Publication No. US-2004-0030117-A1 to Johnston et al., the disclosures of which are incorporated herein in their entireties by reference.

In exemplary embodiments, the attenuating mutation is one that increases the sensitivity of the virus to interferon (e.g., a G→A, U or C mutation at nucleotide 3 in the 5' region of a modified VEE genome or a Thr→Ile substitution at S.A.AR86 nsP1 amino acid position 538).

Attenuating mutations are known for other viruses as well, see, e.g., Silke et al., (1999) J. Virology 73:2790-2797 (retrovirus) and Publicover et al., (2004) J. Virology 78:9317-9324 (rhabdovirus).

The chimeric viral vector, optionally packaged in a chimeric virus particle, can be employed for immunization against the structural proteins of the second virus. This aspect of the invention can be practiced to more safely produce an immune response against a pathogenic virus. According to this particular embodiment, the pathogenic effects produced in the subject by administration of the live, chimeric virus vector or chimeric virus particle are less than the pathogenic effects that would be produced by administering the live, pathogenic second virus to the subject.

The chimeric viral vectors or virus particles of the invention can be administered to a subject, enter susceptible cells in the body, reproduce in those cells, spread to other cells and induce an immune response, with reduced disease symptomology as compared with direct immunization with a live pathogenic virus. The spread of the vaccine virus in the body can magnify the vaccine effect over that which is achieved by simply inactivating pathogenic virions and inoculating them as a vaccine.

The modified carrier virus genome can further express one or more nonstructural proteins (or an antigenic fragment thereof) from the second virus (e.g., reverse transcriptase from HIV or SIV), e.g., to induce an immune response against the non-structural protein(s). According to this embodiment, it is generally preferred that the nonstructural protein(s) be expressed in a truncated or otherwise mutated form that is immunogenic but not functional.

In one particular embodiment, the invention can be practiced to develop a safer, live virus vaccine for SIV, HIV or FIV. According to representative embodiments, the chimeric viral vector comprises a modified alphavirus genome comprising alphavirus (e.g., VEE) 5' and 3' ends (i.e., the noncoding regions of the genome comprising cis-acting elements involved in viral replication), alphavirus coding sequences capable of replicating the genome (e.g., nsP1, nsP2, nsP3 and/or nsP4 coding sequences) as well as Gag and gp160 coding sequences (can be in native or modified forms) from a lentivirus such as SIV, FIV and/or HIV including SIV/HIV chimeras [SHIV]. Optionally, the virus genome is further modified by inclusion of the SIV, FIV or HIV ψ packaging sequence (in native or modified form) so that the virus genome can specifically interact with Gag. In representative embodiments, the ψ packaging sequence is positioned between the alphavirus nsP4 coding sequence (e.g., VEE nsP4 coding sequence) and the alphavirus (e.g., VEE) 26S promoter. The SIV, FIV and/or HIV sequences can be associated with one or more promoters, for example, one or more alphavirus 26S subgenomic promoters, as described herein. As described above, the modified alphavirus genome can optionally further encode an SIV, FIV or HIV protease.

In other embodiments, the invention provides a chimeric viral vector comprising a modified rhabdovirus genome (e.g., VSV) that comprises cis-acting sequences (e.g., 5' and 3' untranslated sequences) and sequences encoding rhabdovirus proteins for viral genomic replication, as well as a Gag and gp160 coding sequences (can be in native or modified forms) from a lentivirus such as SIV, FIV and/or HIV including SIV/HIV chimeras [SHIV]. Optionally, the virus genome is further modified by inclusion of the SIV, FIV or HIV ψ packaging sequence (in native or modified form) so that the virus genome can specifically interact with Gag. In particular embodiments, the ψ packaging sequence is inserted into the 5' untranslated region of the modified rhabdovirus genome. As described above, the modified rhabdovirus genome can optionally further encode an SIV, FIV or HIV protease. Further, the lentivirus coding sequences can be operably associated with a rhabdovirus intergenic region (e.g., in the negative sense).

In still further embodiments, the invention provides a chimeric viral vector comprising a modified coronavirus genome that comprises cis-acting sequences (e.g., 5' and/or 3' untranslated sequences and/or the 3' end of orf1b that contains the packaging signal) and sequences encoding coronavirus proteins for viral genomic replication, as well as a Gag and gp160 coding sequences (can be in native or modified forms) from a lentivirus such as SIV, FIV and/or HIV including SIV/HIV chimeras [SHIV]. Optionally, the virus genome is further modified by inclusion of the SIV, FIV or HIV ψ packaging sequence (in native or modified form) so that the virus genome can specifically interact with Gag. In particular embodiments, the ψ packaging sequence is inserted into the 5' and/or 3' untranslated region of the modified coronavirus genome. As described above, the modified coronavirus genome can optionally further encode an SIV, FIV or HIV protease.

Thus, the present invention advantageously provides a safer alternative to provide immunity against a pathogenic virus, such as HIV, FIV and/or SIV including SIV/HIV chimeras [SHIV]. For example, using the SIV macaque model, only an experimental live attenuated SIV vaccine has been effective in preventing infection and subsequent disease from a virulent SIV challenge. However, the genetic material of the SIV vaccine virus integrates into the chromosomes of primates, and eventually the animals inoculated with the live attenuated SIV vaccine begin to show disease symptoms. Therefore, even though this approach has shown real protection from SIV infection, it is highly unlikely that it will be carried forward into human trials of an analogous vaccine for HIV. According to particular embodiments of the invention, the inventive viral vaccines do not integrate into the host chromosomes and will produce a virus particle that presents the antigenic structure of HIV.

The invention also encompasses chimeric viral vectors and virus particles that function as delivery vectors for other immunogens, which can be presented on the virion surface (e.g., as a chimeric structural protein encoding the immunogen, as described in more detail above) or expressed as a separate peptide or protein (i.e., is not expressed as part of the virion structural proteins) as is well known in the art with respect to conventional delivery vectors. The immunogen can be from a pathogenic organism (e.g., bacteria, yeast, fungi or protozoa), from a virus or can be a cancer antigen. Thus, in particular embodiments, the chimeric viral vector comprises one or more heterologous nucleic acid(s) encoding an immunogenic protein or peptide. In this context, "heterologous" means that the nucleic acid is foreign to both the carrier virus and the second virus. Immunogens are as described in more detail below. Alternatively, the heterologous nucleic acid(s) can encode any other protein, peptide or nontranslated RNA (e.g., antisense RNA, RNAi) of interest.

Further, the chimeric viral vector can comprise one or more heterologous nucleic acid(s) encoding a therapeutic protein or peptide, including but not limited to an immune stimulant such as a cytokine (including inflammatory cytokines), a chemokine and/or a growth factor. In particular embodiments, the heterologous nucleic acid encodes α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin) and/or other immune mediator.

There are no particular limits to the size of the heterologous nucleic acid. In particular embodiments, the heterologous nucleic acid is at least about 15, 18, 24, 50, 100, 250, 500, 1000 or more nucleotides long.

The invention also provides self-propagating chimeric virus particles comprising the chimeric viral vectors of the invention packaged within the virion structural proteins encoded by the modified genome, for example, the virion comprises, consists essentially of, or consists of structural proteins from the second virus. In this context, "consists essentially of" means that the structural proteins do not include any additional elements that materially affect the function and/or structure of the structural proteins.

The modified carrier virus genome can be packaged by the structural proteins by any suitable method, for example: (1) nonspecific incorporation of the modified virus genome into assembling virus particles (e.g., by retrovirus Gag); (2) insertion of a cis-acting packaging sequence that recognizes the structural proteins in the modified genome and/or (3) insertion of a nucleic acid binding domain (which can be specific or non-specific) into one or more of the structural proteins. Thus, the modified carrier virus genome can optionally comprise a cis-acting packaging element that is recognized by the structural proteins and/or one or more of the structural protein coding sequences can be modified to encode a structural protein with a nucleic acid binding domain. For example, the packaging element can be an alphavirus packaging sequence, a rhabdovirus packaging sequence, a coronavirus packaging sequence, or a retrovirus (e.g., a lentivirus such as SIV, FIV or HIV) ψ packaging sequence. The packaging element and/or nucleic acid binding domain can be naturally occurring or, alternatively, can be partly or completely synthetic. The cis-acting packaging element can be from the second virus and recognize the structural proteins thereof. Likewise, the nucleic acid binding domain can be from the carrier virus and recognize the modified carrier virus genome. As another possibility, a cis-acting packaging sequence and corresponding nucleic acid binding element from another virus or organism can be engineered into the chimeric virus. Viral cis-acting packaging sequences and nucleic acid binding domains are known in the art.

As one illustration, a retrovirus (e.g., a lentivirus such as SIV, FIV or HIV) ψ packaging sequence can be incorporated into the modified genomic RNA to facilitate packaging of the genome into a virion comprising lentivirus Gag proteins (more specifically, the nucleocapsid domain of the Gag protein). For retroviruses the ψ packaging signal is composed of one or more stem-loop structures located in the 5' LTR. In the case of HIV-1, the ψ element is composed primarily of four stem-loop structures, which associate with two zinc-knuckle modules in the HIV-1 nucleocapsid protein.

As another example, an alphavirus nucleic acid binding domain from an alphavirus capsid protein can be incorporated into a structural protein from another virus (e.g., a modified retrovirus Gag protein containing an alphavirus nucleic acid binding element) to facilitate packaging of a modified alphavirus genomic RNA. The amino terminal 125 amino acids of alphavirus capsid proteins are known to specifically bind the virus genomic RNA for packaging into virions (Perri et al., (2003) *J. Virol.* 77:10394-10403). In particular embodiments, smaller portions of the capsid protein are used.

For example, in particular embodiments, the second virus is a retrovirus and the retrovirus Gag precursor is modified to comprise a carboxy terminal addition of a portion of the alphavirus capsid protein comprising the nucleic acid binding domain. An alternative configurations include positioning the alphavirus capsid nucleic acid binding domain so that a Gag-capsid fusion protein is synthesized only after normal ribosomal frame-shifting. According to this embodiment, the alphavirus nucleic acid binding domain is contained in a frame-shifted molecule containing Gag through amino acid 392 (SHIV89.6P numbering, see Examples), Pro amino acids 1-118, and the alphavirus nucleic acid binding domain. The Gag precursor fusion protein with the fragment of the alphavirus capsid can further comprise a linker between the two.

In the case of a modified alphavirus genome, in particular embodiments, the foreign packaging sequence is positioned between an alphavirus nsP4 coding sequence and an alphavirus 26S promoter.

As a further possibility, the coronavirus M protein interacts with a cis-acting genomic RNA sequence. It has been shown that a heterologous RNA that includes this cis-acting element will interact with the coronavirus M protein. Thus, in certain embodiments, one or more structural proteins are modified to comprise all or part of the intracellular region of the coronavirus M protein (or a portion thereof containing the nucleic acid binding domain) and the modified carrier virus genome comprises the cis-acting element that interacts with the M protein.

As another aspect, the invention also provides nucleic acids (e.g., DNA) encoding the chimeric viral vectors of the invention, which nucleic acids can optionally can be incorporated into a vector (e.g., a plasmid, phage, bacterial artificial chromosome, or a viral vector).

The invention also provides virus particles comprising the chimeric viral vectors of the invention. The virus particle can be a chimeric virus particle comprising the structural proteins encoded by the chimeric viral vector. According to this embodiment, the chimeric virus particle can have any of the features discussed herein with respect to chimeric viral vectors. Alternatively, the virus particle can be a delivery vector for delivering the chimeric viral vector into a cell in vitro (e.g., for chimeric virus production) or to a subject in vivo, and chimeric virus particles are produced from the chimeric viral vector after infection of a host cell. For example, an alphavirus vector can be used to deliver a modified chimeric alphavirus genome encoding retrovirus structural proteins, which can optionally be modified retrovirus structural proteins as described elsewhere herein.

The chimeric viral vectors and virus particles of the invention can be produced and administered by any method known in the art. For example, the modified carrier virus genome can be introduced into a cultured cell (e.g., generally a cell that is permissive for replication of the carrier virus) under conditions sufficient for production of the chimeric virus particles, which can then be isolated from the culture. The modified RNA genome can be introduced by any method known in the art including transfection (e.g., electroporation), liposomes, or a viral delivery vector.

Alternatively, cultured cells can be infected with a chimeric virus particle, which is self-propagating and will produce new virus particles.

As still a further possibility, RNA viruses can be expressed from a nucleic acid (e.g., DNA) molecule encoding the chimeric viral vector. In particular embodiments, a DNA delivery vector (e.g., a DNA virus delivery vector) encoding the chimeric viral vector is introduced into the cells to produce the chimeric virus particle.

In particular embodiments, the invention provides a method of making a chimeric virus particle, comprising introducing a chimeric viral vector of the invention, a nucleic acid encoding a chimeric viral vector of the invention, or a virus particle comprising either of the foregoing into a cell under conditions sufficient for chimeric virus particles to be produced, wherein the chimeric virus particles each comprise the chimeric viral vector packaged within virion structural proteins from the second virus, which can be modified structural proteins as described herein (i.e., the virion encoded by the modified RNA virus genome). In particular embodiments, the chimeric viral vector or a nucleic acid encoding the same is introduced into the cell by transfection (e.g., electroporation), liposomes or a viral delivery vector.

Suitable cells for producing viruses are known in the art. In particular embodiments, the embodiments, the cell is permissive for propagation of the chimeric virus particles and, optionally, infection by the chimeric virus particles. In particular embodiments, the cells have an impaired interferon system, such as Vero cells or cells in which interferon expression is impaired (e.g., by the use of RNAi). The cells can also be modified to express receptors or other cell-surface molecules for recognizing the chimeric virion. For example, in the case of a chimeric virion comprising HIV proteins, the cells can express, or be modified to express, human CCR5 and human CD4 receptors (e.g., 3T3 cells or Vero cells expressing CD4 and/or CCR5 receptors). In addition, the virion can be modified to express a targeting peptide or protein on the virion surface (e.g., a modified structural protein) that recognizes a receptor or other cell-surface molecule on the host cells. As known in the art, cell lines can further be engineered to express proteins required for uncoating or assembly of the virus.

In other representative embodiments, chimeric virus particles can be produced in a subject (e.g., bovines, ovines, caprines, porcines, lagomorphs, rodents, etc.) that functions as a bioreactor and the chimeric virus particles collected therefrom.

The present invention finds use in both veterinary and medical applications. Suitable subjects include avians, mammals and fish, with mammals being preferred. The term "avian" as used herein includes, but is not limited to, chickens, ducks, geese, quail, turkeys and pheasants. The term "mammal" as used herein includes, but is not limited to, primates (e.g., simians and humans), bovines, ovines, caprines, porcines, equines, felines, canines, lagomorphs, rodents (e.g., rats and mice), etc. Human subjects include fetal, neonatal, infant, juvenile and adult subjects.

The invention can be used in either a therapeutic or prophylactic manner. For example, in one embodiment, to protect against an infectious disease, subjects may be vaccinated prior to exposure, as neonates or adolescents. Adults that have not previously been exposed to the disease may also be vaccinated.

In particular embodiments, the present invention provides a pharmaceutical composition comprising a chimeric viral vector of the invention, or nucleic acid encoding the same, or a virus particle comprising either of the foregoing in a pharmaceutically-acceptable carrier, optionally with other medicinal agents, pharmaceutical agents, carriers, adjuvants, diluents, etc. For injection, the carrier is typically a liquid. For other methods of administration, the carrier may be either solid or liquid, such as sterile, pyrogen-free water or sterile pyrogen-free phosphate-buffered saline solution. For inhalation administration, the carrier will be respirable, and is optionally in solid or liquid particulate form. Formulation of pharmaceutical compositions is well known in the pharmaceutical arts (see, e.g., Remington's Pharmaceutical Sciences, (15th Edition, Mack Publishing Company, Easton, Pa. (1975)).

By "pharmaceutically acceptable" it is meant a material that is not biologically or otherwise undesirable, e.g., the material may be administered to a subject without causing any undesirable biological effects.

The chimeric viral vectors or virus particles (or nucleic acids encoding the same) of the invention can be administered to elicit an immunogenic response. Typically, immunological compositions of the present invention comprise an immunogenically effective amount of infectious chimeric viral vectors, chimeric virus particles (or nucleic acids encoding the same) as disclosed herein in combination with a pharmaceutically-acceptable carrier.

An "immunogenically effective amount" is an amount that is sufficient to induce an immune response in the subject to which the pharmaceutical formulation is administered. In certain embodiments, a dosage of about $10^3$ to about $10^{15}$ infectious units, about $10^4$ to about $10^{10}$ infectious units, about $10^2$ to about $10^6$ infectious units, about $10^3$ to about $10^5$ infectious units, about $10^5$ to about $10^9$ infectious units, or about $10^6$ to about $10^8$ infectious units per dose is suitable, depending upon the age and species of the subject being treated, and the immunogen against which the immune response is desired. In yet further embodiments, the dosage is from about 10, about $10^2$, about $10^3$, about $10^4$, or about $10^5$ infectious units per dose to about $10^4$, about $10^5$, about $10^6$, about $10^7$, about $10^8$, about $10^9$, or about $10^{10}$ infectious units per dose.

The terms "vaccination" or "immunization" are well-understood in the art. For example, the terms vaccination or immunization can be understood to be a process that increases a subject's immune reaction to antigen and therefore the ability to resist or overcome infection. In the case of the present invention, vaccination or immunization may also increase the recipient's immune response and resistance to invasion by cancer or tumor cells and/or elimination of tumor or cancer cells.

The immunogen can be an immunogen from an infectious agent, a cancer immunogen, an allergic reaction immunogen (i.e., an allergen), a transplantation immunogen, an autoantigen, and the like as are known in the art.

To illustrate, a cancer immunogen (i.e., an immunogen associated with cancer cells, optionally specifically associated with cancer cells) can include, without limitation, HER2/neu and BRCA1 antigens for breast cancer, MART-1/MelanA, gp100, tyrosinase, TRP-1, TRP-2, NY-ESO-1, CDK-4, β-catenin, MUM-1, Caspase-8, KIAA0205, HPVE7, SART-1, PRAME, and p15 antigens, members of the MAGE family, the BAGE family (such as BAGE-1), the DAGE/PRAME family (such as DAGE-1), the GAGE family, the RAGE family (such as RAGE-1), the SMAGE family, NAG, TAG-72, CA125, mutated proto-oncogenes such as p21ras, mutated tumor suppressor genes such as p53, tumor associated viral antigens (e.g., HPV16 E7), the SSX family, HOM-MEL-55, NY-COL-2, HOM-HD-397, HOM-RCC-1.14, HOM-HD-21, HOM-NSCLC-11, HOM-MEL-2.4, HOM-TES-11, RCC-3.1.3, NY-ESO-1, and the SCP family. Members of the MAGE family include, but are not limited to, MAGE-1, MAGE-2, MAGE-3, MAGE-4 and MAGE-11. Members of the GAGE family include, but are not limited to, GAGE-1, GAGE-6. See, e.g., review by Van den Eynde and van der Bruggen (1997) in *Curr. Opin. Immunol.* 9: 684-693, Sahin et al. (1997) in *Curr. Opin. Immunol.* 9: 709-716, and Shawler et al. (1997).

The cancer immunogen can also be, but is not limited to, human epithelial cell mucin (Muc-1; a 20 amino acid core repeat for Muc-1 glycoprotein, present on breast cancer cells and pancreatic cancer cells), MUC-2, MUC-3, MUC-18, the Ha-ras oncogene product, carcino-embryonic antigen (CEA), the raf oncogene product, CA-125, GD2, GD3, GM2, TF, sTn, gp75, EBV-LMP 1 & 2, HPV-F4, 6, 7, prostatic serum antigen (PSA), prostate-specific membrane antigen (PSMA), alpha-fetoprotein (AFP), CO17-1A, GA733, gp72, p53, the ras oncogene product, β-HCG, gp43, HSP-70, p17 mel, HSP-70, gp43, HMW, HOJ-1, melanoma gangliosides, TAG-72, mutated proto-oncogenes such as p21ras, mutated tumor suppressor genes such as p53, estrogen receptor, milk fat globulin, telomerases, nuclear matrix proteins, prostatic acid phosphatase, protein MZ2-E, polymorphic epithelial mucin (PEM), folate-binding-protein LK26, truncated epidermal growth factor receptor (EGFR), Thomsen-Friedenreich (T) antigen, GM-2 and GD-2 gangliosides, polymorphic epithelial mucin, folate-binding protein LK26, human chorionic gonadotropin (HCG), pancreatic oncofetal antigen, cancer antigens 15-3, 19-9, 549, 195, squamous cell carcinoma antigen (SCCA), ovarian cancer antigen (OCA), pancreas cancer associated antigen (PaA), mutant K-ras proteins, mutant p53, and chimeric protein $P210_{BCR-ABL}$ and tumor associated viral antigens (e.g., HPV16 E7).

The cancer immunogen can also be an antibody produced by a B cell tumor (e.g., B cell lymphoma; B cell leukemia; myeloma; hairy cell leukemia), a fragment of such an antibody, which contains an epitope of the idiotype of the antibody, a malignant B cell antigen receptor, a malignant B cell immunoglobulin idiotype, a variable region of an immunoglobulin, a hypervariable region or complementarity determining region (CDR) of a variable region of an immunoglobulin, a malignant T cell receptor (TCR), a variable region of a TCR and/or a hypervariable region of a TCR. In one embodiment, the cancer antigen can be a single chain antibody (scFv), comprising linked $V_H$, and $V_L$ domains, which retains the conformation and specific binding activity of the native idiotype of the antibody.

The immunogens that can be used in accordance with the present invention are in no way limited to the cancer immunogens listed herein. Other cancer immunogens can be identified, isolated and cloned by methods known in the art such as those disclosed in U.S. Pat. No. 4,514,506.

The cancer to be treated or immunized against (i.e., prophylactic treatment) can be, but is not limited to, B cell lymphoma, T cell lymphoma, myeloma, leukemia, hematopoietic neoplasias, thymoma, lymphoma, sarcoma, lung cancer, liver cancer, non-Hodgkins lymphoma, Hodgkins lymphoma, uterine cancer, adenocarcinoma, breast cancer, pancreatic cancer, colon cancer, lung cancer, renal cancer, bladder cancer, liver cancer, prostate cancer, ovarian cancer, primary or metastatic melanoma, squamous cell carcinoma, basal cell carcimona, brain cancer, angiosarcoma, hemangiosarcoma, head and neck carcinoma, thyroid carcinoma, soft tissue sarcoma, bone sarcoma, testicular cancer, uterine cancer, cervical cancer, gastrointestinal cancer, and any other cancer now known or later identified (see, e.g., Rosenberg (1996) *Ann. Rev. Med.* 47:481-491).

Infectious agent immunogens can include any immunogen suitable for protecting a subject against an infectious disease, including but not limited to microbial, bacterial, protozoal, parasitic and viral diseases. Such infectious agent immunogens can include, but are not limited to, immunogens from Hepadnaviridae including hepatitis A, B, C, D, E, F, G, etc.; Flaviviridae including human hepatitis C virus (HCV), yellow fever virus and dengue viruses; Retroviridae including human immunodeficiency viruses (HIV), simian immunodeficiency virus (SIV), and human T lymphotropic viruses (HTLV1 and HTLV2); Herpesviridae including herpes simplex viruses (HSV-1 and HSV-2), Epstein Barr virus (EBV), cytomegalovirus, varicella-zoster virus (VZV), human herpes virus 6 (HHV-6) human herpes virus 8 (HHV-8), and herpes B virus; Papovaviridae including human papilloma viruses; Rhabdoviridae including rabies virus; Paramyxoviridae including respiratory syncytial virus; Reoviridae including rotaviruses; Bunyaviridae including hantaviruses; Filoviridae including Ebola virus; Adenoviridae; Parvoviridae including parvovirus B19; Arenaviridae including Lassa virus; Orthomyxoviridae including influenza viruses; Poxyiridae including Orf virus, molluscum contageosum virus, smallpox virus and Monkey pox virus; Togaviridae including Venezuelan equine encephalitis virus; Coronaviridae including coronaviruses such as the SARS coronavirus; and Picornaviridae including polioviruses; rhinoviruses; orbiviruses; picodnaviruses; encephalomyocarditis virus (EMV); Parainfluenza viruses, adenoviruses, Coxsackieviruses, Echoviruses, Rubeola virus, Rubella virus, human papillomaviruses, Canine distemper virus, Canine contagious hepatitis virus, Feline calicivirus, Feline rhinotracheitis virus, TGE virus (swine), Foot and mouth disease virus, simian virus 5, human parainfluenza virus type 2, human metapneuomovirus, enteroviruses, and any other pathogenic virus now known or later identified (see, e.g., *Fundamental Virology*, Fields et al., Eds., $3^{rd}$ ed., Lippincott-Raven, New York, 1996).

As further examples, the immunogen may be an orthomyxovirus immunogen (e.g., an influenza virus immunogen, such as the influenza virus hemagglutinin (HA) surface protein, influenza neuraminidase protein, the influenza virus nucleoprotein (NP) antigen, or an equine influenza virus immunogen), or a lentivirus immunogen (e.g., an equine infectious anemia virus immunogen, a SIV immunogen, or a HIV immunogen, such as, e.g., HIV or SIV gp120, gp160, gp41, matrix protein, capsid protein, protease, polymerase, the envelope protein subunits (TM and/or SU), reverse transcriptase, or integrase). The immunogen may also be an arenavirus immunogen (e.g., Lassa fever virus immunogen, such as the Lassa fever virus nucleocapsid protein gene and the Lassa fever envelope glycoprotein gene), a Picornavirus immunogen (e.g., a Foot and Mouth Disease virus immunogen), a poxvirus immunogen (e.g., a vaccinia immunogen, such as the vaccinia L1 or L8 genes), an Orbivirus immunogen (e.g., an African horse sickness virus immunogen), a flavivirus immunogen (e.g., a yellow fever virus immunogen, a West Nile virus immunogen, or a Japanese encephalitis virus immunogen), a filovirus immunogen (e.g., an Ebola virus immunogen, or a Marburg virus immunogen, such as NP and GP genes), a bunyavirus immunogen (e.g., RVFV, CCHF, and SFS immunogens), a norovirus immunogen (e.g., a Norwalk virus immunogen), or a coronavirus immunogen (e.g., an infectious human coronavirus immunogen, such as the human coronavirus envelope glycoprotein gene, or a porcine transmissible gastroenteritis virus immunogen, a SARS virus immunogen, or an avian infectious bronchitis virus immunogen). The immunogen may further be a polio antigen, herpes antigen (e.g., CMV, EBV, HSV antigens) mumps antigen, measles antigen, rubella antigen, diptheria toxin or other diptheria antigen, pertussis antigen, hepatitis (e.g., hepatitis A or hepatitis B) antigen (e.g., HBsAg, HBcAg, HBeAg), or any other vaccine immunogen known in the art.

The immunogen can be an immunogen from a pathogenic microorganism, which can include but is not limited to, *Rickettsia, Chlamydia, Mycobacteria, Clostridia, Corynebacteria, Mycoplasma, Ureaplasma, Legionella, Shigelia, Salmonella*, pathogenic *Escherichia coli* species, Bordatella, *Neisseria, Treponema, Bacillus, Haemophilus, Moraxella, Vibrio, Staphylococcus* spp., *Streptococcus* spp., *Campylobacter* spp., *Borrelia* spp., *Leptospira* spp., *Erlichia* spp., *Klebsiella* spp., *Pseudomonas* spp., *Helicobacter* spp., and any other pathogenic microorganism now known or later identified (see, e.g., Microbiology, Davis et al, Eds., $4^{th}$ ed., Lippincott, New York, 1990).

Specific examples of microorganisms from which the immunogen of this invention can be obtained include, but are not limited to, *Helicobacter pylori, Chlamydia pneumoniae, Chlamydia trachomatis, Ureaplasma urealyticum, Mycoplasma pneumoniae, Staphylococcus aureus, Streptococcus pyogenes, Streptococcus pneumoniae, Streptococcus viridans, Enterococcus faecalis, Neisseria meningitidis, Neisseria gonorrhoeae, Treponema pallidum, Bacillus anthracis, Salmonella typhi, Vibrio cholera, Pasteurella pestis, Pseudomonas aeruginosa, Campylobacter jejuni, Clostridium difficile, Clostridium botulinum, Mycobacterium tuberculosis, Borrelia burgdorferi, Haemophilus ducreyi, Corynebacterium diphtheria, Bordetella pertussis, Bordetella parapertussis, Bordetella bronchiseptica, Haemophilus influenza*, and enterotoxic *Escherichia coli*.

The immunogen can further be an immunogen from a pathogenic protozoa, including, but not limited to, *Plasmodium* species (e.g., malaria antigens), *Babeosis* species, *Schistosoma* species, *Trypanosoma* species, *Pneumocystis carnii, Toxoplasma* species, *Leishmania* species, and any other protozoan pathogen now known or later identified.

The immunogen can also be an immunogen from pathogenic yeast and fungi, including, but not limited to, *Aspergillus* species, *Candida* species, *Cryptococcus* species, *Histoplasma* species, *Coccidioides* species, and any other pathogenic fungus now known or later identified.

Other specific examples of various immunogens include, but are not limited to, the influenza virus nucleoprotein (residues 218-226; Fu et al. (1997) *J. Virol.* 71: 2715-2721), antigens from Sendai virus and lymphocytic choriomeningitis virus (An et al. (1997) *J. Virol.* 71: 2292-2302), the B1 protein of hepatitis C virus (Bruna-Romero et al. (1997) *Hepatology* 25: 470-477), gp 160 of HIV (Achour et al. (1996) *J. Virol.* 70: 6741-6750), amino acids 252-260 of the circumsporozoite protein of *Plasmodium berghei* (Allsopp et al. (1996) *Eur. J. Immunol.* 26: 1951-1958), the influenza A virus nucleoprotein (residues 366-374; Nomura et al. (1996) *J. Immunol. Methods* 193: 4149), the listeriolysin O protein of *Listeria monocytogenes* (residues 91-99; An et al. (1996) *Infect Immun.* 64: 1685-1693), the E6 protein (residues 131-140; Gao et al. (1995) *J. Immunol.* 155: 5519-5526) and E7 protein (residues 21-28 and 48-55; Bauer et al. (1995) *Scand. J. Immunol.* 42: 317-323) of human papillomavirus type 16, the M2 protein of respiratory syncytial virus (residues 82-90 and 81-95; Hsu et al. (1995) *Immunology* 85: 347-350), the herpes simplex virus type 1 ribonucleotide reductase (Salvucci et al. (1995) *J. Gen. Virol.* 69: 1122-1131), the rotavirus VP7 protein (Franco et al. (1993) *J. Gen. Virol.* 74: 2579-2586), *P. falciparum* antigens (causing malaria) and hepatitis B surface antigen (Gilbert et al. (1997) *Nature Biotech.* 15: 1280-1283).

The immunogen can also be an immunogen from chronic or latent infective agents, which typically persist because they fail to elicit a strong immune response in the subject. Illustrative latent or chronic infective agents include, but are not limited to, hepatitis B, hepatitis C, Epstein-Barr Virus, herpes viruses, human immunodeficiency virus, and human papilloma viruses.

The invention can be practiced to induce an immune response to, and optionally to treat or to prevent infection (i.e., prophylactic treatment) from any infectious agent, including but not limited to those identified above.

Suitable transplantation immunogens include, but are not limited to, different antigenic specificities of HLA-A, B and C Class I proteins. Different antigenic specificities of HLA-DR, HLA-DQ, HLA-DP and HLA-DW Class II proteins can also be used (WHO Nomenclature Committee, *Immunogenetics* 16:135 (1992); Hensen et al., in *Fundamental Immunology*, Paul, Ed., pp. 577-628, Raven Press, New York, 1993; NIH Genbank and EMBL data bases).

The immunogen can further be an allergen. Exemplary food, animal, tree, insect and mold allergens are found at http://www.allergen.org/List.htm Marsh and Freidhoff. 1992. ALBE, an allergen database. IUIS, Baltimore, Md., Edition 1.0).

The immunogen can further be an autoantigen (for example, to enhance self-tolerance to an autoantigen in a subject, e.g., a subject in whom self-tolerance is impaired). Exemplary autoantigens include, but are not limited to, myelin basic protein, islet cell antigens, insulin, collagen and human collagen glycoprotein 39, muscle acetylcholine receptor and its separate polypeptide chains and peptide epitopes, glutamic acid decarboxylase and muscle-specific receptor tyrosine kinase.

The invention also encompasses methods of producing an immune response in a subject, the method comprising: administering a viral vector of the invention, a nucleic acid encoding the same, a virus particle comprising either of the foregoing, or a pharmaceutical formulation of the invention to a subject in an immunogenically effective amount so that an immune response is produced in the subject. The immune response can be directed against one or more of the structural proteins from the second virus (e.g., a capsid protein and/or an envelope glycoprotein). Optionally, the second virus is a pathogenic virus, and an immune response is induced against a structural protein from the pathogenic second virus.

Alternatively, the virion can comprise a modified structural protein from the second virus that presents a heterologous (i.e., foreign) immunogenic protein or peptide as described herein, and an immune response is produced against the heterologous immunogen. According to this aspect of the invention, the virion can comprise a fusion protein comprising the immunogenic peptide or protein fused to a virion structural protein. Optionally, the immunogenic peptide or protein is from a structural protein (e.g., an envelope protein) of a virus that is different from the second virus (and may be different from the carrier virus).

In other embodiments, the modified RNA genome comprises a heterologous nucleic acid encoding an immunogenic protein or peptide that is expressed independently of the structural proteins (i.e., is not fused to a structural protein), and an immune response is induced in the subject against the immunogenic peptide or protein.

In particular embodiments, the immune response is produced against a pathogenic organism or virus, and the pathogenic effects by administration of the chimeric viral vector or virus particle are less than would be produced by administering the live pathogenic organism or virus to the subject.

The viral vaccine can be given as a single dose schedule or in a multiple dose schedule. A multiple dose schedule is one in which a primary course of administration may consist of about 1 to 10 separate doses, followed by other doses (i.e., booster doses) given at subsequent time intervals to maintain and/or reinforce the immune response, for example, at about 1 to 4 months for a second dose, and if needed, a subsequent dose(s) after another several months. The dosage regimen will also, at least in part, be determined by the need of the individual and be dependent upon the judgment of the medical or veterinary practitioner.

Any suitable method of producing an immune response (i.e., immunization) known in the art can be employed in carrying out the present invention, as long as an active immune response (preferably, a protective immune response) against the antigen is elicited.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease, the progression of the disease and/or the symptoms of the disease. Alternatively, a protective immune response or protective immunity may be useful in the treatment of disease including infectious disease and cancer or tumors (e.g., by causing regression of a cancer or tumor and/or by preventing metastasis and/or by preventing growth of metastatic nodules). The protective effects may be complete or partial, as long as the benefits of the treatment outweigh any disadvantages thereof.

Vaccination can be by any means known in the art, including oral, rectal, topical, buccal (e.g., sub-lingual), vaginal, intra-ocular, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transmucosal, intratracheal, transdermal, intraventricular, intraarticular, intrathecal and inhalation administration, administration to the liver by intraportal delivery, as well as direct organ injection (e.g., into the liver, into the brain for delivery to the central nervous system, into the pancreas). Alternatively, administration can be by implant or injection into or near a tumor. In the case of an animal subject, injection may be into the footpad. Local administration (e.g., a depot or patch) can also be used.

The most suitable route in any given case will depend on the nature and severity of the condition being treated and on the viral vector, nucleic acid, virus particle, or pharmaceutical formulation being administered.

The viral vectors, nucleic acids and virus particles of the invention can be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the viral vector, nucleic acid or virus particle is typically admixed with, inter alla, an acceptable carrier. The carrier can be a solid or a liquid, or both, and is optionally formulated as a unit-dose formulation, which can be prepared by any of the well-known techniques of pharmacy.

For injection, the carrier is typically a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the viral vector, nucleic acid or viral particle can be administered in solid dosage forms, such as capsules, tablets, and powders, or in liquid dosage forms, such as elixirs, syrups, and suspensions. The viral vector, nucleic acid or viral particle can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the viral vector, nucleic acid or viral particle in a flavored base, usually sucrose and acacia or tragacanth; and pastilles comprising the viral vector, nucleic acid or viral particle in an inert base such as gelatin and glycerin or sucrose and acacia.

Formulations of the present invention suitable for parenteral administration can comprise sterile aqueous and non-aqueous injection solutions of the viral vector, nucleic acid or viral particle, which preparations are generally isotonic with the blood of the intended recipient. These preparations can contain anti-oxidants, buffers, bacteriostats and solutes, which render the formulation isotonic with the blood of the intended recipient. Aqueous and non-aqueous sterile suspensions can include suspending agents and thickening agents. The formulations can be presented in unitdose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets. For example, in one aspect of the present invention, there is provided an injectable, stable, sterile composition comprising a viral vector, nucleic acid or virus particle of the invention, in a unit dosage form in a sealed container. Optionally, the composition is provided in the form of a lyophilizate. which is capable of being reconstituted with a suitable pharmaceutically acceptable carrier to form a liquid composition suitable for injection thereof into a subject.

Formulations suitable for rectal or vaginal administration can be presented as suppositories. These can be prepared by admixing the viral vector, nucleic acid or viral particle with one or more conventional excipients or carriers, for example, cocoa butter, polyethylene glycol or a suppository wax, which are solid at room temperature, but liquid at body temperature and therefore melt in the rectum or vaginal cavity and release the viral vector, nucleic acid or viral particle.

Formulations suitable for topical application to the skin can take the form of an ointment, cream, lotion, paste, gel, spray, aerosol, or oil. Carriers that can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, *Pharmaceutical Research* 3 (6):318 (1986)) and typically take the form of an optionally buffered aqueous solution. Suitable formulations comprise citrate or bis\tris buffer (pH 6) or ethanol/water.

The viral vector, nucleic acid or viral particle can be formulated for nasal administration or otherwise administered to the lungs of a subject by any suitable means, for example, by an aerosol suspension of respirable particles comprising the viral vector, nucleic acid or virus particle, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al. (1992) *J. Pharmacol. Toxicol. Methods* 27:143-159. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the viral vector, nucleic acid or virus particle can likewise be produced with any solid particulate medicament aerosol generator, by techniques known in the pharmaceutical art.

Alternatively, one can administer the viral vector, nucleic acid or viral particle in a local rather than systemic manner, for example, in a depot or sustained-release formulation.

In particular embodiments of the invention, administration is by subcutaneous or intradermal administration. Subcutaneous and intradermal administration can be by any method known in the art, including but not limited to injection, gene gun, powderject device, bioject device, microenhancer array, microneedles, and scarification (i.e., abrading the surface and then applying a solution comprising the viral vector, nucleic acid, or virus particle).

In other embodiments, the viral vector, nucleic acid or viral particle is administered intramuscularly, for example, by intramuscular injection or by local administration.

Nucleic acids can also be delivered in association with liposomes, such as lecithin liposomes or other liposomes known in the art (for example, as described in WO 93/24640) and may further be associated with an adjuvant. Liposomes comprising cationic lipids interact spontaneously and rapidly with polyanions, such as DNA and RNA, resulting in liposome/nucleic acid complexes that capture up to 100% of the polynucleotide. In addition, the polycationic complexes fuse with cell membranes, resulting in an intracellular delivery of polynucleotide that bypasses the degradative enzymes of the lysosomal compartment. PCT publication WO 94/27435 describes compositions for genetic immunization comprising cationic lipids and polynucleotides. Agents that assist in the cellular uptake of nucleic acid, such as calcium ions, viral proteins and other transfection facilitating agents, may advantageously be included.

Polynucleotide immunogenic preparations may also be formulated as microcapsules, including biodegradable time-release particles. U.S. Pat. No. 5,151,264 describes a particulate carrier of phospholipid/glycolipid/polysaccharide nature that has been termed Bio Vecteurs Supra Moleculaires (BVSM).

Particular embodiments of the present invention are described in greater detail in the following non-limiting examples.

EXAMPLE 1

Formation of Gag Particles After Infection with GAG-VRP

A live, attenuated, self-replicating virus vaccine for induction of protective neutralizing antibodies and cell-mediated immunity to the major antigens of an immunodeficiency virus has been developed. The vaccine employs a disabled Venezuelan equine encephalitis (VEE) replicon RNA to direct the assembly of extracellular Gag/Env chimeric particles capable of packaging replicon RNA for delivery to another cell. As VEE replication is very sensitive to interferon and does not involve integration into chromosomes, this replicating entity is considered safe for use in vivo because the chimeric virus vaccine is cleared by the mounting immune response to the immunogens. This instant vaccine conserves the aspects of a live virus vaccine without the inherent safety concerns surrounding live attenuated lentivirus mutants.

Figure 2A:
Figure 2B:
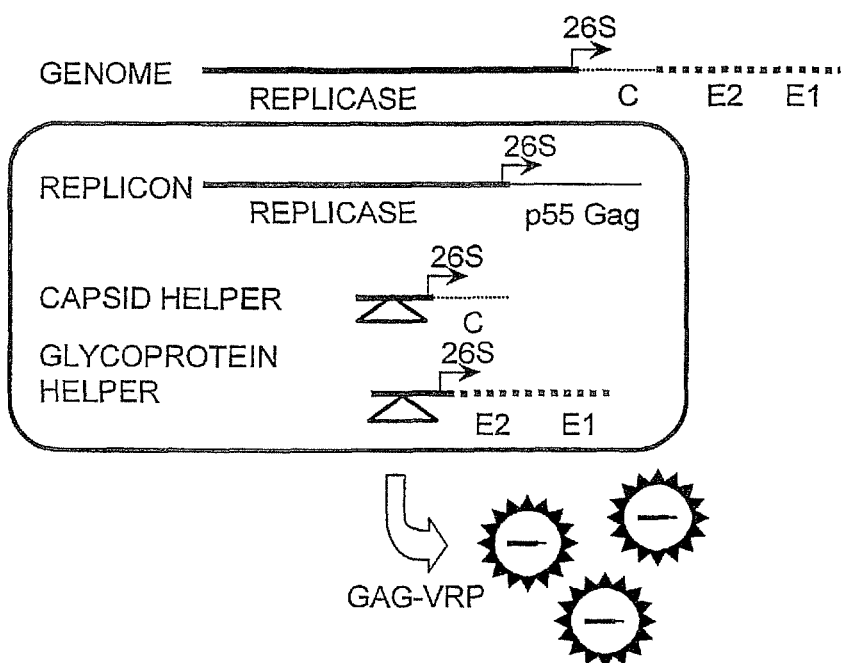

VEE is a member of the family Togaviridae. This enveloped virus has a (+)ssRNA genome encoding capsid protein (C), E1 glycoprotein, and E2 glycoprotein as well as non-structural proteins, nsP1-4 (FIG. 1). The parental genome is replicated via (−)strand synthesis, which subsequently serves as a template for generation of the progeny genome as well as the 26S subgenomic mRNA encoding C, E1, and E2. Toward the generation of self-replicating VEE replicon particles (VRP) for inducing antibodies and cell-mediated immunity to the major antigens of HIV, the full-length SIVsmH4 Gag protein from simian immunodeficiency virus (SIV) was inserted downstream of the VEE 26S promoter (FIG. 2A). A schematic of replicon packaging of the p55 Gag protein is depicted in FIG. 2B. The full-length SIVsmH4 Gag protein was expressed from Gag-VRP replicons in amounts sufficient to drive formation of budding Gag containing particles. FIG. 2C and FIG. 2D show concentrated supernatants from Vero cells infected with Gag-VRP stained with uranyl acetate and lead citrate and observed in TEM. Budding particles were observed in thin sections of Gag-VRP infected cells (FIG. 2E), and these were positive when stained with anti-Matrix antibodies and a secondary antibody conjugated with 5 nm gold beads. The particles were consistent with immature lentivirus particles in size and morphology. It was concluded that the VEE replicons produced sufficient Gag to drive assembly of virus-like particles in cells of primate origin. An analogous result was obtained in infection of mouse embryo fibroblasts. Assembly of extracellular Gag particles in cells of rodent origin is thought to occur inefficiently if at all, indicating that in these cells, production of Gag from the VEE replicon is at a very high level that overcomes any species inhibition of assembly.

EXAMPLE 2

Packaging of VEE Replicon RNA into Gag Particles

Figure 3A:
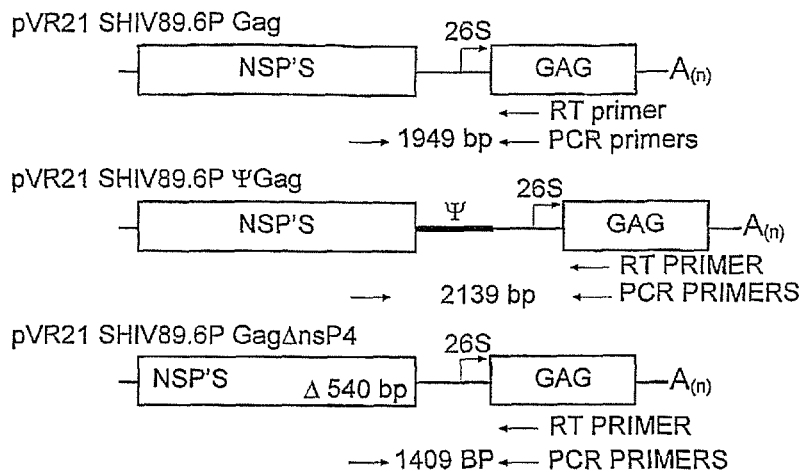
FIGS. 3A and 3B show that Gag particles produced in Gag VPR- and ψGag VRP-infected Vero cells.

It has been shown that retroviral Gag proteins promiscuously package any available cytoplasmic RNA into chimeric particles. As replicon RNAs are the most abundant RNAs in the cytoplasm of Gag-VRP infected cells, the presence of such RNAs in the extracellular chimeric particles was determined. For this analysis, the gag gene from the KB-9 clone of SHIV89.6P was employed (FIG. 3A).

Figure 3B:
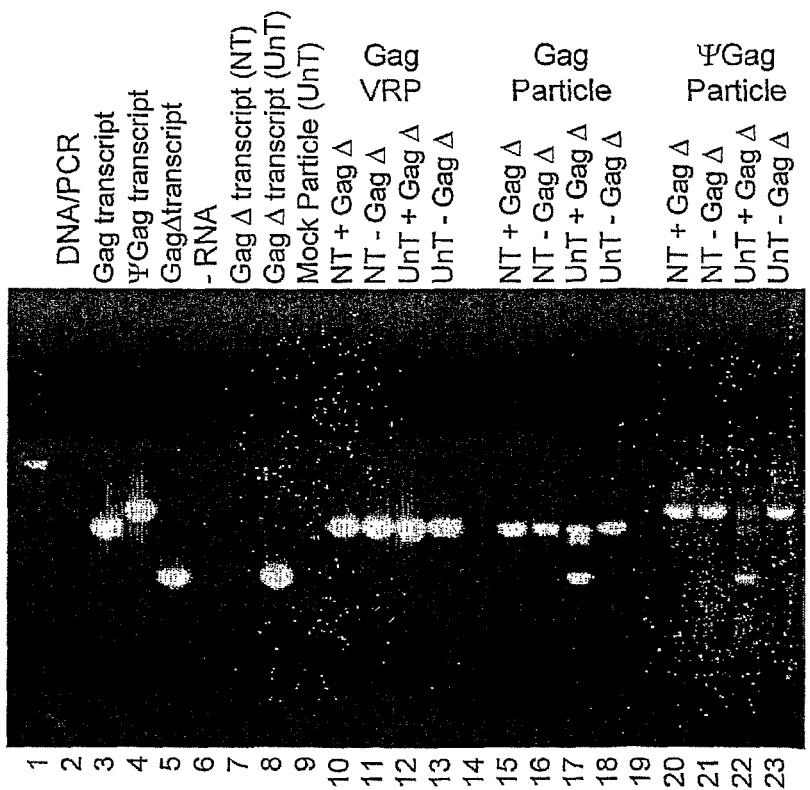

Vero cells were infected with Gag-VRP, and Gag-containing chimeric particles were harvested by centrifugation of the culture supernatant through a 20% sucrose cushion. This preparation was either treated or not treated with micrococcal nuclease to remove unencapsidated RNA. RNA was extracted from the chimeric particles using a QIMMP® Viral RNA kit (QIAGEN®, Valencia, Calif.), and RT-PCR was used to detect the nuclease resistant RNA as shown in FIG. 3A. The RT primer was within the gag gene, and the PCR reverse primer was upstream in nsP4. The results are shown in FIG. 3B. The chimeric particles that budded from cells following Gag-VRP infection contained Gag replicon RNA in a nuclease resistant form as demonstrated by resistance to degradation by nuclease. Gag-VRP particles themselves served as a control for nuclease resistant encapsidation of the Gag replicon RNA.

A control RNA was added to the particle preparations to monitor the effectiveness of the nuclease treatment. The control RNA was Gag replicon RNA with a 540 nucleotide deletion in nsP4 interior to the diagnostic RT-PCR product (FIG. 3A). Therefore, a shorter RT-PCR product (1409 bp) from this control RNA was distinguishable from the packaged full-length RNA (1949 bp) (FIG. 3B, lane 5). The control RNA was fully digested, confirming that the nuclease digestion was effective in removing RNA outside the particles and that the Gag replicon RNA was contained inside the chimeric particles in a nuclease resistant form (FIG. 3B, lanes 15 and 17).

EXAMPLE 3

VEE Replicon RNA Expressing Env

Figure 4A:
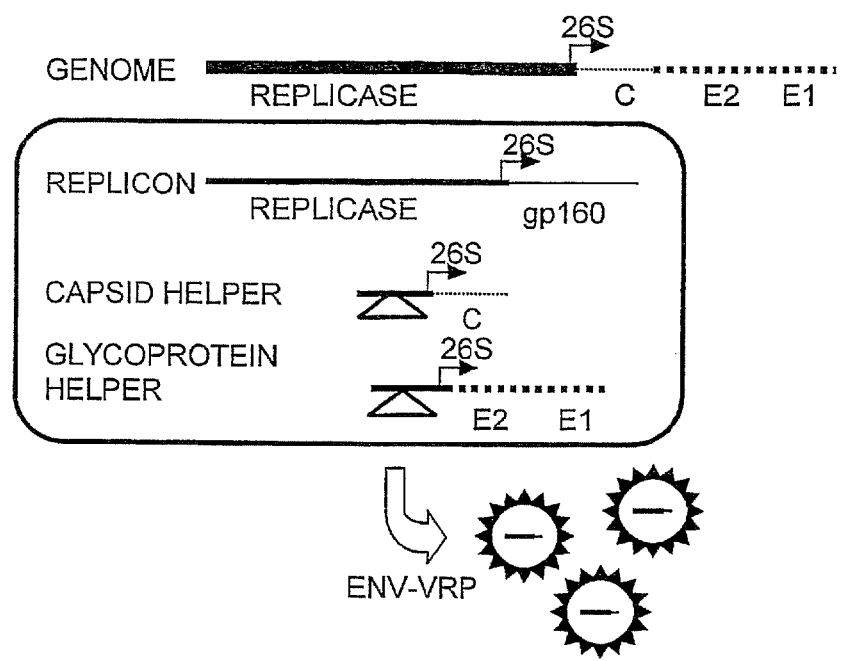
FIGS. 4A and 4B show the production of Env-VRP by expressing Env from VEE replicon RNA.
Figure 4B:
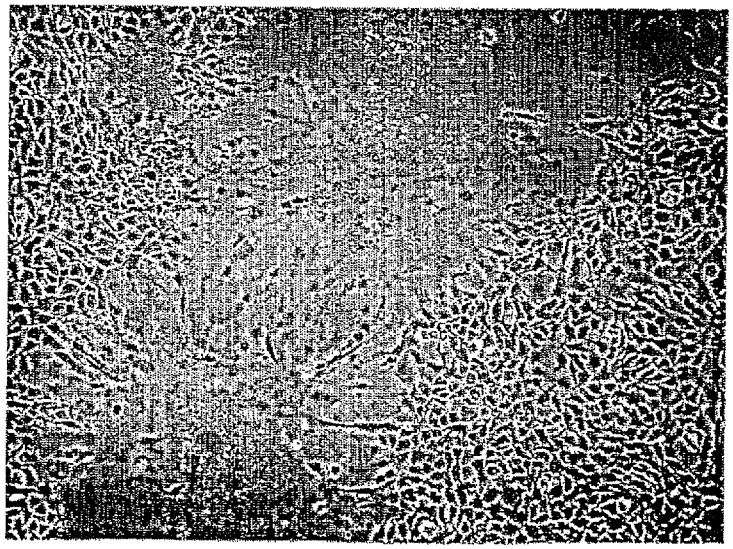

As with Gag, a full-length Env protein was inserted downstream of the VEE 26S promoter. A schematic of replicon packaging of the gp160 Env protein is depicted in FIG. 4A. The full-length Env protein was expressed from Env-VRP replicons and the Env produced in these infections was biologically active, as syncytia were produced in chimeric particle-infected 3T3-CD4-CCR5 (FIG. 4B). and MAGI cells but not in control cells lacking CD4 and CCR5. Similarly, giant cells were formed after infection of CEMx174 cells. These findings provided a means of quantitating infectious chimeric particles, as the syncytia were visible to the unaided eye after staining of the infected monolayer of 3T3-CD4-CCR5 cells, and they could be enumerated by counting as "plaques". In this regard, a quantitative assay of biologically active chimeric particles was developed. Eight-well chamber slides were seeded with 3T3-CD4-CCR5 cells and then infected with a 2-fold dilution series. The number of syncytia present in each well were quantified by indirect IFA. Undiluted particles generally produced approximately 5-10 syncytia in a well.

In an alternative quantitative assay, syncytia were visualized on a monolayer that was infected with dilutions of a chimeric particle preparation, then overlaid with agarose and monitored for development of syncytia. Assuming that each syncytium was initiated by a single infectious chimeric particle, syncytia could be counted in a standard plaque assay. In this regard, 3T3-CD4-CCR5 cells were mock infected or infected with either Env-VRP or with undiluted GagEnv and EnvGag chimeric particles, and stained with crystal violet 24 hpi. During the evaluation of this assay, it was found that an agarose overlay was not necessary and the plaques in the GagEnv- and EnvGag-infected monolayers while detectable, were consistently smaller than the Env-VRP-infected monolayers.

EXAMPLE 4

SIV ψGag-VRP

Incorporation of retroviral RNA into virions occurs by the specific recognition of an RNA packaging signal by the nucleocapsid (NC) domain of Gag. For retroviruses, the 4' packaging signal is composed of one or more stem-loop structures located in the 5' LTR. For HIV-1, ψ is composed primarily of four stem-loop structures at the 3' end of the 5' LTR and extending into the Gag coding sequence (Clever, et al. (2002) *J. Virol.* 76:12381-12387). Stem-loop 3 has been shown to directly interact with NC and stem-loops 1 and 4 appear to be more important than stem-loop 2 for RNA packaging. The SIV 4' sequence has not been precisely defined; however, similar stem-loop structures to that of HIV-1 have been predicted using Zucker's MFOLD program (Guan, et al. (2000) *J. Virol.* 74:8854-8860; Guan, et al. (2001) *J. Virol.* 75:2776-2785). Deletion analysis has suggested that sequences within these stem-loop structures are important for RNA packaging, in particular nucleotides 371-418.

Figure 5:
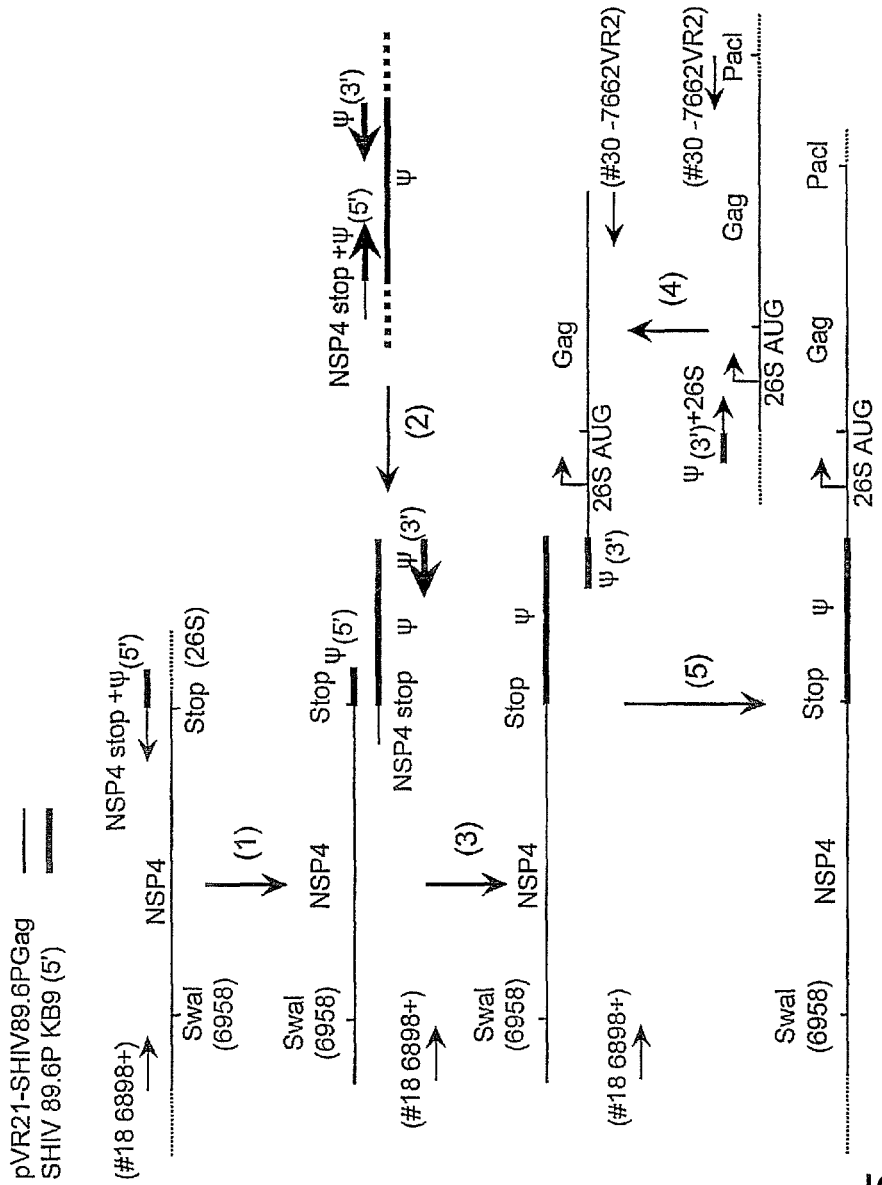
FIG. 5 depicts the construction of pVR21 SHIV89.6P Gag containing a putative SIV ψ sequence (pVR21 SHIV89.6P ψGag).

To engineer an SIV RNA packaging signal into the VEE replicon, all four stem-loop structures were incorporated, which included nucleotides 371-562 from the SHIV 89.6P KB9 molecular clone. The PCR strategy used to insert the 4' sequence into SHIV89.6P Gag is shown in FIG. 5. All of the PCR reactions were successful and the appropriate size band for each reaction was obtained. The final PCR product and SHIV89.6P Gag were digested with SwaI and PacI, the restriction fragments agarose gel were purified, and Gag with the 4' sequence and 26S promoter was ligated into the pVR21 vector. Colony PCR was performed to screen for positive clones and positive clones were verified by restriction diagnostics and DNA sequencing.

Figure 6A:
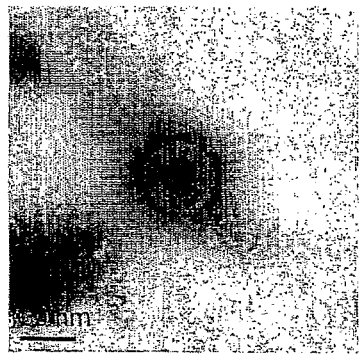
FIGS. 6A and 6B show expression of Gag from SHIV89.6P Gag and ψ Gag replicon RNA and particle formation.
Figure 6B:
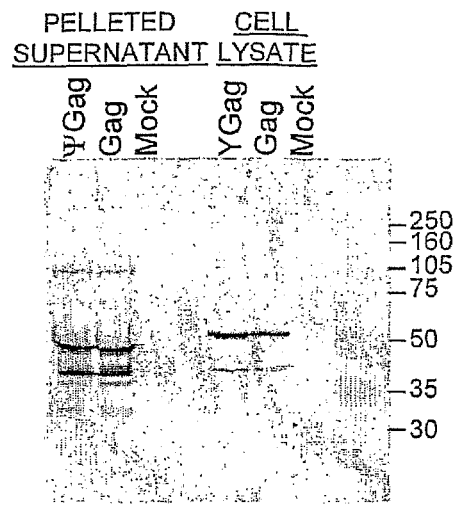
Figure 7A:
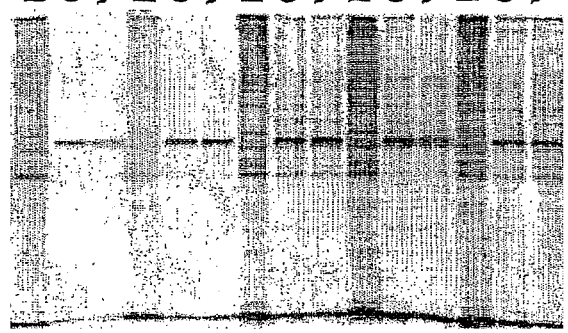
FIGS. 7A and 7B show that the packaging signal introduced into Gag replicon RNA does not affect translation of Gag. Vero cells were mock-infected or infected with Gag or ψGag VRP at a multiplicity of infection (MOI) of 10 for 1 hour (in duplicate). At 3 hours post-infection (hpi), the cells were starved for 1 hour, and $^{35}$S PROMIX™ (Met/Cys, 48 mCi/mL) was added. The first time point was taken 2 hours after the addition of label (6 hpi). At 6, 10, 14, 18 and 22 hpi, culture media was transferred to microfuge tubes and the cells were lysed with NP-40. The amount of Gag present in cell lysates (FIG. 7A) and culture supernatants (FIG. 7B) was determined by 10% SDS-PAGE and phosphorimager (PI) analysis.
Figure 7A:
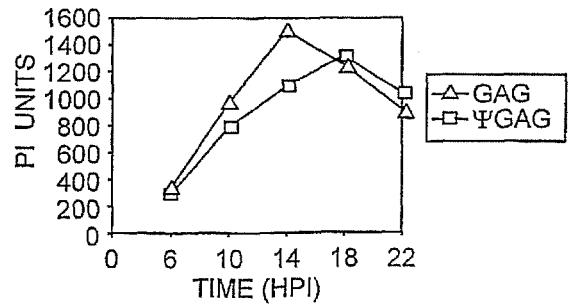
Figure 7B:
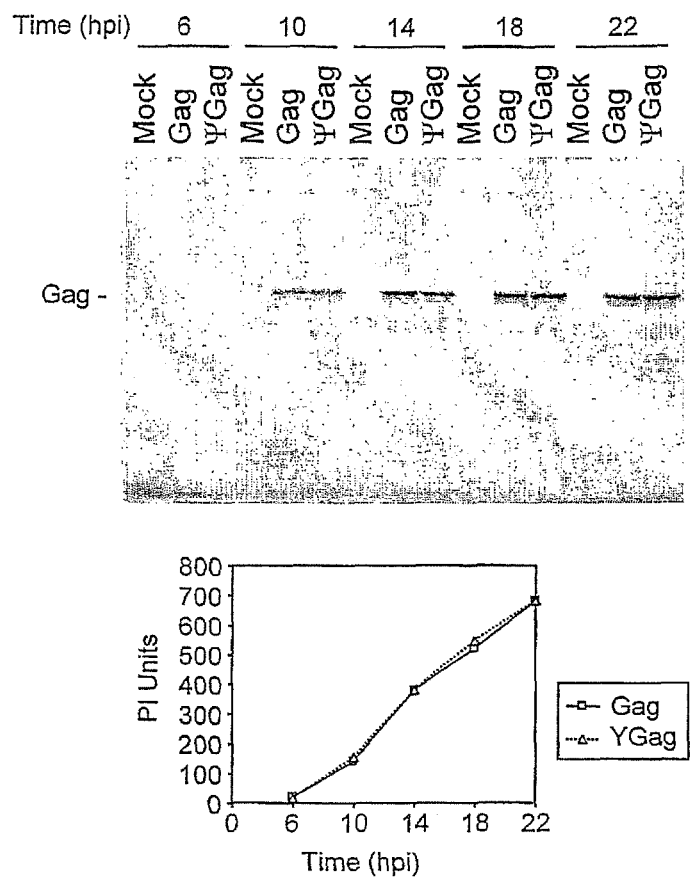

Gag replicons containing the putative SIV 4' sequence were electroporated into Vero cells, particles were released into the cell culture supernatants and concentrated by pelleting through 20% sucrose. As shown in FIG. 6A, immature Gag-containing particles were assembled and released by expressing Gag from the VEE replicon RNA in primate cells. Gag expression from ψGag replicon RNA was verified by western blot analysis. RNA transcribed from linearized Gag and ψGag plasmid DNA was electroporated into Vero cells. After 20 hours, the supernatants were concentrated by centrifugation through a 20% sucrose cushion, and the cells were lysed with NP-40 lysis buffer. Samples of Mock, Gag and ψGag cell lysates and concentrated supernatants were separated by 10% SDS-PAGE, transferred to PVDF membrane and probed with anti-SHIV monkey sera (FIG. 6B). Gag expression from the ψGag replicon was similar to expression from the Gag replicon both in culture supernatants and cytoplasmic lysates, indicating that the ψ packaging sequence did not adversely affect translation or replication of replicon RNA (FIG. 7). Ribonuclease protection experiments, to demonstrate equivalent synthesis of genomic (+) and (−) strand RNAs and subgenomic mRNA, are performed to insure that the packaging signal does not affect transcription and replication, but an effect of ψ seems unlikely as equivalent amounts of Gag particles were produced with and without ψ.

Figure 8A:
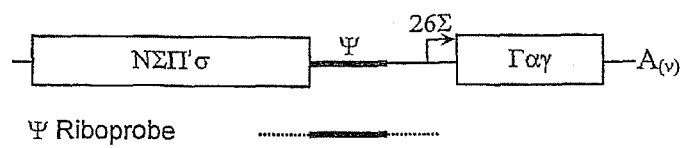
FIGS. 8A-8C demonstrate a northwestern blot of Gag-ψ sequence interactions.
Figure 8B:
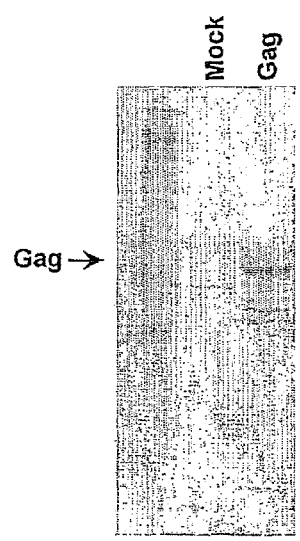
Figure 8C:
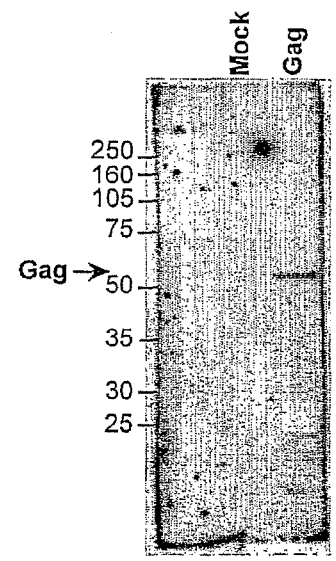

To evaluate the binding of putative SIV ψ-containing RNA to Gag, templates for the production of riboprobes containing the putative SIV ψ sequence were constructed such that the ψ sequence was flanked by approximately 100 nucleotides of VEE sequence on either end (FIG. 8A). These sequences were placed downstream of a T7 promoter so that a genome, sense, $^{32}$P-labeled riboprobe could be synthesized in vitro. Vero cells were infected with Gag-VRP or mock infected, the cells were lysed with NP-40, Gag was immunoprecipitated with anti-SHIV89.6P monkey serum, and the immunoprecipitate was separated by SDS-PAGE. The separated protein was blotted to a nitrocellulose membrane. A portion of the membrane was probed with anti-Gag antibodies to confirm the presence of Gag protein and to determine its position in the gel (FIG. 8B). The remainder of the membrane, containing both mock and Gag-VRP infected lanes, was probed with the $^{32}$P-ψ-containing riboprobe. A band co-migrating with Gag was evident in the Gag-VRP lysate but not in the lysate from the mock-infected control cells (FIG. 8C). These data indicate that the putative ψ sequence is indeed capable of binding to Gag. As controls, riboprobes including an analogous riboprobe lacking ψ, an anti-sense ψ probe, and a cyclophilin riboprobe are employed. Further, lysates from cells infected with an irrelevant VRP are used as controls.

Figure 9:
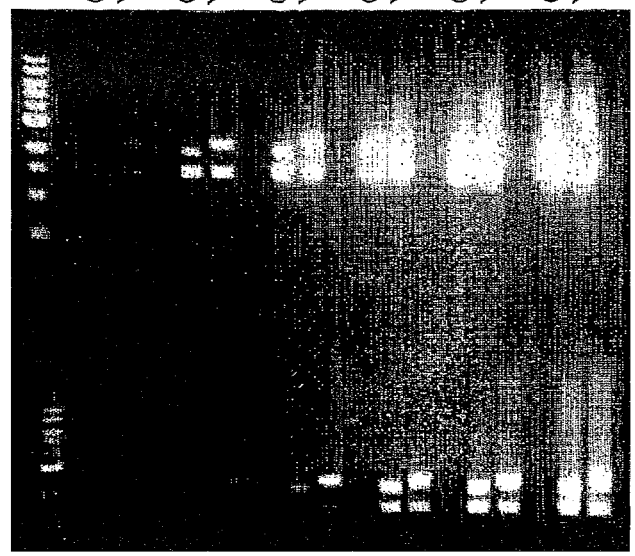
FIG. 9 shows competitive qRT-PCR analysis to measure replicon RNA packaged into Gag particles. Concentrated supernatants from Gag and ψGag VRP-infected Vero cells were treated with micrococcal nuclease. After nuclease treatment, the RNA from Gag particles was extracted (target RNA) and mixed with GagΔNSP4 RNA (competitor RNA) diluted to either 1:2500 (top) or 1:5000 (bottom). The RNAs were reverse-transcribed (RT) in the same reaction and a portion of the RT reaction was used for PCR amplification. Aliquots were removed at 15, 17, 19, 21, 23 and 25 cycles to determine the cycles that were in exponential phase of amplification. The PCR products were separated on a 0.8% TAE gel and visualized by ethidium bromide staining.
Figure 10A:
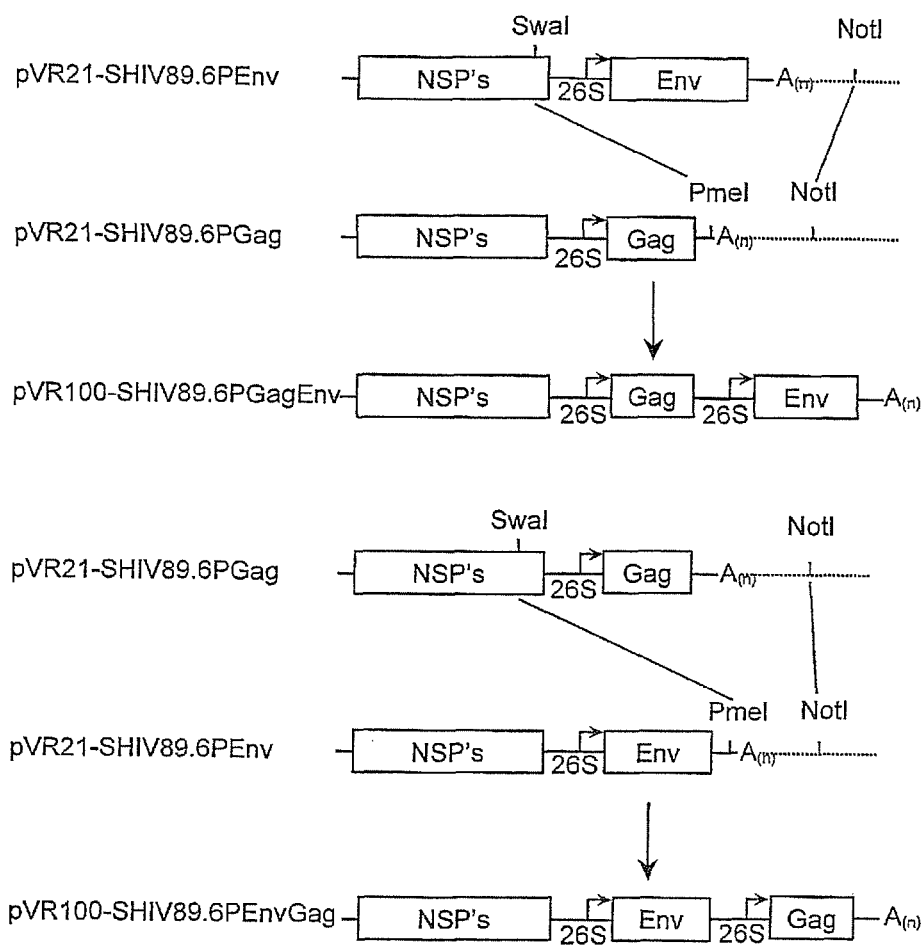
FIGS. 10A-E show coexpression of Gag and Env.
Figure 10B:
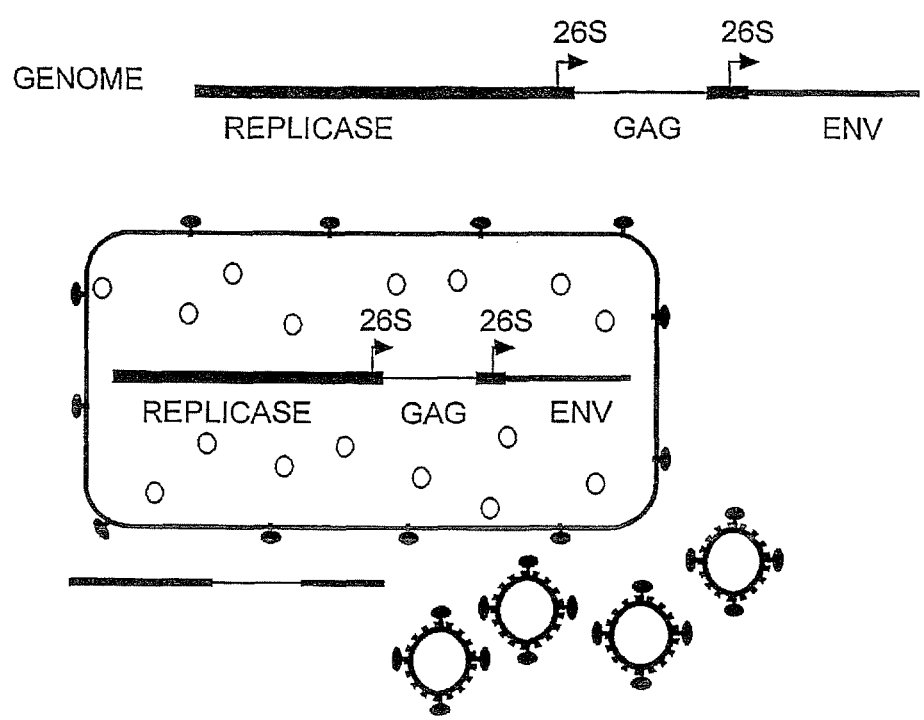
Figure 10C:
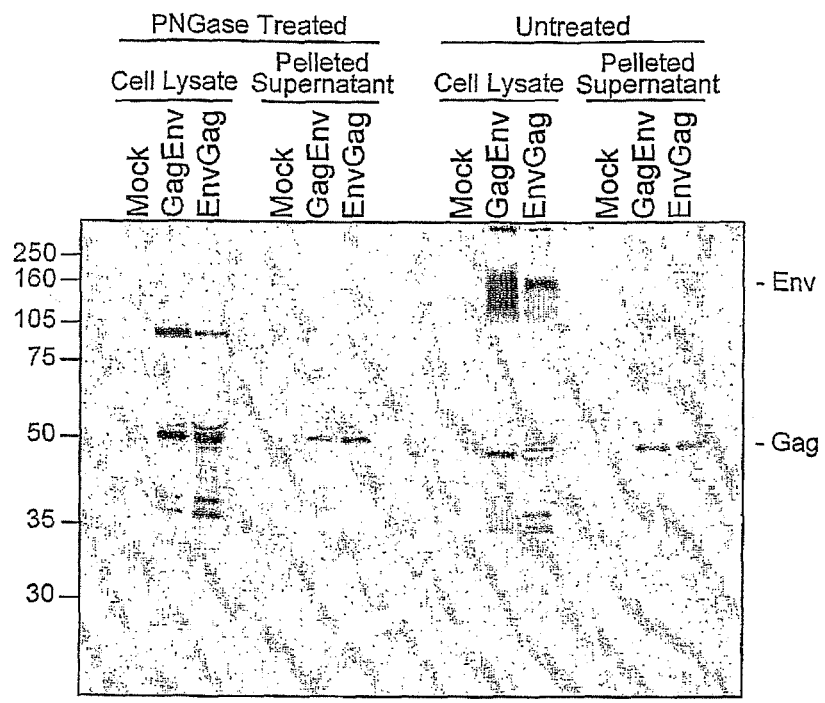
Figure 10D:
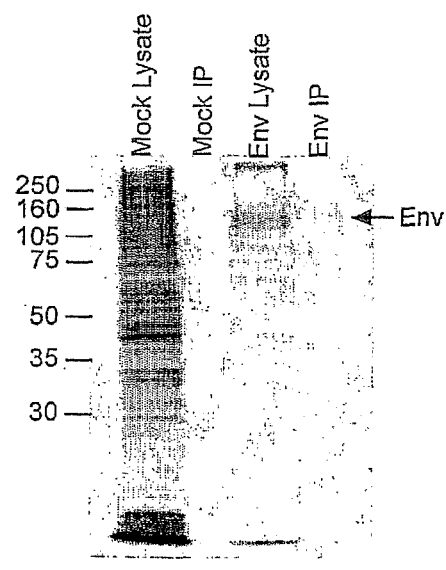
Figure 10E:
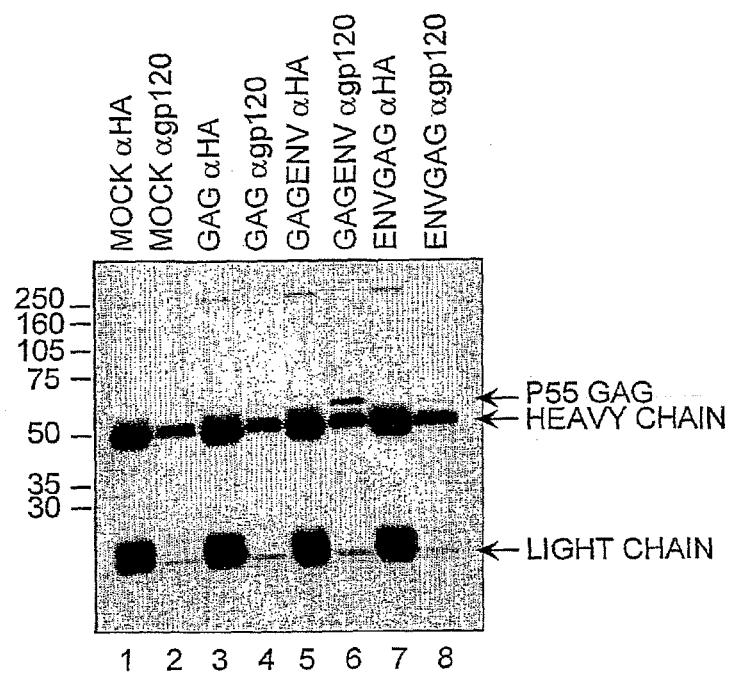
Figure 11A:
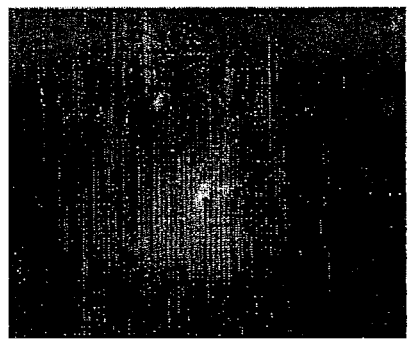
FIGS. 11A-F show the formation of multinucleate giant cells in GagEnv-infected (FIGS. 11A-11D) and EnvGag-infected (FIGS. 11E-11F) CEM cultures.
Figure 11B:
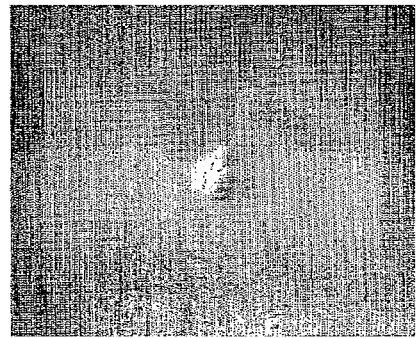
Figure 11C:
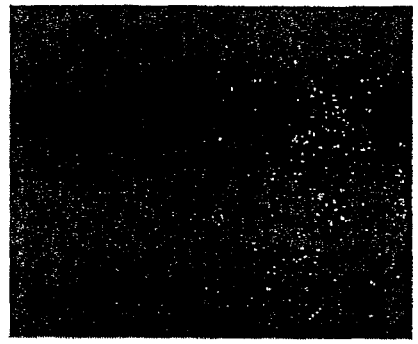
Figure 11D:
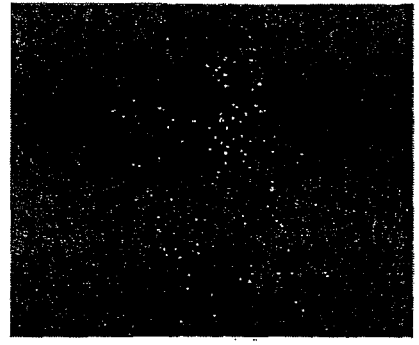
Figure 11E:
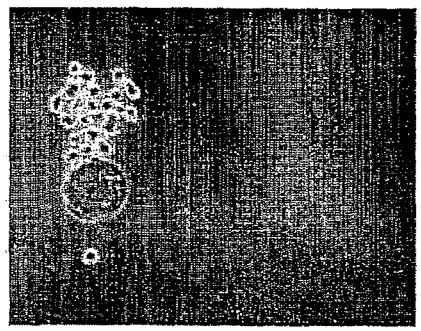
Figure 11F:

The relative efficiency of Gag replicon RNA packaging with and without ψ was subsequently evaluated. A competitive, quantitative RT-PCR assay was developed to determine if Gag chimeric particles preferentially package replicon RNA containing the putative SIV packaging signal (FIG. 9). In this assay, two RNAs are present in the RT-PCR reaction, the target RNA to be quantitated (Gag or ψGag replicon RNA), and a known amount of competitor RNA (pVR21SHIV89.6P GagΔnsP4). See FIG. 3A for location of primers. The two RNAs should compete equally well for reagents in the RT-PCR reaction, and the ratio of competitor to target after PCR amplification reflects the initial ratio of the two RNAs when determined during the exponential phase of PCR amplification. The amount of target RNA is then quantitated by direct comparison to the amount of competitor RNA after PCR amplification. The competitor also serves as an internal control for input RNA. In this analysis, concentrated supernatants from Gag- or ψGag-VRP infected Vero cells were treated with micrococcal nuclease. After nuclease treatment, the RNA from Gag chimeric particles was extracted using the QIAAMP® Viral RNA extraction kit. GagΔnsP4 was transcribed in vitro using the AMBION® mMESSAGE® kit, DNAse treated, and quantitated by spectrophotometry. The RNA was then diluted either 1:2500 or 1:5000 and added to the target RNAs. The target and competitor RNAs were reverse-transcribed in the same reaction using SUPERSCRIPT™ III (INVITROGEN™, Carlsbad, Calif.), and a portion of the RT reaction was used for PCR amplification. Aliquots were removed at 15, 17, 19, 21, 23 and 25 cycles to determine the cycles that are in exponential phase of amplification. In this particular assay, the quantity of chimeric particles from Gag VRP-infected and ψgag VRP-infected cells was not determined prior to nuclease treatment and RNA extraction. However, the results (at 15, 17 and 19 cycles) indicate that the ψGag replicon was preferentially packaged (FIG. 9).

To determine whether Gag replicon RNA containing the putative SIV ψ packaging signal is preferentially packaged over replicon RNA without the signal, RNA extracted from Gag chimeric particles produced in Vero cells co-infected with Gag- and ψGag-VRP are analyzed by the competitive qRT-PCR assay described above. In the setting of a co-infection, if the Gag replicon RNA containing the putative SIV ψ packaging signal is preferentially packaged over replicon RNA without the signal, a stronger signal is observed for the ψGag replicon RNA compared to the Gag replicon RNA.

EXAMPLE 5

Particles Produced from Expression of Both Gag and Env

To create a self-replicating antigen expressing both SHIV 89.6P Gag and Env, double promoter replicons were designed. Gag and Env coding sequences obtained from SHIV89.6P molecular clone KB9 were cloned into pVR21 replicon plasmids. These plasmids were used to construct double promoter replicon plasmids that express Gag and Env from the same replicon. In one construct, Gag was expressed from the upstream promoter and Env was expressed from the downstream promoter (GagEnv). In the other construct, the order was switched and Env was expressed from the upstream promoter and Gag was expressed from the downstream promoter (EnvGag). Schematics of the cloning strategy and the replicons are shown in FIG. 10A. SwaI and NotI restriction enzymes were used to remove the 26S promoter and the Gag and Env coding sequences from SHIV89.6P Gag and Env plasmids, respectively. The restriction fragments were agarose gel-purified for ligation into SHIV89.6P Env and Gag plasmids digested with PmeI and NotI. Colony PCR and restriction diagnostics were used to identify positive clones. Positive clones were verified by DNA sequencing. The resulting VRPs produced using these constructs are depicted in FIG. 10B. While these constructs lack the ψ sequence, the specificity of RNA packaging (and perhaps the efficiency of uncoating in subsequent rounds of infection) may be significantly improved through the incorporation of ψ. Accordingly, the ψ sequence can be readily added to these replicon RNAs as described herein.

Expression of Gag and Env from the double promoter replicons was verified by western blot analysis (FIG. 10C). RNA transcribed from linearized GagEnv and EnvGag plasmid DNA was electroporated into Vero cells. After 24 hours, the cells were lysed with RIPA buffer and the supernatants were concentrated by centrifugation through a 20% sucrose cushion. A portion of the cell lysates and concentrated supernatant was treated with PNGase F, an amidase that removes N-linked glycan chains from glycoproteins. After PNGase treatment, treated and untreated samples were fractionated by 10% SDS-PAGE and transferred to a PVDF membrane for western blot analysis by probing with anti-SHIV monkey sera. De-glycosylated SHIV 89.6P Env is predicted to have a molecular weight of 99 kDa using NetNGlyc 1.0. The band migrating just below the 105 kDa marker in the PNGase F-treated cell lysate lanes corresponds with the predicted molecular weight of de-glycosylated SHIV 89.6P Env.

Both Gag and Env were detected in the cell lysates, indicating expression from both promoters. Gag was detected in the concentrated supernatants by western blot; however, Env was not readily detected in the concentrated supernatants. It is known that there are relatively low numbers of Env molecules present on the surface of lentivirus particles compared to the number of Gag molecules. Various reports have estimated the Gag:Env ratio to be 40-60:1. Therefore, western blot analysis may not be sensitive enough to detect Env on the population of chimeric particles present in the concentrated supernatants.

As indicated, Env was not readily detected in the concentrated supernatants from Vero cells expressing GagEnv and EnvGag replicon RNA. Moreover, Env was not readily detected in concentrated supernatants from 3T3-CD4-CCR5 cells expressing GagEnv and EnvGag replicon RNA as determined by western blot analysis. Therefore, a different approach was taken to detect Env on the surface of particles, Using a known monoclonal antibody to HIV-1 gp120, IgG1 b12, (NIH AIDS Research and Reference Program, catalog #2640), chimeric particles were immunoprecipitated from concentrated supernatants. To show that this antibody was able to immunoprecipitate SHIV89.6P gp120, Env was immunoprecipitated from metabolically labeled cell lysates infected with SHIV89.6P Env-VRP (FIG. 10D, lane 4). The anti-gp120 antibody should immunoprecipitate any chimeric particles that have incorporated gp120 or gp160 onto their surface. Immunoprecipitated particles can then be detected by western blot analysis using an anti-Gag antibody. Concentrated supernatants from 3T3-CD4-CCR5 cells transfected with Gag, GagEnv or EnvGag RNA were either immunoprecipitated with HIV-1 anti-gp120 b12 or with an irrelevant glycoprotein antibody, the influenza virus hemagglutinin antibody (anti-HA). The immunoprecipitated particles were then separated by 10% SDS-PAGE, transferred to a PVDF membrane and probed with anti-SIV Gag monoclonal antibody kk64 (NIH AIDS Research and Reference Program catalog #2321). As shown in FIG. 10E (lanes 6 and 8), Gag was detected in the anti-gp120-immunoprecipitated supernatants from cells transfected with GagEnv or EnvGag replicon RNA, but not in the immunoprecipitated supernatants from cells transfected with Gag replicon RNA (lane 4). The irrelevant anti-HA antibody did not co-immunoprecipitate Gag, indicating that immunoprecipitation of Gag was specific to the anti-gp120 antibody. These results indicate that gp160 or gp120 is on the surface of chimeric viral particles.

EXAMPLE 6

Infection of Cells with VRPs Expressing Both Gag and Env

To demonstrate that the chimeric GagEnv and EnvGag constructs could form multinucleated giant cells (MGCs), Vero cells were electroporated with RNA transcripts of the GagEnv and EnvGag replicon plasmids and incubated for 24 hours. Culture supernatants containing putative chimeric particles containing Gag, Env and the replicon RNA were harvested and clarified at low speed, followed by filtration through an 0.2 µm filter. Chimeric particles passing through the filter were pelleted by ultracentrifugation through a 20% sucrose cushion and resuspended. These were used to infect CEMx174 cultures. Four successive passages were performed in CEMx174 cells with the supernatants being filtered and concentrated through sucrose between each of the passages. Control, mock-infected cultures were carried in parallel. Observation of the cultures revealed the presence of low numbers of multinucleated giant cells in the "infected" cultures (FIGS. 11A-F). FIGS. 11A-11D show a multinucleated giant cell associated with multiple other cells that appear to be in the process of fusion. No such cells were observed soon after infection, but their numbers appeared to increase over time, to a maximum of approximately 50 per culture. An occasional larger cell was observed in the control cultures, but such cells were never as large as in the test cultures and did not contain multiple nuclei upon staining with DAPI. If present at all, there were no more than one or two of these per control culture.

These data indicate that a transmissible and filterable entity was capable of transferring fusion capability from one cell culture to the next. It is likely that replication of this entity occurred in the CEMx174 cells to some extent, as otherwise it likely would have been diluted in successive passages. Additional passage experiments, which omit the ultracentrifugation/concentration step, can be carried out to test the hypothesis that cell fusion results when cells are infected with a transmissible particle that then programs the synthesis of gp160 in sufficient quantity to mediate cell-cell fusion. No fusion of electroporated Vero cells was observed, as these cells do not have the human CD4 and CCR5 co-receptors.

The replication of the transmissible particle appeared to be very inefficient in CEMx174 cells. This could result from the fact that the genome of these chimeric particles is an alphavirus replicon, and alphavirus RNA replication in lymphocytes may be limited by intracellular factors or the lack thereof. Therefore, infection of MAGI cells was performed using HeLa cells expressing the human CD4 and CCR5 co-receptors.

Figure 12A:
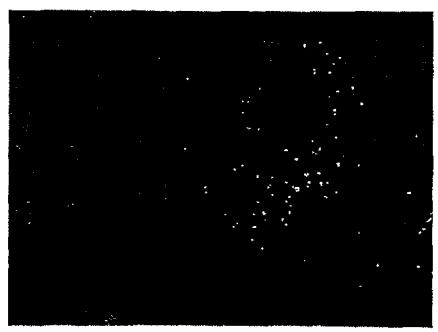
FIGS. 12A-D show infection of MAGI cells with Env-VRPs and SHIV89.6P GagEnv and EnvGag VLPs. MAGI cells were infected with SHIV89.6P Env-VRP (MOI 1.
Figure 12B:
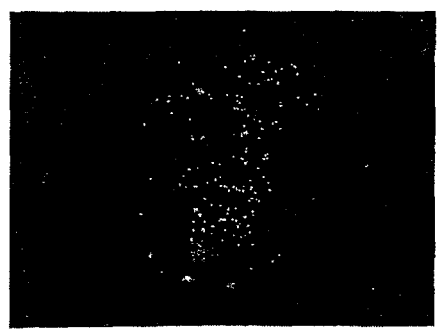
Figure 12C:
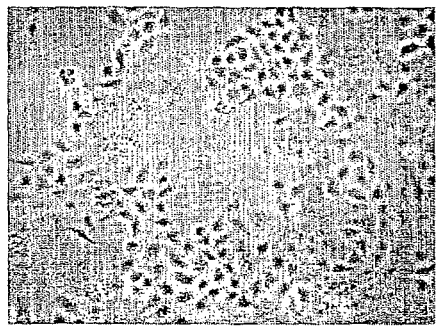
Figure 12D:

Infection of MAGI cells with Env-VRP resulted in focal fusion of cells, with each focus presumably initiated by the infection of an individual cell with an Env-VRP particle (FIG. 12A). Thus, syncytia can form without the production of new infectious particles. Infection with the transmissible chimeric particles (either GagEnv or EnvGag chimeric particles produced in Vero cells) also resulted in the formation of syncytia in MAGI cell monolayers, and these were readily detectable by phase contrast (FIG. 12C) or by fluorescent antibody staining with anti-Env serum (FIGS. 12B and 12C). These results definitively demonstrate the presence of chimeric particles capable of infecting these cells and programming the synthesis of biologically active gp160. However, few if any new transmissible chimeric particles were produced in MAGI cells. It was subsequently found that both Gag and Env were expressed well from Gag-VRP and Env-VRP infecting individually, but that Gag was not expressed well in MAGI cells electroporated with either the GagEnv or EnvGag replicon RNAs. To facilitate this analysis, fibroblast cell lines (i.e., Vero cells), which express the CD4 and CCR5 co-receptors isolated from human or rhesus, were developed. These cell lines exhibit cell surface expression of the receptors and are useful for analyzing the chimeric particles disclosed herein.

Figure 13A:
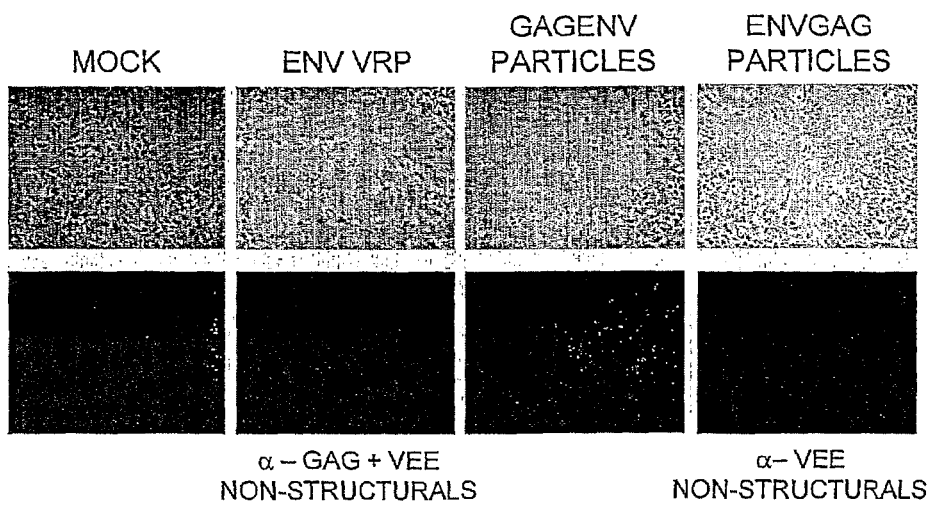
FIGS. 13A and B show infection of 3T3-CD4-CCR5 cells with chimeric GagEnv and EnvGag particles and synthesis of new chimeric GagEnv and EnvGag particles.

As an alternative, Gag and Env expression was demonstrated in 3T3-CD4-CCR5 cells infected with GagEnv and EnvGag particles produced in Vero cells and stained with anti-gp120 b12 antibody or with sera from mice inoculated with Gag-VRP to detect SHIV structural protein by indirect IFA. To detect VEE non-structural proteins, sera from mice inoculated with ovalbumin and empty VRP (VRP that do not express an antigen from the 26S promoter) were used. 3T3-CD4-CCR5 cell mock infected or infected with Env-VRP, as well as NIH 3T3 cells which do not express human CD4 and CCR5 served as controls. Representative slides stained with anti-Gag or anti-VEE non-structural mouse sera are shown in FIG. 13A. The syncytia formed in the monolayers infected with GagEnv chimeric particles were consistently positive for VEE non-structural proteins as well as for SHIV structural proteins. The syncytia formed in the monolayers infected with Env-VRP stained with the sera from Gag-VRP infected mice, indicating the presence of antibodies to the non-structural proteins in the sera. On occasion, a few cells surrounding the syncytia formed in the monolayers that were distinctly positive for gene expression. NIH 3T3 cells which do not express the appropriate receptors for infection by the chimeric particles did not produce syncytia and were indistinguishable from mock-infected cells, indicating that the staining with anti-Gag required infection and gene expression, and was not merely an artifact from the infecting inoculum. These results demonstrate that chimeric particles are capable of infecting cells expressing human CD4 and CCR5 and are capable of directing RNA replication.

Figure 13B:
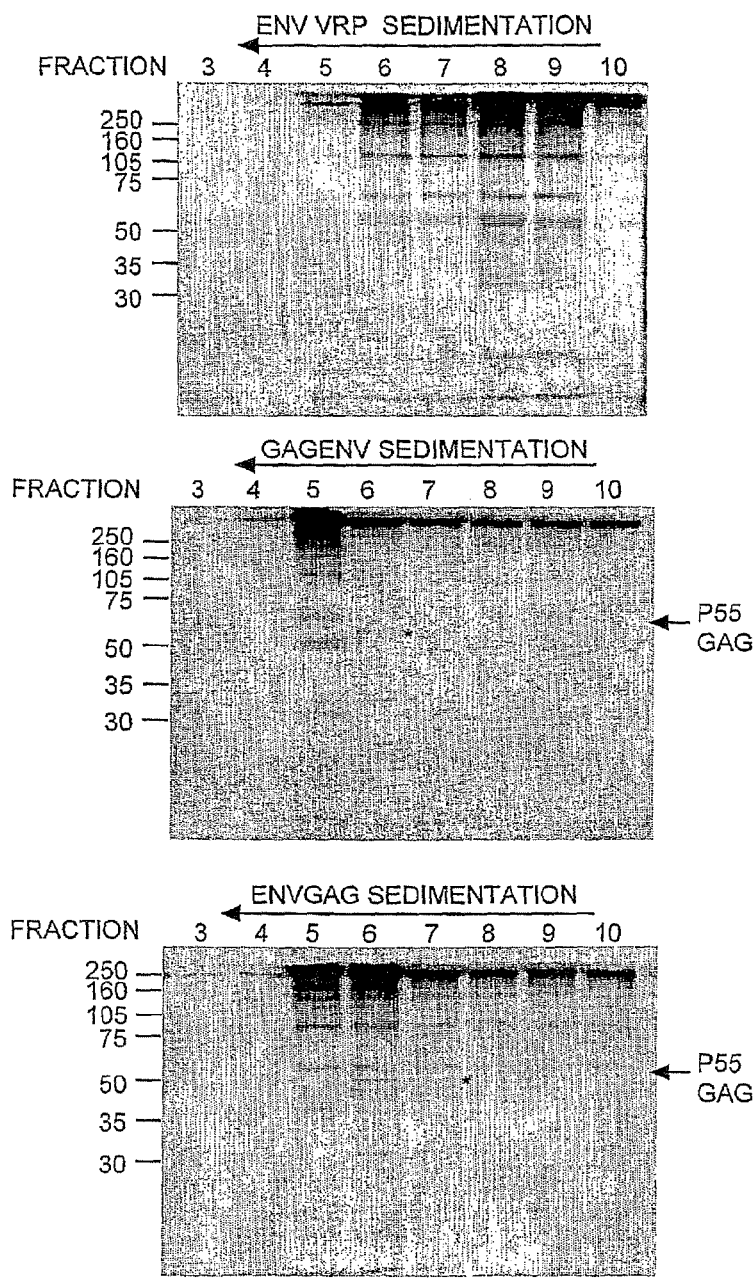
FIG. 13B shows fluorographs of proteins isolated from 3T3-CD4-CCR5 cells infected with Env VRP (upper panel) and chimeric GagEnv and EnvGag particles (lower panels). Cell monolayers were mock-infected or infected with either chimeric particles, or with 10 IU of Env-VRP. Six hpi, cells were metabolically labeled with $^{35}$S PRO-MIX™ (50 mCi/mL). Twenty-four hpi, the cell monolayers were lysed with NP-40 lysis buffer. Anti-SIV monkey antiserum was used to immunoprecipitate Gag and Env from the cell lysates. The cell culture media were clarified, filtered through a 0.2 μm filter and placed on a 20%-60% discontinuous step gradient and particles were banded by centrifugation. One mL fractions starting at the bottom of the gradient were collected and chimeric particles were immunoprecipitated using anti-SIV monkey serum. The immunoprecipitated supernatants were separated on 10% SDS-PAGE gels. The gels were fixed, fluorographed and exposed to a phosphorimager screen. The migration of p55 Gag is noted with the *.
Figure 14A:
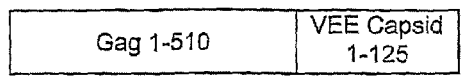
FIGS. 14A and B depict fusion proteins between Gag and a fragment of the VEE capsid protein.
Figure 14B:
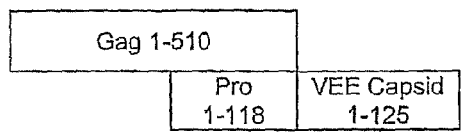
FIG. 14B depicts a VEE capsid protein fused to the first 118 amino acids of Pro, so that the VEE capsid is expressed only after frameshift into the Pro-Pol open reading frame. Amino acid numbering corresponds to the SHIV89.6P sequence.
Figure 15A:
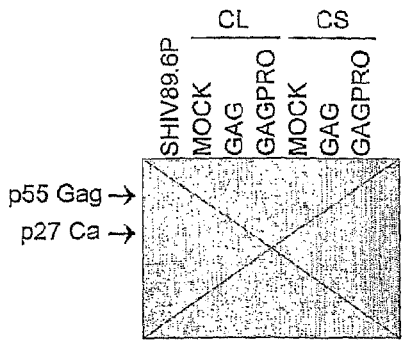
FIGS. 15A and B show the protease expression for particle maturation.
Figure 15B:
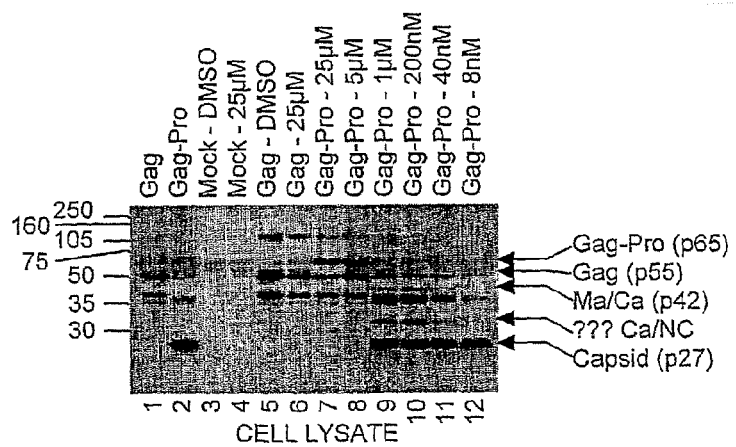
FIG. 15B shows the inhibition of SIV protease activity by saquinavir. Vero cells were either mock-transfected or transfected with Gag or Gag-Pro RNA by electroporation and placed in media containing either DMSO or the indicated concentrations of the protease inhibitor saquinavir. Twenty-four hours post-electroporation, the cells were lysed with NP-40 lysis buffer and the supernatants were clarified and concentrated through 20% OPTIPREP®. Aliquots of lysate and concentrated supernatant were separated by 10% SDS PAGE, transferred to a PVDF membrane, and probed with α-SIV monkey sera (IAVI-0 pooled monkey sera).
Figure 15B:
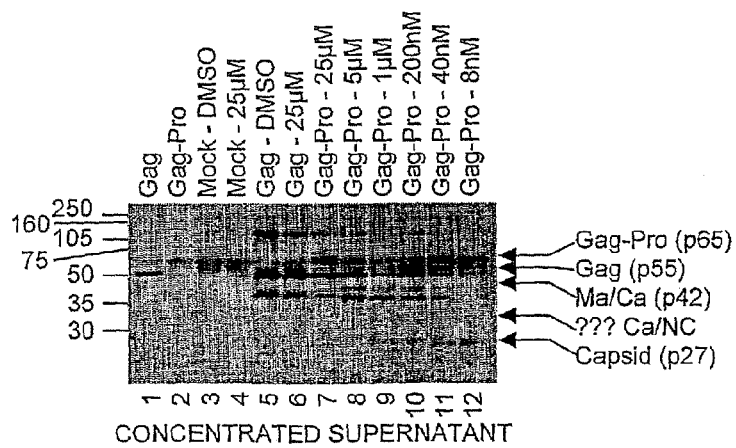

To demonstrate that newly synthesized chimeric particles were assembled and released in the infections of 3T3-CD4-CCR5 cells, cells were metabolically radiolabeled shortly after infection. While Gag and Env were undetectable in the cell lysates at 24 hpi, centrifugation on OPTIPREP® gradients and concentration of the collected fractions by immunoprecipitation with anti-SIV monkey serum, provided detection of Gag in faction 6 and 7 from cells infected with GagEnv and EnvGag chimeric particles (FIG. 13B). Gag was not detected in the supernatants from Env-VRP infected cells. The density of the GagEnv chimeric particles ranged between 1.17 to 1.18 g/mL, and the EnvGag chimeric particles had a density of 1.13 g/mL. This experiment in combination with the immunofluorescence data demonstrate that GagEnv and EnvGag chimeric particles are able to infect susceptible cells, replicate RNA, and assemble and release newly synthesized GagEnv and EnvGag chimeric particles.

To evaluate infection of these chimeric particles in vivo, CD4/CCR5 transgenic mice are used as a model for infection. Moreover, induction of humoral antibodies is assessed by ELISA against gp120 and by neutralization assays. Cell-mediated immunity is determined for Gag using splenocytes from immunized animals in an interferon γ ELISPOT assay.

EXAMPLE 7

Quantitative Assays for Chimeric Particles

To quantitatively measure chimeric particles, chimeric particles are concentrated and partially purified by centrifugation on a discontinuous gradient (OPTIPREP®). The total number of physical particles are estimated indirectly by p27 immunoassay. The p27 assay is available in kit form (Zeptometrix, Retrotek SIV p27 Antigen Kit, Zeptometrix Corporation, Buffalo, N.Y.) and is sufficiently sensitive to detect and quantitate chimeric particles from electroporated Vero cells. Other characteristics of the same chimeric particle preparation are determined as a ratio, with the p27 value as the denominator. Replicon RNA containing particles are determined by a real-time quantitative PCR assay after RNase treatment of the partially purified particles to eliminate free replicon RNA from lysed cells. Infectious particles are determined by a "plaque" assay on either CD4-CCR5-3T3 cells or a Vero cell line expressing CD4 and CCR5 co-receptors. The amount of Env and Gag included in the envelopes of these particles is estimated by metabolic radiolabelling with [$^{35}$S]-methionine during their production, followed by quantitation of the Env and Gag bands displayed by SDS-PAGE. Alternatively, Gag and Env content is estimated by semi-quantitative western blot compared to known standards. Radiolabelling experiments reveal both the level of Gag and Env in the particles as well as the extent to which these proteins are processed. These assays provide information analogous to a particle:pfu ratio and develop a broad quantitative and qualitative picture of the particle preparations obtained from Vero electroporations and from passage in co-receptor bearing cells. These values also provide quantitative and qualitative benchmarks for comparison in experiments designed to improve both chimeric particle production and infectivity.

EXAMPLE 8

Improved Assembly and Maturation of Chimeric Particles

Packaging of Replicon RNA Using a VEE Capsid Fragment The amino terminal 125 amino acids of alphavirus capsid proteins serve to specifically bind the virus genomic RNA for packaging into virions (Perri, et al. (2003) *J. Virol.* 77:10394-10403). This is a highly specific process resulting in the exclusive inclusion of genomic RNA into virus particles. The cis-acting VEE packaging signal is contained within the replicon RNA (Pushko, et al. (1997) *Virol.* 69:389-401), and binding of the relevant VEE capsid fragment to VEE RNA has been demonstrated, even when that fragment is a part of a chimeric capsid protein (Perri, et al. (2003) *J. Virol.* 77:10394-10403). Assembly of Gag-Pol precursors into normal lentivirus cores indicates that the Gag precursor could accommodate the carboxy terminal addition of the relevant VEE capsid fragment. In addition, it may be possible to reduce the size of the capsid fragment while retaining its functional RNA binding characteristics, as indicated by studies of Sindbis virus RNA packaging (Geigenmuller-Gnirke, et al. (1993) *J. Virol.* 67(3): 1620-6).

Accordingly, the VEE capsid fragment sequences are placed downstream of the Gag open reading frame such that the VEE capsid fragment will be synthesized in frame as a fusion protein (FIG. 14A). This modified Gag gene is encoded in the VEE replicon RNA, and its expression is monitored following electroporation of Vero cells. Particle formation is measured by p27 immunoassay, the level of replicon incorporation into the particles is determined by real-time PCR, and both parameters are compared with particles produced with replicon RNA containing only the Gag gene. Alternative configurations include positioning the capsid fragment so that a Gag-capsid fusion protein is synthesized only after normal ribosomal frame-shifting. In this iteration, the VEE capsid fragment is contained in a frame-shifted molecule containing Gag through amino acid 392 (SHIV89.6P numbering), Pro amino acids 1-118, and amino acids 1-125 of the VEE capsid. Both of these iterations are tested with capsid fragments joined to the precursor with linkers of increasing length or with capsid fragments of decreasing size.

Inclusion of a Protease. The Gag component of the chimeric particle replicon genome ends with the stop codon at the end of the Gag open reading frame. In the absence of protease, unprocessed Gag is incorporated into the chimeric particles, and these assemble as immature cores. In the context of a normal retrovirus life cycle, immature particles are incapable of productive infection (Kohl, et al. (1988) *Proc. Natl. Acad. Sci. USA* 88:4686-4690). In the context of the chimeric particles, unprocessed Gag could impede the release of the replicon genome, greatly reducing the specific infectivity of the chimeric particles. However, low infectivity may be partially or entirely compensated for by the ability of the chimeric particle to self-propagate in host cells.

To determine if inclusion of an active protease (Pro) would lead to the formation of mature chimeric particles, several experiments were conducted. Gag and the protease domain of Pol were PCR-amplified from SIVsmH4 and placed into the pVR21 vector. Expression of protease from the frame-shift was preserved. RNA transcribed from linearized SIVsmH4 Gag or GagPro plasmid DNA was transfected into Vero cells by electroporation. After 19 hours, the cells were lysed with NP-40 lysis buffer and the supernatants were concentrated by centrifugation through 20% OPTIPREP®. A portion of the cell lysates and concentrated supernatant was fractionated by 15% SDS-PAGE and transferred to a PVDF membrane for western blot analysis, probing with anti-Gag monoclonal antibody kk64 which recognizes p27 capsid. Gag (p55) was detected in cell lysates and concentrated supernatants from Vero cells transfected with SIVsmH4 Gag RNA (FIG. 15A). Cell lysates from Vero cells transfected with SIVsmH4 GagPro RNA was processed as detected by a reduced level of p55 and a prominent band corresponding to p27 capsid. Gag was not detected in the concentrated supernatants from Vero cells transfected with GagPro RNA. It is believed that the high level of expression from the 26S promoter resulted in an overexpression of protease which cleaved p55 Gag prematurely, before assembly of immature Gag particles. A second experiment was performed in which the activity of the protease was attenuated by treating cells electroporated with the Gag/Pro replicon RNA with saquinavir. With increasing saquinavir concentration, Gag processing was inhibited and extracellular particles were formed (FIG. 15B). This result indicates that by reducing the activity of Pro, mature particles can be assembled and released.

Attenuation of Pro activity can further be achieved in three ways. In a first approach, a truncated RT sequence (tRT) is added to the 3' end of the Pro open reading frame. As part of this precursor (with the tRT extension from the carboxy terminus), Pro is less active and self cleavage of Pro from the precursor is delayed due to the requirement for both amino and carboxy terminal cleavage. This approach is analyzed in the context of replicons with and without the tRT extension. The VEE capsid fragment approach can be combined with the inclusion of protease by extending the carboxy terminus of the fusion protein with the VEE capsid fragment rather than with tRT. As a second modification, the Pro gene is mutated to produce a less active protease. The protease gene has been studied extensively in this regard, facilitating the choice of mutation(s) to produce a range of protease activities that can be tested in the Gag replicon (Rose, et al. (1995) *J. Virol.* 69:2751-2758). Mutation of the frame-shifting site is also conducted to reduce the relative level of Gag/Pro or Gag/Pro/tRT precursor (Evans, et al. (2004) *J. Virol.* 78:11715-11725). In a third approach, the Gag gene in the replicon is substituted with a modified Gag/Pol precursor gene in which the complete RT gene contains multiple mutations in the active site, and IN is either mutated or deleted.

Inclusion of Vpu-Env. The accessory protein Vpu is believed to facilitate the maturation of HIV-1 Env and its intracellular trafficking to the plasma membrane for inclusion in budded particles (Bour and Strebel (2003) *Microb. Infect* 11:1029-39). Accordingly, inclusion of Vpu is used to improve the efficiency of chimeric particle production, the amount of Env detectable on such particles as a function of Gag content, and the overall specific infectivity of chimeric particle preparations.

Introduction of gp41 C-terminal truncations. The C-terminal gp41 cytoplasmic tail contains endocytosis and cell sorting motifs that function to internalize Env, leaving less Env on the cell surface. Truncations of the cytoplasmic carboxy tail or mutations in the tyrosine endocytosis motifs have been shown to increase cell surface expression of Env. Moreover, it has been shown that although immature HIV virions fuse with target cells much less efficiently than mature HIV, introduction of a carboxy tail deletion gives rise to equivalent levels of fusion between both immature and mature virions to susceptible target cells. Accordingly, such mutations are used to increase the amount of Env on the surface of the chimeric particles of the present invention may serve as a means to bypass complication involved in chimeric particle maturation mediated by proteolytic cleavage of Gag.

The foregoing is illustrative of the present invention, and is not to be construed as limiting thereof. The invention is defined by the following claims, with equivalents of the claims to be included therein.

We claim:

1. A self-propagating chimeric viral vector comprising a modified alphavirus genome, said modified genome comprising:

(a) alphavirus nsp1, nsp2, nsp3 and nsp4 coding sequences and alphavirus cis-acting sequences comprising alphavirus 5' and 3' untranslated sequences sufficient for replication of the modified alphavirus genome;

(b) lentivirus protease coding sequences; and (c) lentivirus structural protein coding sequences necessary to form a virion, wherein the lentivirus structural protein coding sequences comprise lentivirus capsid, matrix and envelope coding sequences; and wherein the lentivirus is a human immunodeficiency virus (HIV), a simian immunodeficiency virus (SIV) or a SIV/HIV chimera (SHIV);

wherein at least one of the lentivirus structural proteins encoded by the lentivirus structural protein coding sequences is modified to incorporate a nucleic acid binding domain that binds to the modified alphavirus genome; and wherein the combination of the alphavirus cis-acting sequences and the expression of the coding sequences of (a), (b) and (c) are sufficient to form a self-propagating virion that packages the modified alphavirus genome.

2. The viral vector of claim 1, wherein the modified genome is a modified Venezuelan Equine Encephalitis (VEE) virus genome, Sindbis virus genome, Semliki Forest Virus genome, Girdwood genome, or South African Arbovirus 86 genome.

3. The viral vector of claim 1, wherein the lentivirus is HIV-1.

4. The viral vector of claim 1, wherein the lentivirus is HIV-2.

5. The viral vector of claim 1, wherein the alphavirus is VEE and the lentivirus is HIV-1.

6. The viral vector of claim 1, wherein the alphavirus is VEE and the lentivirus is HIV-2.

7. The viral vector of claim 1, wherein the lentivirus protease coding sequences encode an attenuated lentivirus protease.

8. The viral vector of claim 1, wherein the modified genome further comprises a heterologous nucleic acid encoding a peptide or protein.

9. The viral vector of claim 8, wherein the peptide or protein is expressed as part of a fusion protein with a virion structural protein.

10. The viral vector of claim 8, wherein the peptide or protein is not expressed as part of a virion structural protein.

11. The viral vector of claim 8, wherein the peptide or protein is an immunogenic peptide or protein.

12. The viral vector of claim 8, wherein the peptide or protein is a targeting peptide or protein.

13. A self-propagating chimeric virus particle comprising the chimeric viral vector of claim 1 packaged in a virion.

14. A nucleic acid encoding the chimeric viral vector of claim 1.

15. A virus particle comprising the nucleic acid of claim 14.

16. A pharmaceutical formulation comprising the viral vector of claim 1 in a pharmaceutically acceptable carrier.

17. A method of making a chimeric virus particle, comprising introducing the viral vector of claim 1 into a cell under conditions sufficient for a chimeric virus particle to be produced, wherein the chimeric virus particle comprises the chimeric viral vector packaged within virion structural proteins from the lentivirus.

18. A method of producing an immune response in a subject, the method comprising:

administering the viral vector of claim 1 to a subject in an immunogenically effective amount so that an immune response is produced in the subject.

19. The method of claim 18, wherein the immune response is induced against a structural protein from the lentivirus.

20. The method of claim 8, wherein the immune response is induced against an immunogenic peptide or protein encoded by a heterologous nucleic acid expressed by the modified genome.

21. A self-propagating chimeric viral vector comprising a modified alphavirus genome, said modified genome comprising:

(d) alphavirus nsp1, nsp2, nsp3 and nsp4 coding sequences and alphavirus cis-acting sequences comprising alphavirus 5' and 3' untranslated sequences sufficient for replication of the modified alphavirus genome;

(e) lentivirus protease coding sequences;

(f) lentivirus structural protein coding sequences necessary to form a virion, wherein the lentivirus structural protein coding sequences comprise lentivirus capsid, matrix and envelope coding sequences; and (g) a packaging sequence that binds to at least one of the lentivirus structural proteins encoded by the lentivirus structural protein coding sequences;

wherein the lentivirus is a human immunodeficiency virus (HIV), a simian immunodeficiency virus (SIV) or a SIV/HIV chimera (SHIV); and wherein the combination of the alphavirus cis-acting sequences, the packaging sequence and the expression of the coding sequences of (a), (b) and (c) are sufficient to form a self-propagating virion that packages the modified alphavirus genome.

22. The viral vector of claim 21, wherein the packaging sequence is a lentivirus packaging sequence.

23. The viral vector of claim 21, wherein the modified genome is a modified Venezuelan Equine Encephalitis (VEE) virus genome, Sindbis virus genome, Semliki Forest Virus genome, Girdwood genome, or South African Arbovirus 86 genome.

24. The viral vector of claim 21, wherein the lentivirus is HIV-1.

25. The viral vector of claim 21, wherein the lentivirus is HIV-2.

26. The viral vector of claim 21, wherein the alphavirus is VEE and the lentivirus is HIV-1.

27. The viral vector of claim 21, wherein the alphavirus is VEE and the lentivirus is HIV-2.

28. The viral vector of claim 21, wherein the lentivirus protease coding sequences encode an attenuated lentivirus protease.

29. The viral vector of claim 21, wherein the modified genome further comprises a heterologous nucleic acid encoding a peptide or protein.

30. The viral vector of claim 29, wherein the peptide or protein is expressed as part of a fusion protein with a virion structural protein.

31. The viral vector of claim 29, wherein the peptide or protein is not expressed as part of a virion structural protein.

32. The viral vector of claim 29, wherein the peptide or protein is an immunogenic peptide or protein.

33. The viral vector of claim 9, wherein the peptide or protein is a targeting peptide or protein.

34. A self-propagating chimeric virus particle comprising the chimeric viral vector of claim 21 packaged in a virion.

35. A nucleic acid encoding the chimeric viral vector of claim 21.

36. A virus particle comprising the nucleic acid of claim 35.

37. A pharmaceutical formulation comprising the viral vector of claim 21 in a pharmaceutically acceptable carrier.

38. A method of making a chimeric virus particle, comprising introducing the viral vector of claim 21 into a cell under conditions sufficient for a chimeric virus particle to be produced, wherein the chimeric virus particle comprises the chimeric viral vector packaged within virion structural proteins from the lentivirus.

39. A method of producing an immune response in a subject, the method comprising:

administering the viral vector of claim 21 to a subject in an immunogenically effective amount so that an immune response is produced in the subject.

40. The method of claim 39, wherein the immune response is induced against a structural protein from the lentivirus.

41. The method of claim 39, wherein the immune response is induced against an immunogenic peptide or protein encoded by a heterologous nucleic acid expressed by the modified genome.

* * * * *

UNITED STATES PATENT AND TRADEMARK OFFICE
CERTIFICATE OF CORRECTION

| | | |
|---|---|---|
| PATENT NO. | : 8,486,420 B2 | Page 1 of 1 |
| APPLICATION NO. | : 11/816360 | |
| DATED | : July 16, 2013 | |
| INVENTOR(S) | : Johnston et al. | |

It is certified that error appears in the above-identified patent and that said Letters Patent is hereby corrected as shown below:

In the Specification:
Column 3, Line 17: "without GagA control RNA."
to read -- without GagΔ control RNA. --

Column 3, Line 22: "GagA, Gag replicon"
to read -- GagΔ, Gag replicon --

Column 33, Line 46: "The SIV 4' sequence"
to read -- The SIV Ψ sequence --

Column 33, Line 56: "used to insert the 4'"
to read -- used to insert the Ψ --

Column 33, Line 62: "the 4' sequence and"
to read -- the Ψ sequence and --

Column 33, Line 66: "putative SIV 4' sequence"
to read -- putative SIV Ψ sequence --

In the Claims:
Column 42, Claim 20, Line 30: "The method of claim 8,"
to read -- The method of claim 18, --

Column 43, Claim 33, Line 17: "The viral vector of claim 9,"
to read -- The viral vector of claim 29, --

Signed and Sealed this
Second Day of September, 2014

Michelle K. Lee
*Deputy Director of the United States Patent and Trademark Office*